(12) United States Patent
Snyder et al.

(10) Patent No.: US 6,420,349 B1
(45) Date of Patent: Jul. 16, 2002

(54) ISOXAZOLINONE ANTIBACTERIAL AGENTS

(75) Inventors: Lawrence B. Snyder, Clinton; Zhizhen Zheng, Cheshire, both of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/782,120

(22) Filed: Feb. 13, 2001

Related U.S. Application Data

(63) Continuation of application No. 09/379,222, filed on Aug. 23, 1999, now abandoned.
(60) Provisional application No. 60/097,574, filed on Aug. 24, 1998.

(51) Int. Cl.$^7$ .................. A61K 31/695; C07D 417/10; C07D 413/10; C07D 261/04
(52) U.S. Cl. .................. 514/60; 544/58.2; 544/60; 544/137; 544/229; 546/209; 548/243; 548/255; 514/63; 514/236.8; 514/252
(58) Field of Search .................. 548/243, 255; 544/58.2, 60, 137, 867, 229; 546/209; 514/63, 227.8, 236.8, 252, 326, 359, 380

(56) References Cited

U.S. PATENT DOCUMENTS

| | | | | |
|---|---|---|---|---|
| 3,767,665 A | * | 10/1973 | Tomita et al. | 548/243 |
| 3,892,745 A | * | 7/1975 | Tomita et al. | 548/243 |
| 4,000,155 A | | 12/1976 | Beck et al. | 548/243 |
| 4,065,463 A | | 12/1977 | Beck et al. | 548/243 |
| 4,705,799 A | | 11/1987 | Gregory | 514/376 |
| 4,929,630 A | * | 5/1990 | Castelhano et al. | 514/380 |
| 4,948,801 A | | 8/1990 | Carlson et al. | 514/307 |
| 5,130,316 A | | 7/1992 | Carlson et al. | 514/255 |
| 5,254,577 A | | 10/1993 | Carlson et al. | 514/376 |
| 5,523,403 A | | 6/1996 | Barbachyn | 544/137 |
| 5,529,998 A | | 6/1996 | Habich et al. | 514/233.8 |
| 5,627,181 A | | 5/1997 | Riedl et al. | 514/236.8 |
| 5,684,023 A | | 11/1997 | Riedl et al. | 514/337 |
| 5,698,574 A | | 12/1997 | Riedl et al. | 514/376 |
| 5,708,169 A | | 1/1998 | Hester et al. | 514/378 |
| 5,843,967 A | | 12/1998 | Riedl et al. | 549/152 |

FOREIGN PATENT DOCUMENTS

| | | | | |
|---|---|---|---|---|
| DE | 4020446 | * | 1/1992 | 548/243 |
| EP | 0693491 A1 | | 1/1996 | |
| EP | 0694543 A1 | | 1/1996 | |
| EP | 0694544 A1 | | 1/1996 | |
| EP | 0697412 A1 | | 2/1996 | |
| JP | 53-135971 | * | 11/1978 | 548/243 |
| WO | 92-17461 | * | 10/1992 | 548/243 |
| WO | 97/10235 | | 3/1997 | |
| WO | 97/14690 | | 4/1997 | |
| WO | 97/43280 | | 11/1997 | |
| WO | 98/07708 | | 2/1998 | |

OTHER PUBLICATIONS

References mailed with prior office action mailed on Nov. 27, 2001.*

* cited by examiner

*Primary Examiner*—Joseph K. McKane
*Assistant Examiner*—Kamal Saeed
(74) *Attorney, Agent, or Firm*—David M. Morse

(57) ABSTRACT

This invention describes isoxazolinone compounds which possess antibacterial activity and are useful in the treatment of bacterial diseases. More particularly, isoxazolinones are provided having the formula

I

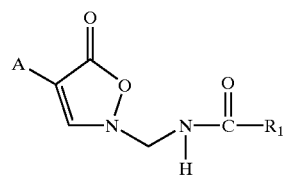

7 Claims, No Drawings

ISOXAZOLINONE ANTIBACTERIAL AGENTS

CROSS-REFERENCE TO RELATED APPLICATIONS

This application is a continuation of application Ser. No. 09/379,222 filed Aug. 23, 1999, now abandoned, which claims the benefit of U.S. Provisional Application Ser. No. 60/097,574 filed Aug. 24, 1998.

BACKGROUND OF THE INVENTION

1. Field of the Invention

The present invention is directed toward new isoxazolinones, methods for their use, and processes for their production. The present invention provides for a compound represented by the general formula

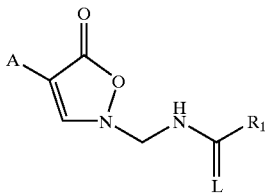

I or a pharmaceutically acceptable salt thereof wherein:

$R_1$ is
  a) H,
  b) $C_{1-8}$ alkyl optionally substituted with one or more F, Cl, OH, $C_{1-8}$ alkoxy, or $C_{1-8}$ acyloxy,
  c) $C_{3-6}$ cycloalkyl, or
  d) $C_{1-8}$ alkoxy;

L is oxygen or sulfur;

A is a)

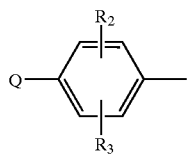

b)

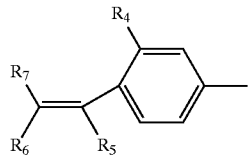

c) a 5-membered heteroaromatic moiety having one to three hetero atoms selected from the group consisting of S, N, and O, wherein the 5-membered heteroaromatic moiety is bonded via a carbon atom and can additionally have a fused-on benzene or naphthyl ring, and wherein the heteroaromatic moiety is optionally substituted with one to three $R_8$, d) a 6-membered heteroaromatic moiety having at least one nitrogen atom, wherein the heteroaromatic moiety is bonded via a carbon atom, wherein the 6-membered heteroaromatic moiety can additionally have a fused-on benzene or naphthyl ring, wherein the heteroaromatic moiety is optionally substituted with one to three $R_9$, e) a β-carbolin-3-yl, or indolizinyl bonded via the 6-membered ring, optionally substituted with one to three $R_9$, f)

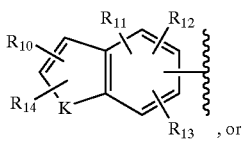, or g)

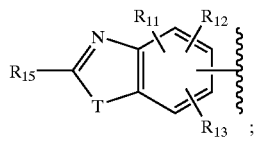;

wherein $R_2$ and $R_3$ are each independently
  a) H,
  b) F,
  c) Cl,
  d) Br,
  e) $C_{1-6}$ alkyl,
  f) $NO_2$,
  g) I,
  h) $C_{1-6}$ alkoxy,
  i) OH
  j) amino,
  k) cyano, or
  l) $R_2$ and $R_3$ taken together are $-O(CH_2)_h-O$;

wherein $R_4$ is
  a) H,
  b) $C_{1-2}$ alkyl,
  c) F, or
  d) OH;

$R_5$ is
  a) H,
  b) $CF_3$,
  c) $C_{1-3}$ alkyl optionally substituted with one or more halo,
  d) phenyl optionally substituted with one or more halo,
  e) $R_5$ and $R_6$ taken together are a 5-, 6-, or 7-membered ring of the formula,

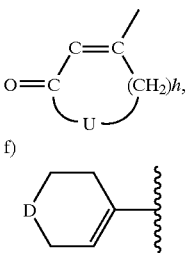

f)

in which D is S, O or $NR_{86}$ in which $R_{86}$ is H or $C_{1-6}$ alkyl or g) $R_5$ and $R_6$ taken together are $-(CH_2)_k-$, when $R_7$ is an electron-withdrawing group;

$R_6$ and $R_7$ at each occurrence are the same or different and are
  a) an electron-withdrawing group,
  b) H,
  c) $CF_3$,
  d) $C_{1-3}$ alkyl optionally substituted with one halo,
  e) phenyl, provided at least one of $R_6$ and $R_7$ is an electron-withdrawing group, or f) $R_6$ and $R_7$ taken together are a 5-, 6-, or 7-membered ring of the formula,

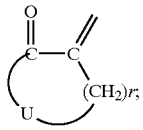

U is
  a) $CH_2$,
  b) O,
  c) S or,
  d) $NR_{16}$;
$R_{16}$ is
  a) H or
  b) $C_{1-5}$ alkyl;
wherein $R_8$ is
  a) carboxyl,
  b) halo,
  c) —CN,
  d) mercapto,
  e) formyl,
  f $CF_3$,
  g) $NO_2$,
  h) $C_{1-6}$ alkoxy,
  i) $C_{1-6}$ alkoxycarbonyl,
  j) $C_{1-6}$ alkythio,
  k) $C_{1-6}$ acyl,
  l) —$NR_{17}R_{18}$, m) 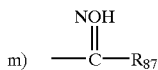

in which $R_{87}$ is H or $C_{1-6}$ alkyl,
  n) $C_{1-6}$ alkyl optionally substituted with OH, sulfamoyl, $C_{1-5}$ alkoxy, $C_{1-5}$ acyl, or —$NR_{17}R_{18}$,
  o) $C_{2-8}$ alkyl optionally substituted with one or two $R_{19}$,
  p) phenyl optionally substituted with one or two $R_{19}$,
  q) a 5- or 6-membered saturated or unsaturated heterocyclic moiety having one to three atoms selected from the group consisting of S, N, and O, optionally substituted with one or two $R_{19}$, or

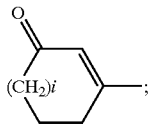

$R_{17}$ and $R_{18}$ at each occurrence are the same or different and are
  a) H,
  b) $C_{1-4}$ alkyl,
  c) $C_{5-6}$ cycloalkyl, or
  d) $R_{17}$ and $R_{18}$ taken together with the nitrogen atom is a 5- or 6-membered saturated or unsaturated heterocyclic moiety which optionally has a further heteroatom selected from the group consisting of S, N, O, and can in turn be optionally substituted with, including on the further nitrogen atom, $C_{1-3}$ alkyl, formyl, a 5- or 6-membered heteroaromatic moiety containing 1–3 O, N or S,

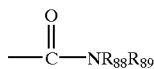

in which $R_{88}$ and $R_{89}$ are each independently hydrogen or $C_{1-6}$ alkyl, $SO_2R_{90}$ in which $R_{90}$ is H or $C_{1-6}$ alkyl, or $C_{1-3}$ acyl optionally substituted with 1 or more F, Cl or OH;

$R_{19}$ is
  a) carboxyl,
  b) halo,
  c) —CN,
  d) mercapto,
  e) formyl,
  f) $CF_3$,
  g) $NO_2$,
  h) $C_{1-6}$ alkoxy,
  i) $C_{1-6}$ alkoxycarbonyl,
  j) $C_{1-6}$ alkythio,
  k) $C_{1-6}$ acyl,
  l) $C_{1-6}$ alkyl optionally substituted with OH, $C_{1-5}$ alkoxy, $C_{1-5}$ acyl, or —$NR_{17}R_{18}$,
  m) phenyl,
  n) —C(=O)$NR_{20}R_{21}$,
  o) —N $R_{17}R_{18}$,
  p) —N($R_{20}$)(—$SO_2R_{22}$),
  q) —$SO_2$—$NR_{20}R_{21}$, or
  r) —S(=O)$_tR_{22}$;

$R_{20}$ and $R_{21}$ at each occurrence are the same or different and are
  a) H,
  b) $C_{1-6}$ alkyl, or
  c) phenyl;

$R_{22}$ is
  a) $C_{1-4}$ alkyl, or
  b) phenyl optionally substituted with $C_{1-4}$ alkyl;

wherein $R_9$ is
  a) carboxyl,
  b) halo,
  c) —CN,
  d) mercapto,
  e) formyl,
  f) $CF_3$,
  g) $NO_2$,
  h) $C_{1-6}$ alkoxy,
  i) $C_{1-6}$ alkoxycarbonyl,
  j) $C_{1-6}$ alkythio,
  k) $C_{1-6}$ acyl,
  l) —$NR_{23}R_{24}$,
  m) $C_{1-6}$ alkyl optionally substituted with OH, $C_{1-5}$ alkoxy, $C_{1-5}$ acyl, or —$NR_{23}R_{24}$,
  n) $C_{2-8}$ alkenylphenyl optionally substituted with one or two $R_{25}$,
  o) phenyl optionally substituted with one or two $R_{25}$,
  p) a 5- or 6-membered saturated or unsaturated heterocyclic moiety having one to three atoms selected from the group consisting of S, N, and O, optionally substituted with one or two $R_{25}$, or q) 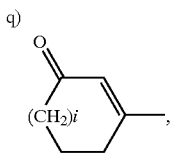

$R_{23}$ and $R_{24}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl, or
g) $R_{23}$ and $R_{24}$ taken together with the nitrogen atom is a 5- or 6-membered saturated heterocyclic moiety which optionally has a further hetero atom selected from the group consisting of S, N, O, and can in turn be optionally substituted with, including on the further nitrogen atom, phenyl, pyrimidyl, $C_{1-3}$ alkyl, or $C_{1-3}$ acyl;

$R_{25}$ is
a) carboxyl,
b) halo,
c) —CN,
d) mercapto,
e) formyl,
f) $CF_3$,
g) $NO_2$,
h) $C_{1-6}$ alkoxy,
i) $C_{1-6}$ alkoxycarbonyl,
j) $C_{1-6}$ alkythio,
k) $C_{1-6}$ acyl,
l) phenyl,
m) $C_{1-6}$ alkyl optionally substituted with OH, azido, $C_{1-5}$ alkoxy, $C_{1-5}$ acyl, —$NR_{32}R_{33}$, —$SR_{34}$, —O—$SO_2R_{35}$, or

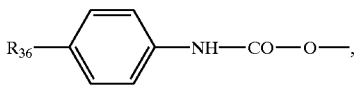

n) —C(=O)$NR_{26}R_{27}$,
o) —$NR_{23}R_{24}$,
p) —N($R_{26}$)(—$SO_2R_{22}$),
q) —$SO_2$—$NR_{26}R_{27}$, or
r) —S(=O)$_iR_{22}$,
s) —CH=N—$R_{28}$, or
t) —CH(OH)—$SO_3R_{31}$;

$R_{22}$ is the same as defined above;

$R_{26}$ and $R_{27}$ at each occurrence are the same or different and are
a) H,
b) $C_{1-6}$ alkyl,
c) phenyl, or
d) tolyl;

$R_{28}$ is
a) OH,
b) benzyloxy,
c) —NH—C(=O)—$NH_2$,
d) —NH—C(=S)—$NH_2$, or
e) —NH—C(=NH)—$NR_{29}R_{30}$;

$R_{29}$ and $R_{30}$ at each occurrence are the same or different and are
a) H,or
b) $C_{1-4}$ alkyl optionally substituted with phenyl or pyridyl;

$R_{31}$ is
a) H, or
b) a sodium ion;

$R_{32}$ and $R_{33}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl,
g) $R_{32}$ and $R_{33}$ taken together are a 5- or 6-membered saturated heterocyclic moiety having one to three atoms selected from the group consisting of S, N, O, optionally substituted with, including on the nitrogen atom, phenyl, pyrimidyl, $C_{1-3}$ alkyl, or $C_{1-3}$ acyl,
h) —P(O)($OR_{37}$)($OR_{38}$), or
i) —$SO_2$—$R_{39}$;

$R_{34}$ is

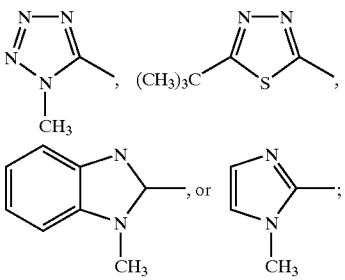

$R_{35}$ is $C_{1-3}$ alkyl;

$R_{36}$ is
a) $C_{1-6}$ alkoxycarbonyl, or
b) carboxyl;

$R_{37}$ and $R_{38}$ at each occurrence are the same or different and are
a) H,or
b) $C_{1-3}$ alkyl;

$R_{39}$ is
a) methyl,
b) phenyl, or
c) tolyl;

wherein K is
a) O,
b) S, or
c) $NR_{40}$ in which $R_{40}$ is hydrogen, formyl, $C_{1-4}$ alkyl, $C_{1-4}$ acyl, phenyl, $C_{3-6}$ cycloalkyl, —P(O)($OR_{37}$)($OR_{38}$) or —$SO_2$—$R_{39}$ in which $R_{37}$, $R_{38}$ and $R_{39}$ are as defined above;

$R_{10}$, $R_{11}$, $R_{12}$, $R_{13}$, $R_{14}$ and $R_{15}$ at each occurrence are the same or different and are
a) H,
b) formyl,
c) carboxyl,
d) $C_{1-6}$ alkoxycarbonyl,
e) $C_{1-8}$ alkyl,
f) $C_{2-8}$ alkenyl,
wherein the substituents (e) and (f) can be optionally substituted with OH, halo, $C_{1-6}$ alkoxyl, $C_{1-6}$ acyl, $C_{1-6}$ alkylthio or $C_{1-6}$ alkoxycarbonyl, or phenyl optionally substituted with halo, g) an aromatic moiety having 6 to 10 carbon atoms optionally substituted with carboxyl, halo, —CN, formyl, $CF_3$, $NO_2$, $C_{1-6}$ alkyl, $C_{1-6}$ alkoxy, $C_{1-6}$ acyl, $C_{1-6}$ alkylthio, or $C_{1-6}$ alkoxycarbonyl;
h) —$NR_{42}R_{43}$,
i) $OR_{44}$,
j) —$S(=O)_i$—$R_{45}$,
k) —$SO_2$—$N(R_{46})(R_{47})$, or
l) a radical of the following formulas:

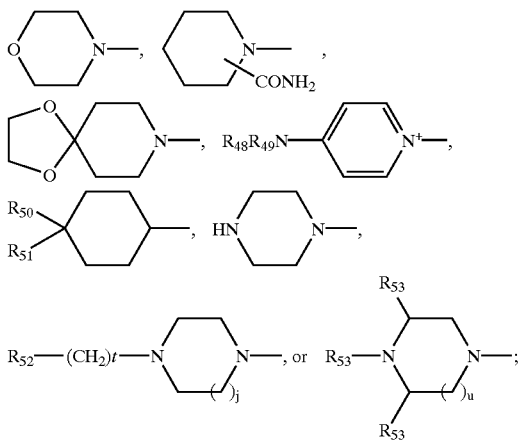

$R_{19}$ is the same as defined above;

T is
a) O,
b) S, or
c) $SO_2$;

$R_{42}$ and $R_{43}$ at each occurrence are the same or different and are
a) H,
b) $C_{3-6}$ cycloalkyl,
c) phenyl,
d) $C_{1-6}$ acyl,
e) $C_{1-8}$ alkyl optionally substituted with OH, $C_{1-6}$ alkoxy which can be substituted with OH, a 5- or 6-membered aromatic heterocyclic moiety having one to three atoms selected from the group consisting of S, N, and O, phenyl optionally substituted with OH, $CF_3$, halo, —$NO_2$, $C_{1-4}$ alkoxy, —$NR_{48}R_{49}$, or

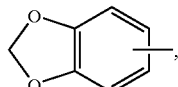
f)

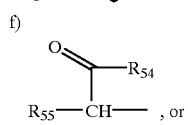
, or
g)

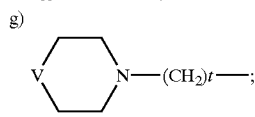

V is
a) O,
b) $CH_2$, or
c) $NR_{56}$;

$R_{48}$ and $R_{49}$ at each occurrence are the same or different and are
a) H, or
b) $C_{1-4}$ alkyl;

$R_{54}$ is
a) OH,
b) $C_{1-4}$ alkoxy, or
c) —$NR_{57}R_{58}$;

$R_{55}$ is
a) H, or
b) $C_{1-7}$ alkyl optionally substituted with indolyl, OH, mercaptyl, imidazoly, methylthio, amino, phenyl optionally substituted with OH, —C(=O)—$NH_2$, —$CO_2H$, or —C(=NH)—$NH_2$;

$R_{56}$ is
a) H,
b) phenyl, or
c) $C_{1-6}$ alkyl optionally substituted by OH;

$R_{57}$ and $R_{58}$ at each occurrence are the same or different and are
a) H,
b) $C_{1-5}$ alkyl,
c) $C_{1-3}$ cycloalkyl, or
d) phenyl;

$R_{44}$ is
a) $C_{1-8}$ alkyl optionally substituted with $C_{1-6}$ alkoxy or $C_{1-6}$ hydroxy, $C_{3-6}$ cycloalkyl, a 6-membered aromatic optionally benzo-fused heterocyclic moiety having one to three nitrogen atoms, which can in turn be substituted with one or two —$NO_2$, $CF_3$, halo, —CN, OH, $C_{1-5}$ alkyl, $C_{1-5}$ alkoxy, or $C_{1-5}$ acyl, b)
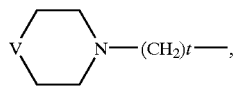

c) phenyl, or
d) pyridyl;

$R_{45}$ is
a) $C_{1-16}$ alkyl,
b) $C_{2-16}$ alkenyl,
wherein the substituents (a) and (b) can be optionally substituted with $C_{1-6}$ alkoxycarbonyl, or a 5-, 6-, or 7-membered aromatic heterocyclic moiety having one to three atoms selected from the group consisting of S, N, and O,
c) an aromatic moiety having 6 to 10 carbon atoms, or
d) a 5-, 6-, or 7-membered aromatic heterocyclic moiety having one to three atoms selected from the group of S, N, and O, wherein the substituents (c) and (d) can be optionally substituted with carboxyl, halo, —CN, formyl, $CF_3$, —$NO_2$, $C_{1-6}$ alkyl, $C_{1-6}$ alkoxy, $C_{1-6}$ acyl, $C_{1-6}$ alkylthio, or $C_{1-6}$ alkoxycarbonyl;

$R_{46}$ and $R_{47}$ at each occurrence are the same or different and are
a) H,
b) phenyl,
c) $C_{1-6}$ alkyl, or
d) benzyl;

$R_{50}$ and $R_{51}$ at each occurrence are the same or different and are
a) H,
b) OH,
c) $C_{1-6}$ alkyl optionally substituted with —$NR_{48}R_{49}$ in which $R_{48}$ and $R_{49}$ are as defined above,
d) $R_{50}$ and $R_{51}$ taken together are =O;

$R_{52}$ is
- a) an aromatic moiety having 6 to 10 carbon atoms,
- b) a 5- or 6-membered aromatic optionally benzo-fused heterocyclic moiety having one to three atoms selected from the group consisting of S, N, and O, wherein the substituents (a) and (b) can in turn be optionally substituted with one or three —$NO_2$, $CF_3$, halo, —CN, OH, phenyl, $C_{1-5}$ alkyl, $C_{1-5}$ alkoxy, or $C_{1-5}$ acyl,
- c) morpholinyl,
- d) OH,
- e) $C_{1-6}$ alkoxy,
- f) —$NR_{48}R_{49}$ in which $R_{48}$ and $R_{49}$ are as defined above,
- g) —C(=O)—$R_{59}$, or
- h) 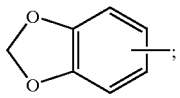

$R_{53}$ is
- a) H,
- b) formyl,
- c) $C_{1-4}$ alkyl,
- d) $C_{1-4}$ acyl,
- e) phenyl,
- f) $C_{3-6}$ cycloalkyl,
- g) —P(O)($OR_{37}$)($OR_{38}$), or
- h) —$SO_2R_{39}$, in which $R_{37}$, $R_{38}$ and $R_{39}$ are as defined above;

$R_{59}$ is
- a) morpholinyl,
- b) OH, or
- c) $C_{1-6}$ alkoxy;

h is 1, 2, or 3;
i is 0, 1, or 2;
j is 0, or 1;
k is 3, 4, or 5;
r is 1, 2, 3, 4, 5 or 6;
t is 0, 1, 2, 3, 4, 5, or 6;
u is 1 or 2; and Q is
- a) hydrogen,
- b) halo,
- c) $NO_2$,
- d) $N_3$,
- e) $C_1$–$C_6$ alkylthio,
- f) 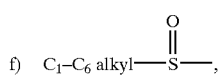
- g) 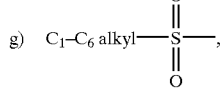
- h) $C_1$–$C_6$ alkyl,
- i) $C_1$–$C_6$ alkoxy,
- j) formyl,
- k) 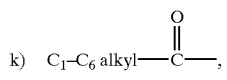
- l) 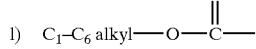
- m) —sulfamoyl ($H_2NSO_2$—),
- n) —NHOH,
- o) 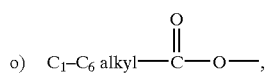
- p) 

in which heteroaryl is a 5- or 6-membered aromatic heterocyclic group having 1–3 hetero atoms selected from O, N or S,

- q) 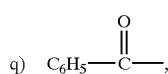
- r) amino,
- s) $C_1$–$C_6$ alkylamino-,
- t) di ($C_1$–$C_6$ alkyl)amino-,
- u) 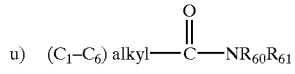

in which $R_{60}$ and $R_{61}$ are each independently hydrogen or $C_1$–$C_6$ alkyl,
- V) OH,
- w) cyano,
- x) hydroxy ($C_1$–$C_6$ alkyl),
- y) 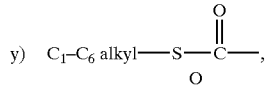
- z) 

in which r is 1–6,

- aa) 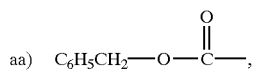
- bb) 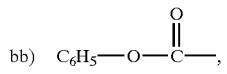
- cc) 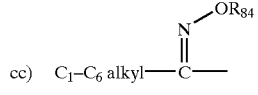

in which $R_{84}$ is hydrogen or $C_{1-6}$ alkyl,

- dd) 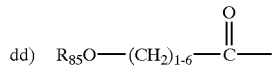

in which $R_{85}$ is hydrogen, $C_{1-8}$ alkyl optionally substituted with one or more F, Cl, OH, $C_{1-8}$ alkoxy or $C_{1-8}$ acyloxy, $C_{3-6}$ cycloalkyl or $C_{1-8}$ alkoxy;

ee) 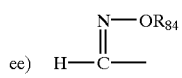

in which $R_{84}$ is hydrogen or $C_{1-6}$ alkyl,
ff) a substituted or unsubstituted $C_6$–$C_{10}$ aryl moiety,
gg) a substituted or unsubstituted monocyclic or bicyclic, saturated or unsaturated, heterocyclic moiety having 1–3 atoms selected from O, N or S, said ring being bonded via a ring carbon or nitrogen to the phenyl substituent,
hh) a monocyclic or bicyclic substituted or unsubstituted heteroaromatic moiety having 1–3 hetero atoms selected from O, N or S, said ring being bonded via a ring carbon or nitrogen to the phenyl substituent and wherein the heteroaromatic moiety can additionally have a fused-on benzene or naphthalene ring;

the substituents for such p, q, ff, gg and hh moieties being selected from 1 or 2 of the following:
1) halo,
2) $C_{1-6}$ alkyl,
3) $NO_2$,
4) $N_3$, 5) 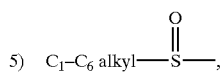

6) 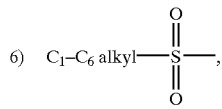

7) formyl,

8) 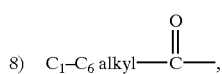

9) 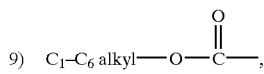

10) 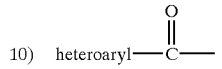

in which heteroaryl is a 5- or 6-membered aromatic heterocyclic group having 1–3 hetero atoms selected from O, N or S, 11) 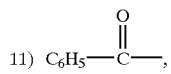

12) 

in which $R_{60}$ and $R_{61}$ are each independently hydrogen or $C_1$–$C_6$ alkyl,
13) OH,
14) hydroxy ($C_1$–$C_6$ alkyl), 15) 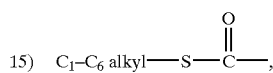

16) 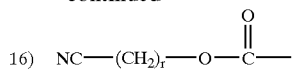

in which r is 1–6,

17) 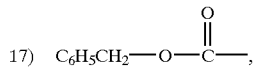

18) —$CH_2$—$R_{80}$ in which $R_{80}$ is
 a) —$OR_{32}$ in which $R_{32}$ is as defined above,
 b) —$SR_{32}$ in which $R_{32}$ is as defined above,
 c) —$NR_{32}R_{33}$ in which $R_{32}$ and $R_{33}$ are as defined above, or
 d) 5- or 6-membered heteroaromatic containing 1–4 O, S or N atoms, 19) 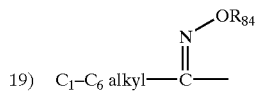

in which $R_{84}$ is as defined above,
20) cyano,
21) carboxyl,
22) $CF_3$,

23) 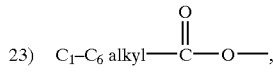

24) 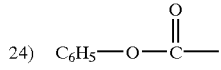

in which the phenyl moiety may be optionally substituted by halo or ($C_1$–$C_6$)alkyl, 25) 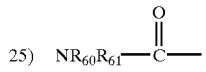

in which $R_{60}$ and $R_{61}$ are as defined above,

26) 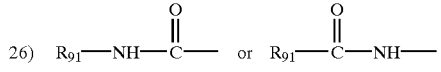

in which $R_{91}$ is a 5- or 6-membered aromatic heterocyclic group having 1–3 O, N or S, 27) 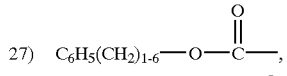

28) 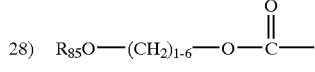

in which $R_{85}$ is as defined above,

29) 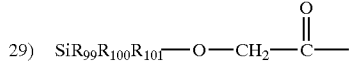

in which $R_{99}$, $R_{100}$ and $R_{101}$ are each independently $C_{1-6}$ alkyl; or
Q and either $R_1$ and $R_2$ taken together form —O—$CH_2$—O.

These derivatives are useful as antimicrobial agents which are effective against a number of human and veterinary pathogens, including gram positive bacteria such as multiply-resistant staphylococci, streptococci, and enterococci, such as methicillin-resistant *Staphylococcus aureus* or vancomycin-resistant *Enterococcus faecium*.

2. Description of the Prior Art

The literature contains a limited number of isoxazolinones used as pre-emergence herbicides. For example in U.S. Pat. No. 4,065,463, 2-methyl4-(trifluoromethyl-m-tolyl)-3-isoxazolin-5-one and 2-methyl-4-(chloro-m-tolyl)-3-isoxazolin-5-one are disclosed as being useful in preventing the growth of weeds which have a deleterious effect on crop production.

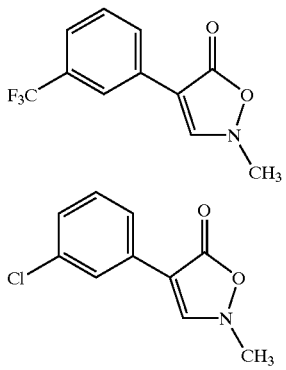

U.S. Pat. No. 4,000,155 discloses the related compound 1,2-dimethyl-4-(trifluoromethyl-m-tolyl)-3-pyrazolin-5-one for the same utility.

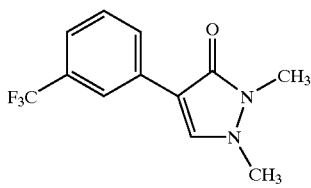

The applicant is not aware of any literature which discloses the use of these compounds as broad spectrum anti-bacterial agents. A different ring system is disclosed in WO 98/07708, which discusses the use of isoxazoline derivatives as anti-bacterial agents,

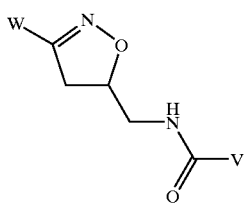

where W is a substituted aryl or heteroaryl system and V is H, or $C_1$–$C_4$ alkyl optionally substituted with F, Cl, OH, $C_1$–$C_4$ alkoxy, or acyloxy.

Oxazolidinones II shown below are a well known class of orally active antibacterial agents. The prior art contains numerous references to these compounds where Y and Z can include a wide variety of substituents. Specific substituted oxazolidinones are discussed in U.S. Pat. Nos. 4,705,799 and 5,523,403 (substituted phenyl 2-oxazolidinones), U.S. Pat. Nos. 4,948,801; 5,254,577; and 5,130,316 (arylbenzene oxazolidinyl compounds), and European Patent Applications 0,697,412; 0,694,544; 0694,543; and 0,693,491 (5 to 9-membered heteroaryl substituted oxazolidinones).

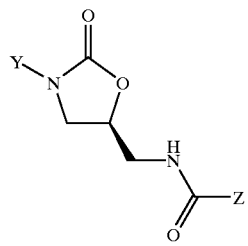

Additionally, certain compounds containing a substituted furanone ring have been reported to possess antibiotic activity. WO 97/14690 discloses

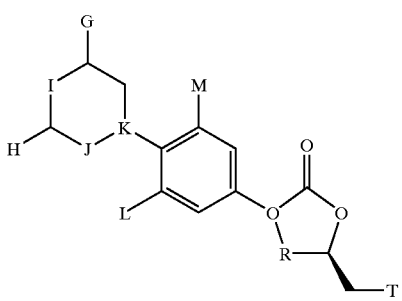

where T is hydroxy or $NHC(O)C_1$–$C_4$ alkyl, M and L are each independently hydrogen or fluoro, G and H are are each independently hydrogen or methyl, K—J is of the formula C=CH, CHCH2 or C(OH)CH2, I is O, SO, SO2 or a substituted nitrogen, and Q—R is $CH_2$—$CH_2$ or $CH$=$CH_2$. Other substituted furanones are discussed in U.S. Pat. No. 5,708,169, WO 97/43280 and WO 97/10235.

SUMMARY OF THE INVENTION

It has now been found that certain substituted isoxazolinones are effective as antibacterial agents. Specifically, the invention covers compounds of the formula I:

I or a pharmaceutically acceptable salt thereof wherein:

$R_1$ is
a) H,
b) $C_{1-8}$ alkyl optionally substituted with one or more F, Cl, OH, $C_{1-8}$ alkoxy, or $C_{1-8}$ acyloxy,
c) $C_{3-6}$ cycloalkyl, or
d) $C_{1-8}$ alkoxy;

L is oxygen or sulfur;

A is a) 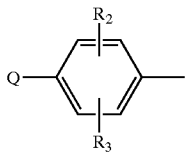

b) 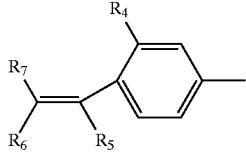

c) a 5-membered heteroaromatic moiety having one to three hetero atoms selected from the group consisting of S, N, and O, wherein the 5-membered heteroaromatic moiety is bonded via a carbon atom and can additionally have a fused-on benzene or naphthyl ring, and wherein the heteroaromatic moiety is optionally substituted with one to three $R_8$, d) a 6-membered heteroaromatic moiety having at least one nitrogen atom, wherein the heteroaromatic moiety is bonded via a carbon atom, wherein the 6-membered heteroaromatic moiety can additionally have a fused-on benzene or naphthyl ring, wherein the heteroaromatic moiety is optionally substituted with one to three $R_9$, e) a β-carbolin-3-yl, or indolizinyl bonded via the 6-membered ring, optionally substituted with one to three $R_9$, f) 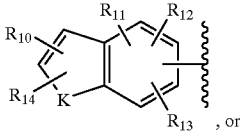, or g) 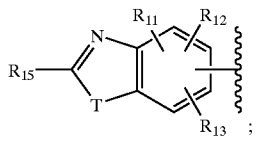;

wherein $R_2$ and $R_3$ are each independently
a) H,
b) F,
c) Cl,
d) Br,
e) $C_{1-6}$ alkyl,
f) $NO_2$,
g) I,
h) $C_{1-6}$ alkoxy,
i) OH
j) amino,
k) cyano, or
l) $R_2$ and $R_3$ taken together are $-O(CH_2)_n-O$;
wherein $R_4$ is
a) H,
b) $C_{1-2}$ alkyl,
c) F, or
d) OH;

$R_5$ is
a) H,
b) $CF_3$,
c) $C_{1-3}$ alkyl optionally substituted with one or more halo,
d) phenyl optionally substituted with one or more halo,
e) $R_5$ and $R_6$ taken together are a 5-, 6-, or 7-membered ring of the formula,

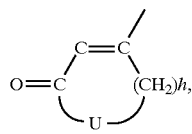

f) 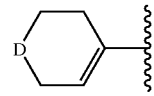

in which D is S, O or $NR_{86}$ in which $R_{86}$ is H or $C_{1-6}$ alkyl, or g) $R_5$ and $R_6$ taken together are $-(CH_2)_k-$, when $R_7$ is an electron-withdrawing group;

$R_6$ and $R_7$ at each occurrence are the same or different and are
a) an electron-withdrawing group,
b) H,
c) $CF_3$,
d) $C_{1-3}$ alkyl optionally substituted with one halo,
e) phenyl, provided at least one of $R_6$ and $R_7$ is an electron-withdrawing group, or
f) $R_6$ and $R_7$ taken together are a 5-, 6-, or 7-membered ring of the formula,

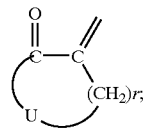

U is
a) $CH_2$,
b) O,
c) S or,
d) $NR_{16}$;
$R_{16}$ is
a) H or
b) $C_{1-5}$ alkyl;
wherein $R_8$ is
a) carboxyl,
b) halo,
c) —CN,
d) mercapto,
e) formyl,
f) $CF_3$,
g) $NO_2$,
h) $C_{1-6}$ alkoxy,
i) $C_{1-6}$ alkoxycarbonyl,
j) $C_{1-6}$ alkythio,
k) $C_{1-6}$ acyl, l) —NR$_{17}$R$_{18}$, m) 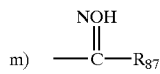

in which R$_{87}$ is H or C$_{1-6}$ alkyl,
n) C$_{1-6}$ alkyl optionally substituted with OH, sulfamoyl, C$_{1-5}$ alkoxy, C$_{1-5}$ acyl, or —NR$_{17}$R$_{18}$,
o) C$_{2-8}$ alkyl optionally substituted with one or two R$_{19}$,
p) phenyl optionally substituted with one or two R$_{19}$,
q) a 5- or 6-membered saturated or unsaturated heterocyclic moiety having one to three atoms selected from the group consisting of S, N, and O, optionally substituted with one or two R$_{19}$, or

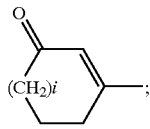

R$_{17}$ and R$_{18}$ at each occurrence are the same or different and are
a) H,
b) C$_{1-4}$ alkyl,
c) C$_{5-6}$ cycloalkyl, or
d) R$_{17}$ and R$_{18}$ taken together with the nitrogen atom is a 5- or 6-membered saturated or unsaturated heterocyclic moiety which optionally has a further hetero atom selected from the group consisting of S, N, O, and can in turn be optionally substituted with, including on the further nitrogen atom, C$_{1-3}$ alkyl, formyl, a 5- or 6-membered heteroaromatic moiety containing 1–3 O, N or S,

in which R$_{88}$ and R$_{89}$ are each independently hydrogen or C$_{1-6}$ alkyl, SO$_2$R$_{90}$ in which R$_{90}$ is H or C$_{1-6}$ alkyl, or C$_{1-3}$ acyl optionally substituted with 1 or more F, Cl or OH;

R$_{19}$ is
a) carboxyl,
b) halo,
c) —CN,
d) mercapto,
e) formyl,
f) CF$_3$,
g) NO$_2$,
h) C$_{1-6}$ alkoxy,
i) C$_{1-6}$ alkoxycarbonyl,
j) C$_{1-6}$ alkythio,
k) C$_{1-6}$ acyl,
i) C$_{1-6}$ alkyl optionally substituted with OH, C$_{1-5}$ alkoxy, C$_{1-5}$ acyl, or —NR$_{17}$R$_{18}$,
m) phenyl,
n) —C(=O)NR$_{20}$R$_{21}$,
o) —N R$_{17}$R$_{18}$,
p) —N(R$_{20}$)(—SO$_2$R$_{22}$),
q) —SO$_2$—NR$_{20}$R$_{21}$, or
r) —S(=O)$_i$R$_{22}$;

R$_{20}$ and R$_{21}$ at each occurrence are the same or different and are
a) H,
b) C$_{1-6}$ alkyl, or
c) phenyl;

R$_{22}$ is
a) C$_{1-4}$ alkyl, or
b) phenyl optionally substituted with C$_{1-4}$ alkyl;

wherein R$_9$ is
a) carboxyl,
b) halo,
c) —CN,
d) mercapto,
e) formyl,
f) CF$_3$,
g) NO$_2$,
h) C$_{1-6}$ alkoxy,
i) C$_{1-6}$ alkoxycarbonyl,
j) C$_{1-6}$ alkythio,
k) C$_{1-6}$ acyl,
l) —NR$_{23}$R$_{24}$,
m) C$_{1-6}$ alkyl optionally substituted with OH, C$_{1-5}$ alkoxy, C$_{1-5}$ acyl, or —NR$_{23}$R$_{24}$,
n) C$_{2-8}$ alkenylphenyl optionally substituted with one or two R$_{25}$,
o) phenyl optionally substituted with one or two R$_{25}$,
p) a 5- or 6-membered saturated or unsaturated heterocyclic moiety having one to three atoms selected from the group consisting of S, N, and O, optionally substituted with one or two R$_{25}$, or q) 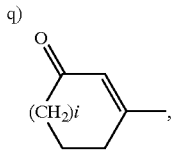

R$_{23}$ and R$_{24}$ at each occurrence are the same or different and are
a) H,
b) formyl,
c) C$_{1-4}$ alkyl,
d) C$_{1-4}$ acyl,
e) phenyl,
f) C$_{3-6}$ cycloalkyl, or
g) R$_{23}$ and R$_{24}$ taken together with the nitrogen atom is a 5- or 6-membered saturated heterocyclic moiety which optionally has a further hetero atom selected from the group consisting of S, N, O, and can in turn be optionally substituted with, including on the further nitrogen atom, phenyl, pyrimidyl, C$_{1-3}$ alkyl, or C$_{1-3}$ acyl;

R$_{25}$ is
a) carboxyl,
b) halo,
c) —CN,
d) mercapto,
e) formyl,
f) CF$_3$,
g) NO$_2$,
h) C$_{1-6}$ alkoxy,
i) C$_{1-6}$ alkoxycarbonyl,
j) C$_{1-6}$ alkythio,
k) C$_{1-6}$ acyl,
i) phenyl, m) $C_{1-6}$ alkyl optionally substituted with OH, azido, $C_{1-5}$ alkoxy, $C_{1-5}$ acyl, —$NR_{32}R_{33}$, —$SR_{34}$, —O—$SO_2R_{35}$, or

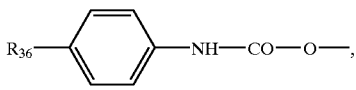

n) —C(=O)$NR_{26}R_{27}$,
o) —$NR_{23}R_{24}$,
p) —N($R_{26}$)(—$SO_2R_{22}$),
q) —$SO_2$—$NR_{26}R_{27}$, or
r) —S(=O)$_iR_{22}$,
s) —CH=N—$R_{28}$, or
t) —CH(OH)—$SO_3R_{31}$;

$R_{22}$ is the same as defined above;

$R_{26}$ and $R_{27}$ at each occurrence are the same or different and are
a) H,
b) $C_{1-6}$ alkyl,
c) phenyl, or
d) tolyl;

$R_{28}$ is
a) OH,
b) benzyloxy,
c) —NH—C(=O)—$NH_2$,
d) —NH—C(=S)—$NH_2$, or
e) —NH—C(=NH)—$NR_{29}R_{30}$;

$R_{29}$ and $R_{30}$ at each occurrence are the same or different and are
a) H, or
b) $C_{1-4}$ alkyl optionally substituted with phenyl or pyridyl;

$R_{31}$ is
a) H, or
b) a sodium ion;

$R_{32}$ and $R_{33}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl,
g) $R_{32}$ and $R_{33}$ taken together are a 5- or 6-membered saturated heterocyclic moiety having one to three atoms selected from the group consisting of S, N, O, optionally substituted with, including on the nitrogen atom, phenyl, pyrimidyl, $C_{1-3}$ alkyl, or $C_{1-3}$ acyl,
h) —P(O)($OR_{37}$)($OR_{38}$), or
i) —$SO_2$—$R_{39}$;

$R_{34}$ is

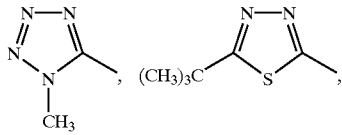

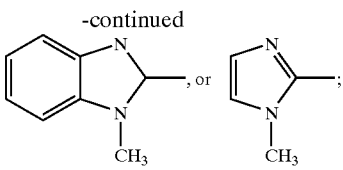

$R_{35}$ is $C_{1-3}$ alkyl;

$R_{36}$ is
a) $C_{1-6}$ alkoxycarbonyl, or
b) carboxyl;

$R_{37}$ and $R_{38}$ at each occurrence are the same or different and are
a) H, or
b) $C_{1-3}$ alkyl;

$R_{39}$ is
a) methyl,
b) phenyl, or
c) tolyl;

wherein K is
a) O,
b) S, or
c) $NR_{40}$ in which $R_{40}$ is hydrogen, formyl, $C_{1-4}$ alkyl, $C_{1-4}$ acyl, phenyl, $C_{3-6}$ cycloalkyl, —P(O)($OR_{37}$)($OR_{38}$) or —$SO_2$—$R_{39}$ in which $R_{37}$, $R_{38}$ and $R_{39}$ are as defined above;

$R_{10}$, $R_{11}$, $R_{12}$, $R_{13}$, $R_{14}$ and $R_{15}$ at each occurrence are the same or different and are
a) H,
b) formyl,
c) carboxyl,
d) $C_{1-6}$ alkoxycarbonyl,
e) $C_{1-8}$ alkyl,
f) $C_{2-8}$ alkenyl,
wherein the substitutents (e) and (f) can be optionally substituted with OH, halo, $C_{1-6}$alkoxyl, $C_{1-6}$acyl, $C_{1-6}$alkylthio or $C_{1-6}$, alkoxycarbonyl, or phenyl optionally substituted with halo,
g) an aromatic moiety having 6 to 10 carbon atoms optionally substituted with carboxyl, halo, —CN, formyl, $CF_3$, $NO_2$, $C_{1-6}$ alkyl, $C_{1-6}$ alkoxy, $C_{1-6}$ acyl, $C_{1-6}$ alkylthio, or $C_{1-6}$ alkoxycarbonyl;
h) —$NR_{42}R_{43}$,
i) $OR_{44}$,
—S(=O)$_i$—$R_{45}$,
k) —$SO_2$—N($R_{46}$)($R_{47}$), or
l) a radical of the following formulas:

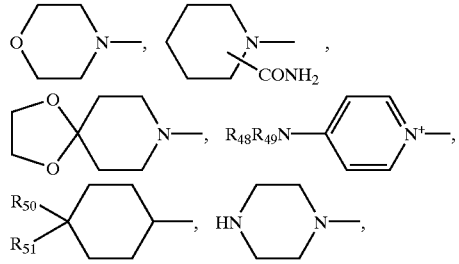

-continued $R_{52}-(CH_2)t-N\underset{(\phantom{x})_j}{\diagup\diagdown}N-$, or $R_{53}-N\underset{R_{53}}{\diagup\diagdown}N-$;

$R_{19}$ is the same as defined above;

T is
  a) O,
  b) S, or
  c) $SO_2$;

$R_{42}$ and $R_{43}$ at each occurrence are the same or different and are
  a) H,
  b) $C_{3-6}$ cycloalkyl,
  c) phenyl,
  d) $C_{1-6}$ acyl,
  e) $C_{1-8}$ alkyl optionally substituted with OH, $C_{1-6}$ alkoxy which can be substituted with OH, a 5- or 6-membered aromatic heterocyclic moiety having one to three atoms selected from the group consisting of S, N, and O, phenyl optionally substituted with OH, $CF_3$, halo, —$NO_2$, $C_{1-4}$ alkoxy,—$NR_{48}R_{49}$, or

[structure: benzodioxole], f)

$R_{55}-CH\underset{\phantom{x}}{\overset{O}{\diagdown}}R_{54}$, or g) [structure: V—N—(CH₂)t—];

V is
  a) O,
  b) $CH_2$, or
  c) $NR_{56}$;

$R_{48}$ and $R_{49}$ at each occurrence are the same or different and are
  a) H, or
  b) $C_{1-4}$ alkyl;

$R_{54}$ is
  a) OH,
  b) $C_{1-4}$ alkoxy, or
  c) —$NR_{57}R_{58}$;

$R_{55}$ is
  a) H, or
  b) $C_{1-7}$ alkyl optionally substituted with indolyl, OH, mercaptyl, imidazoly, methylthio, amino, phenyl optionally substituted with OH, —C(=O)—$NH_2$, —$CO_2H$, or —C(=NH)—$NH_2$;

$R_{56}$ is
  a) H,
  b) phenyl, or
  c) $C_{1-6}$ alkyl optionally substituted by OH;

$R_{57}$ and $R_{58}$ at each occurrence are the same or different and are
  a) H,
  b) $C_{1-5}$ alkyl,
  c) $C_{1-3}$ cycloalkyl, or
  d) phenyl;

$R_{44}$ is
  a) $C_{1-8}$ alkyl optionally substituted with $C_{1-6}$ alkoxy or $C_{1-6}$ hydroxy, $C_{3-6}$ cycloalkyl, a 6-membered aromatic optionally benzo-fused heterocyclic moiety having one to three nitrogen atoms, which can in turn be substituted with one or two —$NO_2$, $CF_3$, halo, —CN, OH, $C_{1-5}$ alkyl, $C_{1-5}$ alkoxy, or $C_{1-5}$ acyl, b)

[structure: V—N—(CH₂)t—], c) phenyl, or
  d) pyridyl;

$R_{45}$ is
  a) $C_{1-16}$ alkyl,
  b) $C_{2-16}$ alkenyl,
  wherein the substituents (a) and (b) can be optionally substituted with $C_{1-6}$ alkoxycarbonyl, or a 5-, 6-, or 7-membered aromatic heterocyclic moiety having one to three atoms selected from the group consisting of S, N, and O,
  c) an aromatic moiety having 6 to 10 carbon atoms, or
  d) a 5-, 6-, or 7-membered aromatic heterocyclic moiety having one to three atoms selected from the group of S, N, and O, wherein the substituents (c) and (d) can be optionally substituted with carboxyl, halo, —CN, formyl, $CF_3$, —$NO_2$, $C_{1-6}$ alkyl, $C_{1-6}$ alkoxy, $C_{1-6}$ acyl, $C_{1-6}$ alkylthio, or $C_{1-6}$ alkoxycarbonyl;

$R_{46}$ and $R_{47}$ at each occurrence are the same or different and are
  a) H,
  b) phenyl,
  c) $C_{1-6}$ alkyl, or
  d) benzyl;

$R_{50}$ and $R_{51}$ at each occurrence are the same or different and are
  a) H,
  b) OH,
  c) $C_{1-6}$ alkyl optionally substituted with —$NR_{48}R_{49}$ in which $R_{48}$ and $R_{49}$ are as defined above,
  d) $R_{50}$ and $R_{51}$ taken together are =O;

$R_{52}$ is
  a) an aromatic moiety having 6 to 10 carbon atoms,
  b) a 5- or 6-membered aromatic optionally benzo-fused heterocyclic moiety having one to three atoms selected from the group consisting of S, N, and O, wherein the substituents (a) and (b) can in turn be optionally substituted with one or three —$NO_2$, $CF_3$, halo, —CN, OH, phenyl, $C_{1-5}$ alkyl, $C_{1-5}$ alkoxy, or $C_{1-5}$ acyl,
  c) morpholinyl,
  d) OH,
  e) $C_{1-6}$ alkoxy,
  f) —$NR_{48}R_{49}$ in which $R_{48}$ and $R_{49}$ are as defined above, g) —C(=O)—$R_{59}$, or h) 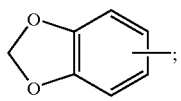;

$R_{53}$ is
  a) H,
  b) formyl,
  c) $C_{1-4}$ alkyl,
  d) $C_{1-4}$ acyl,
  e) phenyl,
  f) $C_{3-6}$ cycloalkyl,
  g) —P(O)(OR$_{37}$)(OR$_{38}$), or
  h) —SO$_2$R$_{39}$, in which $R_{37}$, $R_{38}$ and $R_{39}$ are as defined above;

$R_{59}$ is
  a) morpholinyl,
  b) OH, or
  c) $C_{1-6}$ alkoxy;

h is 1, 2, or 3;
i is 0, 1, or 2;
j is 0, or 1;
k is 3, 4, or 5;
r is 1, 2, 3, 4, 5 or 6;
t is 0, 1, 2, 3, 4, 5, or 6;
u is 1 or 2; and Q is
  a) hydrogen,
  b) halo,
  c) NO$_2$,
  d) N$_3$,
  e) $C_1$–$C_6$ alkylthio, f) 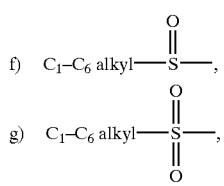, g) 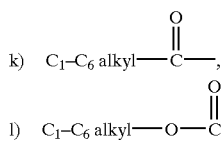, h) $C_1$–$C_6$ alkyl,
  i) $C_1$–$C_6$ alkoxy,
  j) formyl, k) 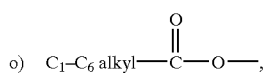, l) $C_1$–$C_6$ alkyl—O—C(=O)—, m) —sulfamoyl (H$_2$NSO$_2$-),
  n) —NHOH, o) $C_1$–$C_6$ alkyl—C(=O)—O—, -continued p) heteroaryl—C(=O)— 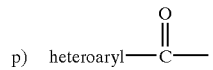

in which heteroaryl is a 5- or 6-membered aromatic heterocyclic group having 1–3 hetero atoms selected from O, N or S, q) C$_6$H$_5$—C(=O)—, 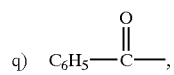

r) amino,
s) $C_1$–$C_6$ alkylamino-,
t) di ($C_1$–$C_6$ alkyl)amino-, u) ($C_1$–$C_6$) alkyl—C(=O)—NR$_{60}$R$_{61}$ 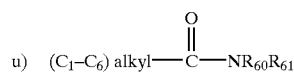

in which $R_{60}$ and $R_{61}$ are each independently hydrogen or $C_1$–$C_6$ alkyl,
v) OH,
w) cyano,
x) hydroxy ($C_1$–$C_6$ alkyl), y) $C_1$–$C_6$ alkyl—S—C(=O)—, 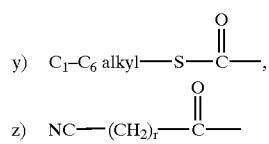

z) NC—(CH$_2$)$_r$—C(=O)— in which r is 1–6, aa) C$_6$H$_5$CH$_2$—O—C(=O)—, 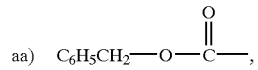

bb) C$_6$H$_5$—O—C(=O)—, 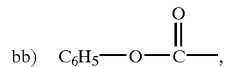

cc) $C_1$–$C_6$ alkyl—C(=N—OR$_{84}$)— 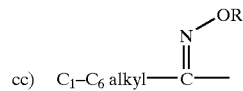

in which $R_{84}$ is hydrogen or $C_{1-6}$ alkyl, dd) R$_{85}$O—(CH$_2$)$_{1-6}$—C(=O)— 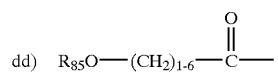

in which $R_{85}$ is hydrogen, $C_{1-8}$ alkyl optionally substituted with one or more F, Cl, OH, $C_{1-8}$ alkoxy or $C_{1-8}$ acyloxy, $C_{3-6}$ cycloalkyl or $C_{1-8}$ alkoxy;

ee) H—C(=N—OR$_{84}$)— 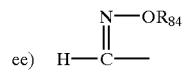

in which $R_{84}$ is hydrogen or $C_{1-6}$ alkyl,
ff) a substituted or unsubstituted $C_6$–$C_{10}$ aryl moiety,
gg) a substituted or unsubstituted monocyclic or bicyclic, saturated or unsaturated, heterocyclic moiety having 1–3 atoms selected from O, N or S, said ring being bonded via a ring carbon or nitrogen to the phenyl substituent, hh) a monocyclic or bicyclic substituted or unsubstituted heteroaromatic moiety having 1–3 hetero atoms selected from O, N or S, said ring being bonded via a ring carbon or nitrogen to the phenyl substituent and wherein the heteroaromatic moiety can additionally have a fused-on benzene or naphthalene ring;

the substituents for such p, q, ff, gg and hh moieties being selected from 1 or 2 of the following:
1) halo,
2) $C_{1-6}$ alkyl,
3) $NO_2$,
4) $N_3$, 5) 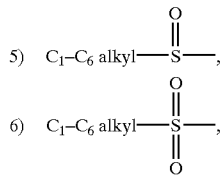

6)

7) formyl,

8) 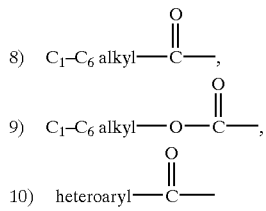

9)

10) heteroaryl—C(=O)— in which heteroaryl is a 5- or 6-membered aromatic heterocyclic group having 1–3 hetero atoms selected from O, N or S, 11) 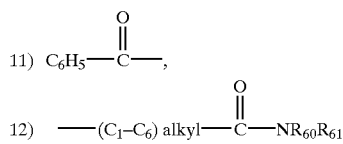

12) —($C_1$–$C_6$) alkyl—C(=O)—$NR_{60}R_{61}$ in which $R_{60}$ and $R_{61}$ are each independently hydrogen or $C_1$–$C_6$ alkyl,
13) OH,
14) hydroxy ($C_1$–$C_6$ alkyl), 15) 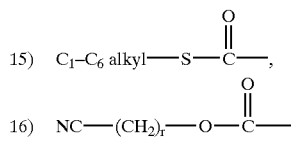

16) NC—$(CH_2)_r$—O—C(=O)— in which r is 1–6,

17) 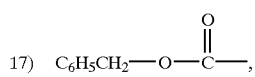

18) —$CH_2$—$R_{80}$ in which $R_{80}$ is
  a) —$OR_{32}$ in which $R_{32}$ is as defined above,
  b) —$SR_{32}$ in which $R_{32}$ is as defined above,
  c) —$NR_{32}R_{33}$ in which $R_{32}$ and $R_{33}$ are as defined above, or
  d) 5- or 6-membered heteroaromatic containing 1–4 O, S or N atoms, 19) 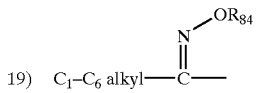

in which $R_{84}$ is as defined above,
20) cyano,
21) carboxyl,
22) $CF_3$,

23) 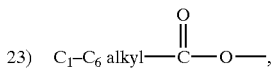

24) 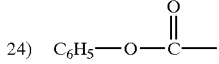

in which the phenyl moiety may be optionally substituted by halo or $(C_1$–$C_6)$alkyl, 25) 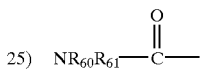

in which $R_{60}$ and $R_{61}$ are as defined above,

26) 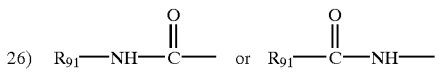

in which $R_{91}$ is a 5- or 6-membered aromatic heterocyclic group having 1–3 O, N or S, 27) 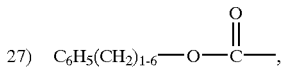

28) 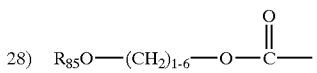

in which $R_{85}$ is as defined above,

29) 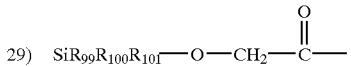

in which $R_{99}$, $R_{100}$ and $R_{101}$ are each independently $C_{1-6}$ alkyl; or Q and either $R_1$ and $R_2$ taken together form —O—$CH_2$—O.

The compounds of this invention are novel and represent a new class of antibacterial agents. They are distinct from both the previously reported oxazolidinone and isoxazoline antibiotics since they incorporate the isoxazolinone ring system. They differ from the prior art isoxazolinone herbicides since the ring nitrogen must be substituted with an amide moiety as defined above.

The compounds of formula I are antibacterial agents useful in the treatment of infections in humans and other animals caused by a variety of bacteria, particularly methicillin-resistant *Staphylococcus aureus* and vancomycin-resistant *Enterococcus faecium.*

Also included in the invention are processes for preparing the compounds of formula I and pharmaceutical compositions containing said compounds in combination with pharmaceutically acceptable carriers or diluents.

DEFINITIONS

The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. These salts may be in hydrated form.

The terms "halo" or "halogen" includes chloro, bromo, fluoro and iodo, and is preferably chloro or fluoro.

The aliphatic "alkyl" groups as used herein means straight or branched chains having the specified number of carbon atoms, e.g. in the case of $C_1$–$C_6$ alkyl, the alkyl group may have from 1 to 6 carbon atoms.

Similarly, terms such as "$C_2$–$C_8$ alkenyl" refer to at least one double bond alkenyl group having the specified number of carbon atoms, "$C_2$–$C_8$ alkenyl" refers to at least one triple bond alkynyl group having the specified number of carbons, etc.

The term "acyloxy" unless otherwise defined refers to a group of the type

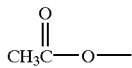

where the alkyl group can have the specified number of carbon atoms, e.g. $C_1$–$C_6$ alkoxy would have 1–6 carbons. Where not specified the carbon length is from 1–6 carbons, Unless otherwise indicated the term "aryl" refers to aromatic carbocyclic rings, i.e. phenyl and naphthyl.

"Heteroaromatic" as used herein refers to an aromatic heterocyclic moiety having one or more atoms selected from O, N, S, e.g. pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyn, 3-quinolyn, 1-isoquinolyl, 3-isoquinolyl, 2-imadazolyl, 4-imadazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-thiazol-3-yl, 1,2,4-thiazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 1-purinyl, 3-isothiazolyl, 4-isothiazolyl, and 5-isothiazolyl.

A saturated or unsaturated heterocyclic group can have 1–3 atoms selected from O, N and S, e.g. dioxolane, imidazolidine, dithiolane, oxathiolane, oxazolidine, piperidinyl, piperazinyl, morpholino or thiomorpholino, or the corresponding unsaturated heterocyclic groups.

Where possible nitrogen and/or sulfur atoms in such heterocyclic moieties may be oxidized and such oxidized compounds are intened to be encompassed within the formula I compounds.

DETAILED DESCRIPTION

Preferred embodiments of the present invention are the compounds of formula I wherein A is

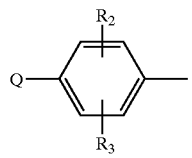

in which $Q_1$, $R_2$, and $R_3$ are as defined above.

A still more preferred embodiment of the present invention comprises a compound of the formula

IA

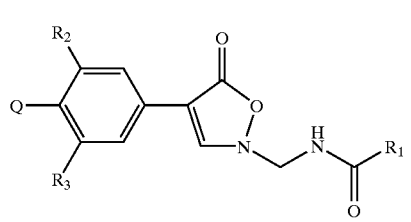

or a pharmaceutically acceptable salt thereof, in which $R_1$ is H, $C_{1-8}$ alkyl optionally substituted with one or more F, Cl, OH, $C_{1-8}$ alkoxy, or $C_{1-8}$ acyloxy, $C_{3-6}$ cycloalkyl or $C_{1-8}$ alkoxy;

$R_2$ and $R_3$ are each independently
a) H,
b) F,
c) Cl,
d) Br,
e) $C_{1-6}$ alkyl,
f) $NO_2$,
g) I,
h) $C_{1-6}$ alkoxy,
i) OH
j) amino, or
k) cyano; and Q is
a) hydrogen,
b) halo,
c) $NO_2$,
d) $N_3$,
e) $C_1$–$C_6$ alkylthio, f) 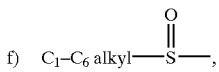

g) 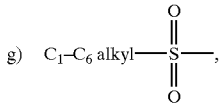

h) $C_1$–$C_6$ alkyl,
i) $C_1$–$C_6$ alkoxy,
j) formyl, k) 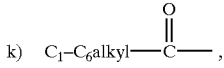

-continued l) $C_1$–$C_6$alkyl—O—C(=O)—, m) $C_1$–$C_6$alkyl—C(=O)—O—, n) heteroaryl—C(=O)— in which heteroaryl is a 5- or 6-membered aromatic heterocyclic group having 1–3 hetero atoms selected from O, N or S, o) $C_6H_5$—C(=O)—, p) amino,
q) $C_1$–$C_6$ alkylamino-,
r) di($C_1$–$C_6$ alkyl)amino-, s) ($C_1$–$C_6$) alkyl—C(=O)—$NR_{60}R_{61}$, in which $R_{60}$ and $R_{61}$ are each independently hydrogen or $C_1$–$C_6$ alkyl,
t) OH,
u) cyano,
v) hydroxy ($C_1$–$C_6$ alkyl), w) $C_1$–$C_6$alkyl—S—C(=O)—, x) NC—$(CH_2)_r$—O—C(=O)— in which r is 1–6, y) $C_6H_5CH_2$—O—C(=O)—, z) $C_6H_5$—O—C(=O)—, aa) $C_1$–$C_6$alkyl—C(=N—$OR_{84}$)— wherein $R_{84}$ is hydrogen or $C_{1-6}$ alkyl, bb) $R_{85}O$—$(CH_2)_{1-6}$—C(=O)— in which $R_{85}$ is hydrogen, $C_{1-8}$ alkyl optionally substituted with one or more F, Cl, OH, $C_{1-8}$ alkoxy or $C_{1-8}$ acyloxy, $C_{3-6}$ cycloalkyl or $C_{1-8}$ alkoxy, cc) H—C(=N—$OR_{84}$)— which $R_{84}$ is as defined above, dd) 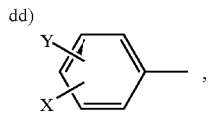

ee) 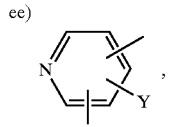

ff) 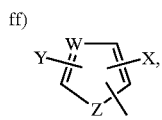

gg) 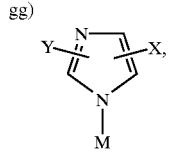

hh) 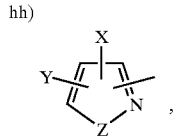

ii) 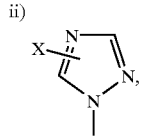

jj) 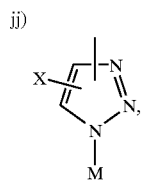

kk) 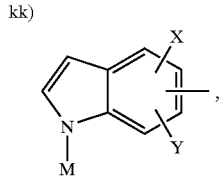

ll) 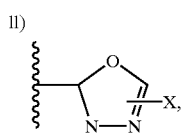

mm) 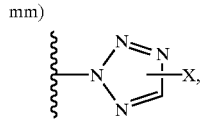

nn) 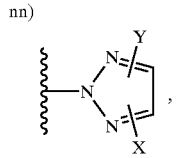

-continued oo) 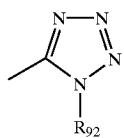

in which R$_{92}$ is H or C$_{1-6}$ alkyl, pp) 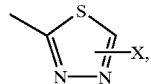

qq) 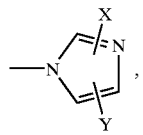

rr) 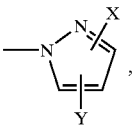

ss) 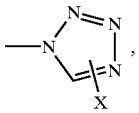

tt) 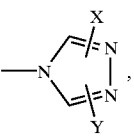

uu) 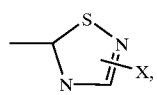

vv) 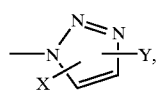

ww) 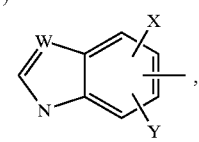

xx) 

yy) 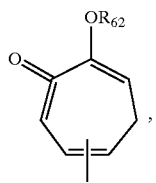

-continued zz) 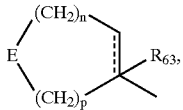

aaa) a diazinyl group optionally substituted with X and Y,
bbb) a tiazinyl group optionally substituted with X and Y,
ccc) a quinolinyl group optionally substituted with X and Y,
ddd) a quinoxalinyl group optionally substituted with X and Y,
eee) a naphthyridinyl group optionally substituted with X and Y, fff) 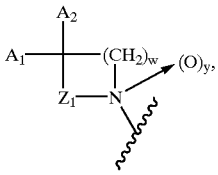

ggg) 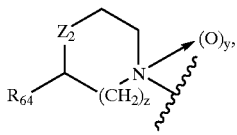

hhh) 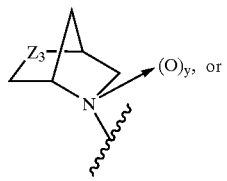

iii) 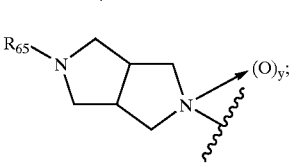

B is an unsaturated 4-atom linker having one nitrogen and three carbons;
M is
  a) H,
  b) C$_{1-8}$ alkyl,
  c) C$_{3-8}$ cycloalkyl,
  d) —(CH$_2$)$_m$OR$_{66}$, or
  e) —(CH$_2$)$_n$NR$_{67}$R$_{68}$;
Z is
  a) O,
  b) S or
  c) NM;
W is
  a) CH,
  b) N or
  c) S or O when Z is NM;
X and Y are each independently
  a) hydrogen,
  b) halo, c) $NO_2$,
d) $N_3$,
e) $C_{1-6}$ alkythio,

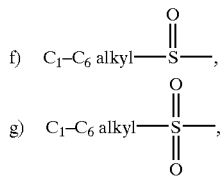

f) $C_1$–$C_6$ alkyl—S(=O)—, g) $C_1$–$C_6$ alkyl—S(=O)_2—, h) $C_1$–$C_6$ alkyl,
i) $C_1$–$C_6$ alkoxy,
j) formyl,

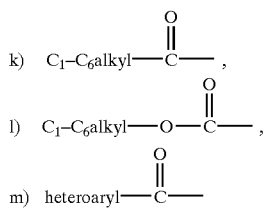

k) $C_1$–$C_6$alkyl—C(=O)—, l) $C_1$–$C_6$alkyl—O—C(=O)—, m) heteroaryl—C(=O)— in which heteroaryl is a 5- or 6-membered aromatic heterocyclic group having 1–3 hetero atoms selected from O, N or S.

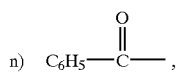

n) $C_6H_5$—C(=O)—, o) amino,
p) $C_1$–$C_6$ alkylamino-,
q) di($C_1$–$C_6$ alkyl)amino-,

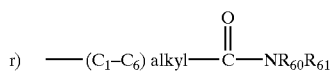

r) —($C_1$–$C_6$) alkyl—C(=O)—$NR_{60}R_{61}$ in which $R_{60}$ and $R_{61}$ are each independently hydrogen or $C_1$–$C_6$ alkyl,
s) OH,
t) hydroxy ($C_1$–$C_6$ alkyl),

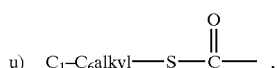

u) $C_1$–$C_6$alkyl—S—C(=O)—,

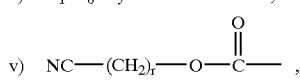

v) NC—$(CH_2)_r$—O—C(=O)—, in which r is 1–6,

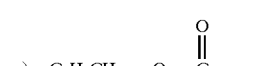

w) $C_6H_5CH_2$—O—C(=O)—,

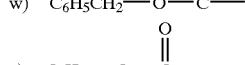

x) $C_6H_5$—O—C(=O)—,

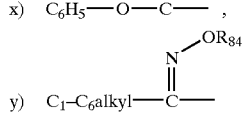

y) $C_1$–$C_6$alkyl—C(=N—$OR_{84}$)— in which $R_{84}$ is as defined above,
z) cyano, aa) carboxyl,
bb) $CF_3$,
cc) mercapto,

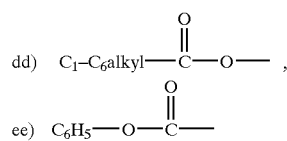

dd) $C_1$–$C_6$alkyl—C(=O)—O—, ee) $C_6H_5$—O—C(=O)— in which the phenyl moiety may be optionally substituted by halo or $C_1$–$C_6$ alkyl,

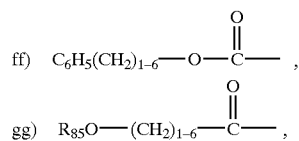

ff) $C_6H_5(CH_2)_{1-6}$—O—C(=O)—, gg) $R_{85}O$—$(CH_2)_{1-6}$—C(=O)—, in which $R_{85}$ is as defined above, or

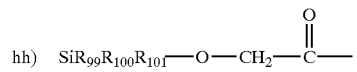

hh) $SiR_{99}R_{100}R_{101}$—O—$CH_2$—C(=O)— in which $R_{99}$, $R_{100}$ and $R_{101}$ are each independently $C_{1-6}$ alkyl; or Q and either $R_1$ and $R_3$ taken together form —O—$CH_2$—O;

$R_{62}$ is
a) H,
b) $C_{1-8}$ alkyl optionally substituted with one or more halos, or
c) $C_{1-8}$ alkyl optionally substituted with one or more OH, or $C_{1-8}$ alkoxy;

E is
a) $NR_{69}$,
b) —S(=O)$_i$ in which i is 0, 1 or 2, or
c) O;

$R_{63}$ is
a) H,
b) $C_{1-6}$alkyl,
c) —$(CH_2)_q$-aryl, or
d) halo;

$R_{66}$ is H or $C_{1-4}$ alkyl;

$R_{67}$ and $R_{68}$ are each independently H or $C_{1-4}$ alkyl, or $NR_{67}R_{68}$ taken together are —$(CH_2)_m$—;

$R_{69}$ is
a) H,
b) $C_{1-6}$ alkyl,
c) —$(CH_2)_q$—aryl,
d) —$CO_2R_{81}$,
e) $COR_{82}$,
f) —C(=O)—$(CH_2)_q$—C(=O)$R_{81}$,
g) —S(=O)$_z$—$C_{1-6}$ alkyl,
h) —S(=O)$_z$—$(CH_2)_q$—aryl, or
i) —(C=O)$_j$—Het in which j is 0 or 1;

$Z_1$ is
a) —$CH_2$—, or
b) —CH($R_{70}$)—$CH_2$—;

$Z_2$ is
a) —$O_2S$—,
b) —O—,
c) —S—, d) —SO—, or
e) —N($R_{71}$)—;

$Z_3$ is
a) S,
b) SO,
c) $SO_2$, or
d) O;

$A_1$ is H or $CH_3$;

$A_2$ is
a) H,
b) OH—,
C) $CH_3CO_2$—,
d) $CH_3$—,
e) $CH_3O$—,
f) $R_{72}O$—$CH_2$—C(O)—NH—,
g) $R_{73}O$ —C(O)—NH—,
h) $R_{73}$—C(O)—NH—,
i) ($C_1$–$C_2$)alkyl-O—C(O)—, or
j) HO—$CH_2$; or $A_1$ and $A_2$ taken together are a)

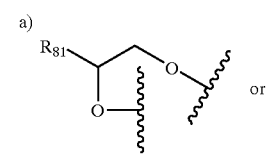 or b) O=;

$R_{64}$ is H or $CH_3$—;
m is 4 or 5;
n is 0, 1, 2, 3, 4 or 5;
y is 0 or 1;
p is 0, 1, 2, 3, 4 or 5;
w is 1, 2 or 3;
q is 1, 2, 3 or 4;
z is 0 or 1;

$R_{65}$ is
a) $R_{74}OC(R_{75})(R_{76})$—C(O)—,
b) $R_{77}OC(O)$—,
c) $R_{78}(O)$—,
d) $R_{79}$—$SO_2$—, or
e) $R_{80}$—NH—C(O)—;

$R_{70}$ is H or ($C_1$–$C_3$)alkyl;

$R_{71}$ is
a) $R_{74}OC(R_{75})(R_{76})$—C(O)—,
b) $R_{77}O$—C(O)—,
c) $R_{78}$—C(O)—, d)
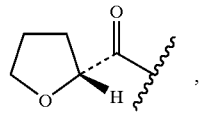, e)
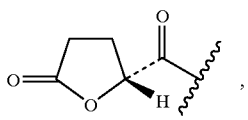, f) $H_3C$–C(O)–($CH_2$)$_2$—C(O)—, g) $R_{79}$—$SO_2$—, h)
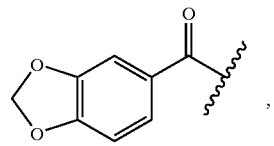, i) $R_{80}$—NH—C(O)—, $R_{72}$ is
a) H.
b) $CH_3$,
c) phenyl —$CH_2$—, or
d) $CH_3C(O)$—;

$R_{73}$ is ($C_1$–$C_3$)alkyl or phenyl;

$R_{74}$ is H, $CH_3$, phenyl-$CH_2$— or $CH_3$—C(O)—;

$R_{75}$ and $R_{76}$ are each independently H or $CH_3$, or $R_{75}$ and $R_{76}$ taken together are —$CH_2CH_2$—;

$R_{77}$ is ($C_1$–$C_3$)alkyl or phenyl;

$R_{78}$ is H, ($C_1$–$C_4$)alkyl, aryl-($CH_2$)$_{n^1}$, $ClH_2C$, $Cl_2HC$, $FH_2C$—, $F_2HC$— or ($C_3$–$C_6$)cycloalkyl;

$R_{79}$ is $CH_3$; —$CH_2Cl$, —$CH_2CH=CH_2$, aryl or —$CH_2CN$;

$R_{80}$ is $CH_2$)$_{n^1}$-aryl where $n^1$ is 0 or 1;

$R_{81}$ is
a) H,
b) $C_{1-6}$ alkyl optionally substituted with one or more OH, halo or CN,
c) —($CH_2$)$_q$-aryl in which q is as defined above, or
d) —($CH_2$)$_q$—$OR_{83}$ in which q is as defined above;

$R_{82}$ is
a) $C_{1-6}$ alkyl optionally substituted with one or more OH, halo or CN,
b) —($CH_2$)$_q$-aryl in which q is as defined above, or
c) —($CH_2$)$_q$—$OR_{83}$ in which q is as defined above;

$R_{83}$ is
a) H,
b) $C_{1-6}$ alkyl,
c) —($CH_2$)$_q$-aryl in which q is as defined above; or
d) —C(=O) $C_{1-6}$ alkyl; and aryl is phenyl, pyridyl or naphthyl, said phenyl, pyridyl or naphthyl moieties being optionally substituted by one or more halo, —CN, OH, SH, $C_{1-6}$ alkoxy or $C_{1-6}$ alkylthio.

Another preferred embodiment of the present invention comprises a compound of the formula

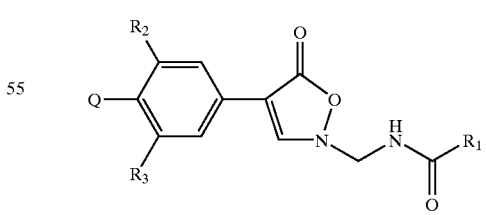

IA or a pharmaceutically acceptable salt thereof, in which
$R_1$ is H, $C_{1-8}$ alkyl optionally substituted with one or more F, Cl, OH, $C_{1-8}$ alkoxy or $C_{1-8}$ acyloxy, $C_{3-6}$ cycloalkyl or $C_{1-8}$ alkoxy;

$R_2$ and $R_3$ are each independently H or F; or $R_2$ and $R_3$ taken together represent

a) hydrogen,
b) halo,
c) $N_3$,
d) $NO_2$,
e) $C_1$–$C_6$ alkylthio,

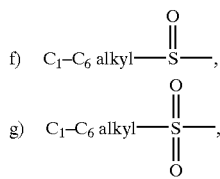

h) $C_1$–$C_6$ alkyl,
i) $C_1$–$C_6$ alkoxy,
j) formyl,

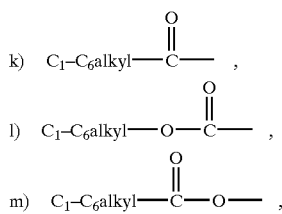

n) $(C_1$—$C_6$ alkoxy$)_2$N—,
o) 5- or 6-membered heterocyclic containing 1–3 O, N or S and linked to the phenyl substituent via a carbon or nitrogen, said heterocycle moiety being optionally substituted by $R_{96}$,

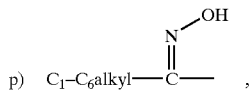

q) phenyl optionally substituted by $R_{96}$, or
r) 5- or 6-membered saturated or unsaturated heterocyclic containing 1–3 O, N or S and linked to the phenyl substituent via a carbon or nitrogen, said heterocycle moiety being optionally substituted by $R_{96}$, and $R_{96}$ is a) $C_1$–$C_6$ alkyl-OH, b) 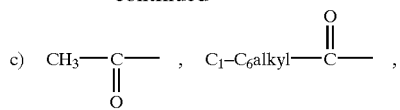

-continued

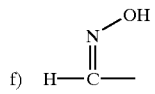

d) cyano,
e) formyl,

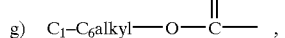

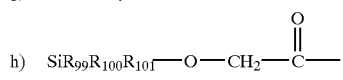

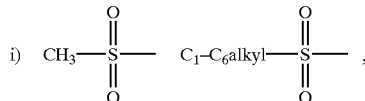

in which $R_{99}$, $R_{100}$ and $R_{101}$, are each independently $C_{1-6}$ alkyl,

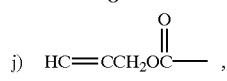

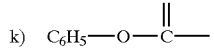

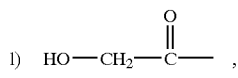

where the phenyl may be optionally substituted by halo,

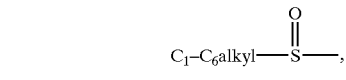

m) $(C_1$–$C_6$ alkyl$)_2$N—,
n) $C_1$–$C_6$ alkyl-NH—,
o) amino, p) 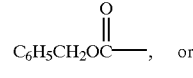

q) 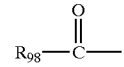

in which $R_{98}$ is phenyl, 5- or 6-membered heteroaryl containing 1–3 O, N or S and linked to the phenyl substituent via a ring carbon atom or 5- or 6-membered saturated or unsaturated heterocyclic containing 1-4 O, N or S and linked to the phenyl substituent via a ring carbon atom.

Some specific preferred embodiments of the present invention are listed in the table below.

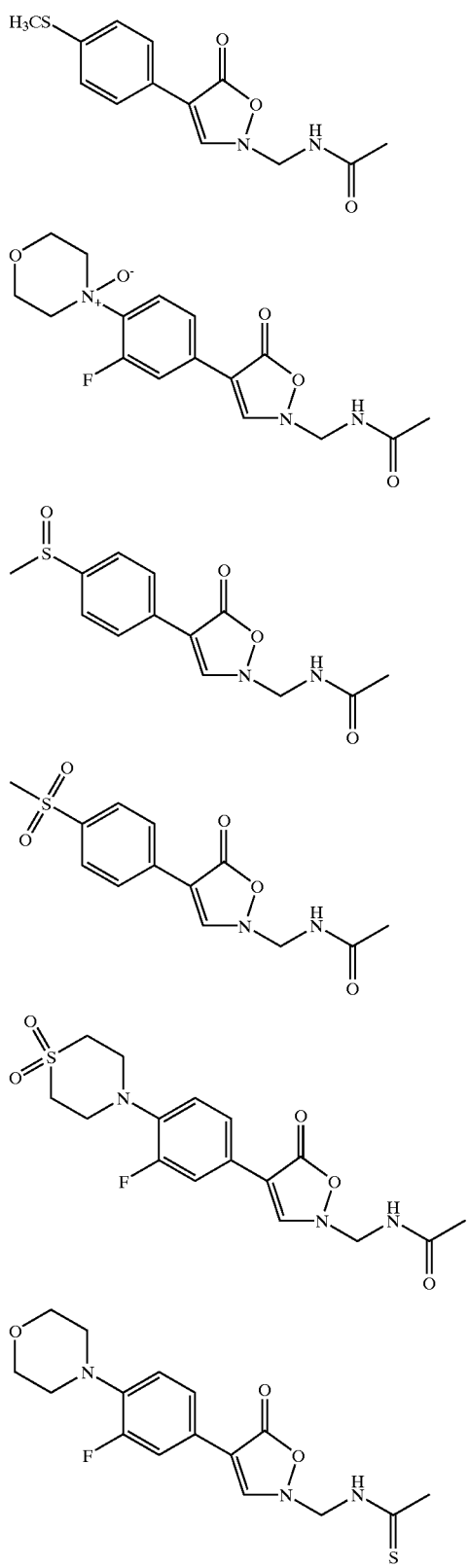
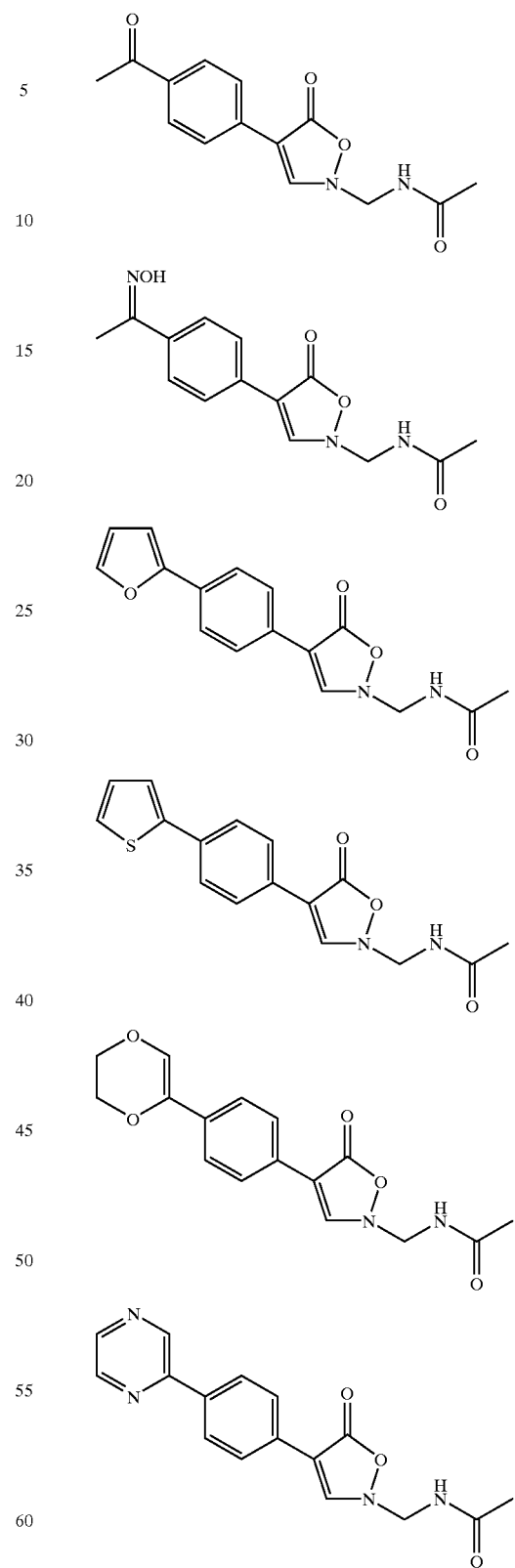

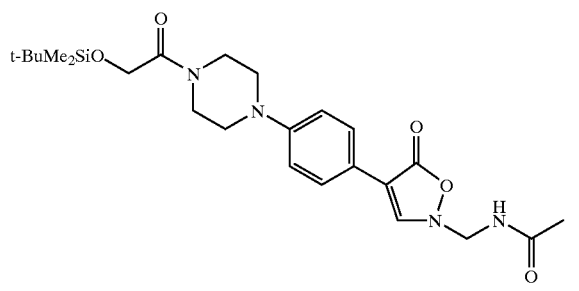
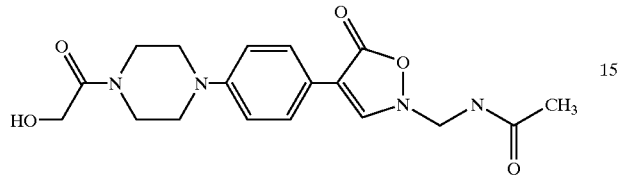
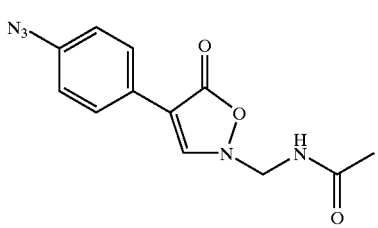
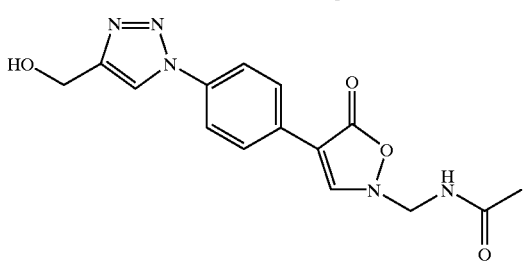
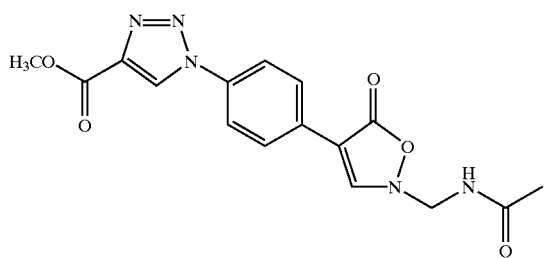
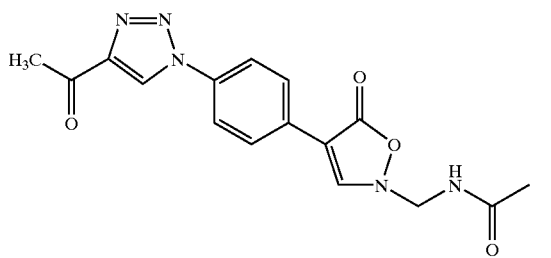
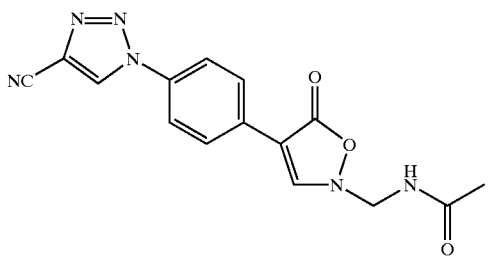
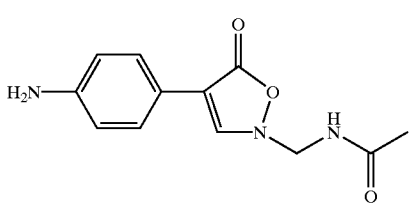
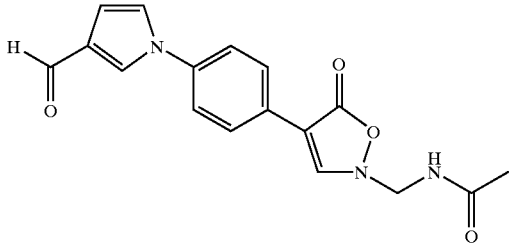
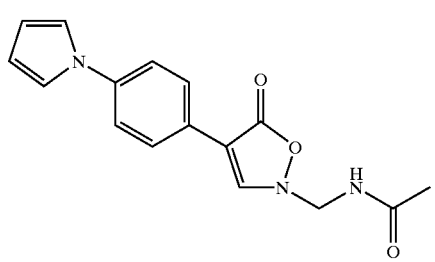
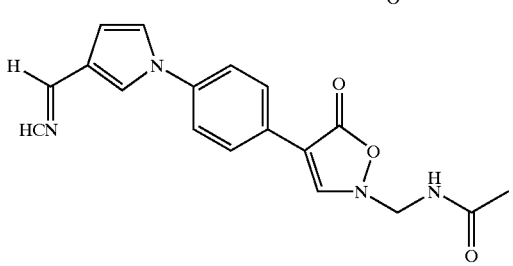
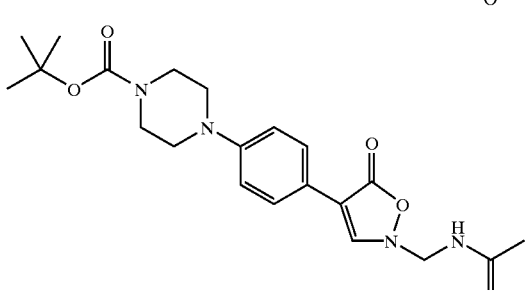
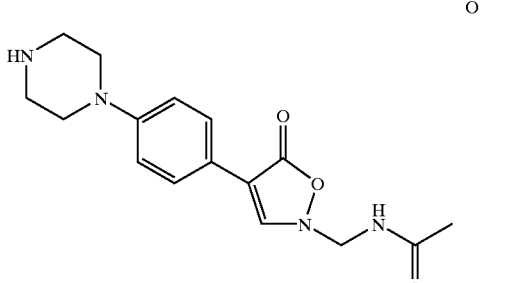
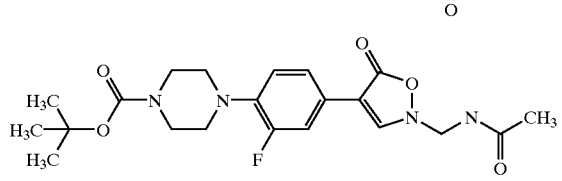

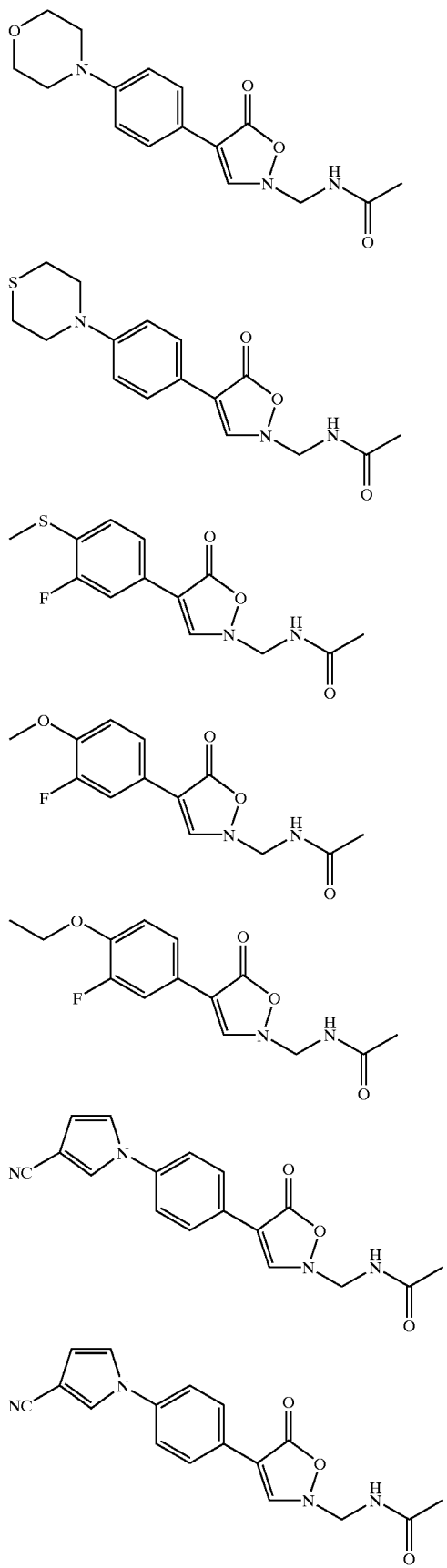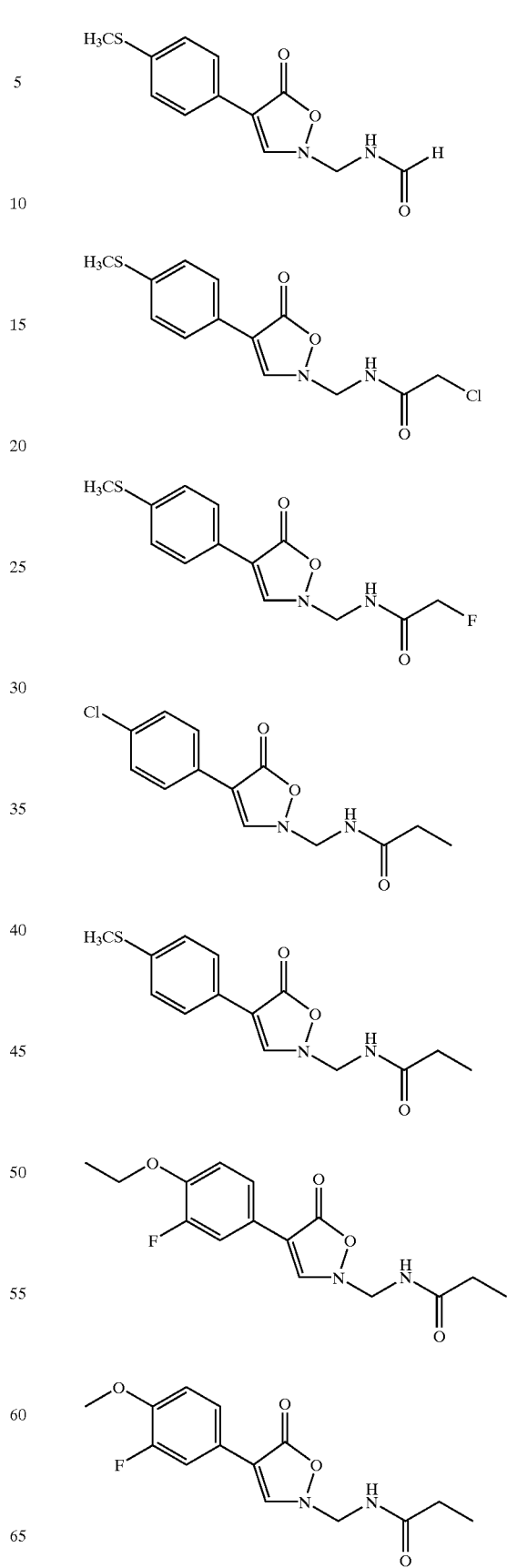

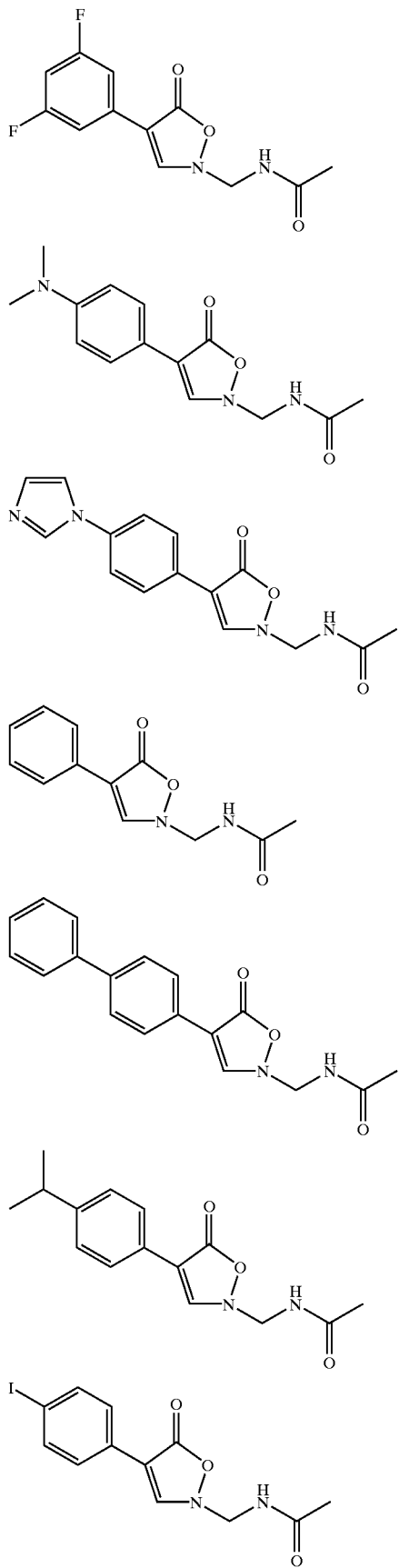
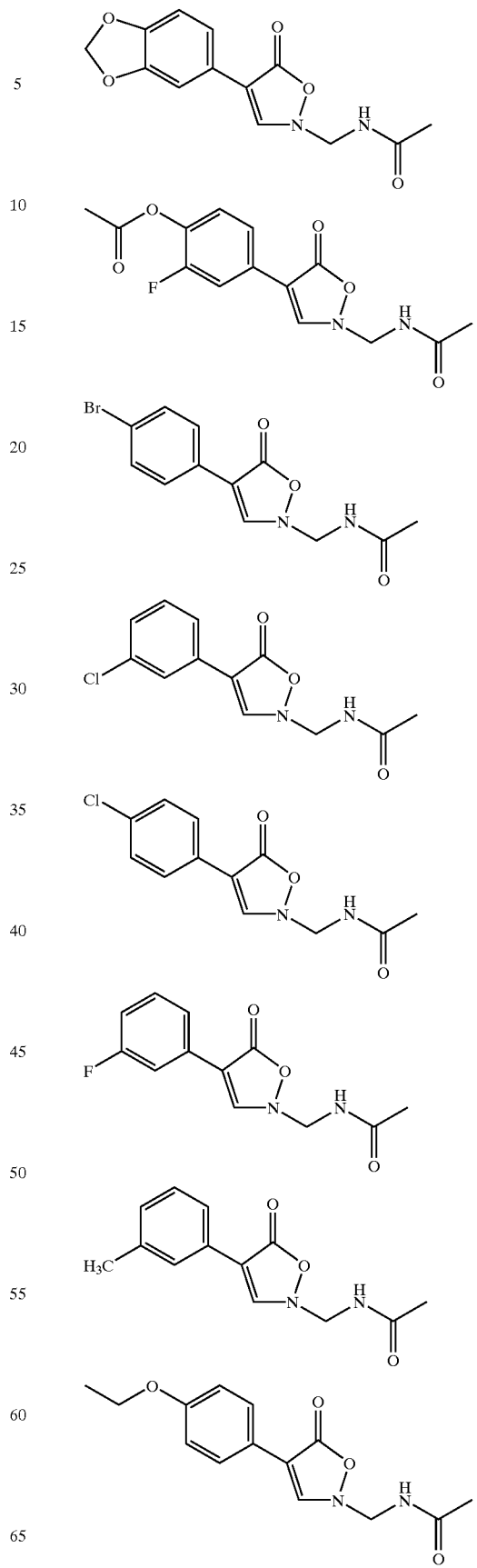

-continued
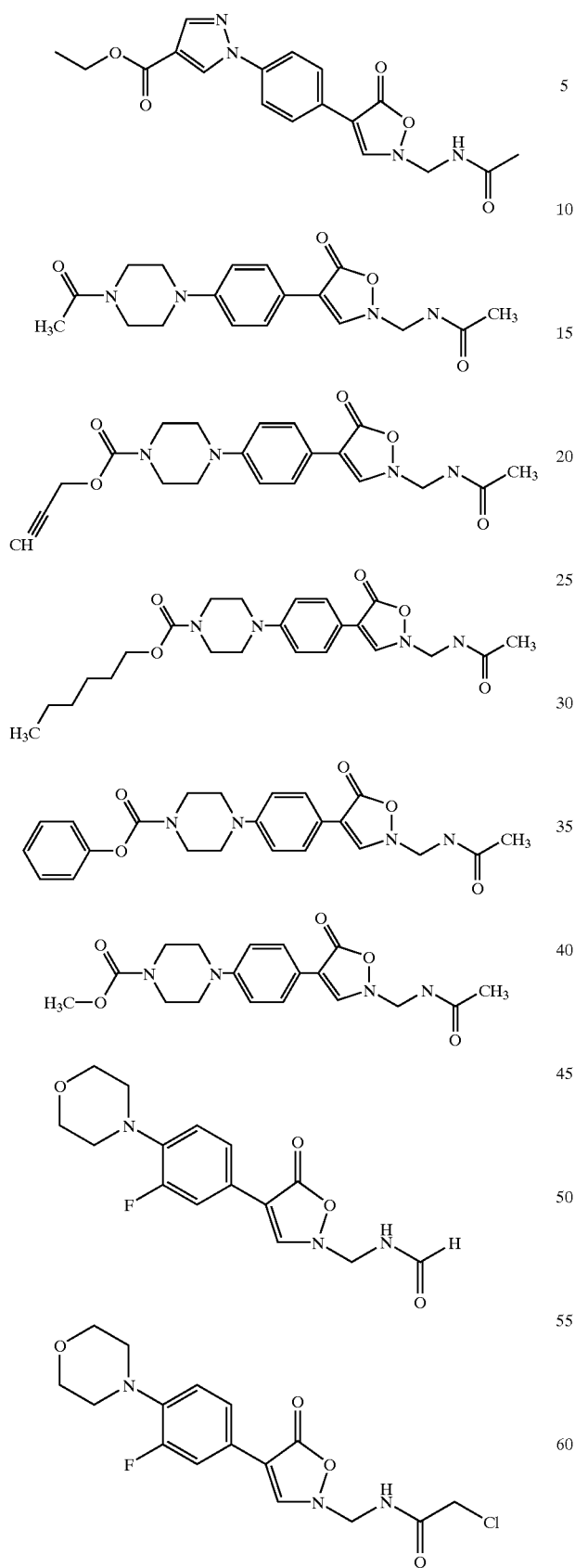
-continued
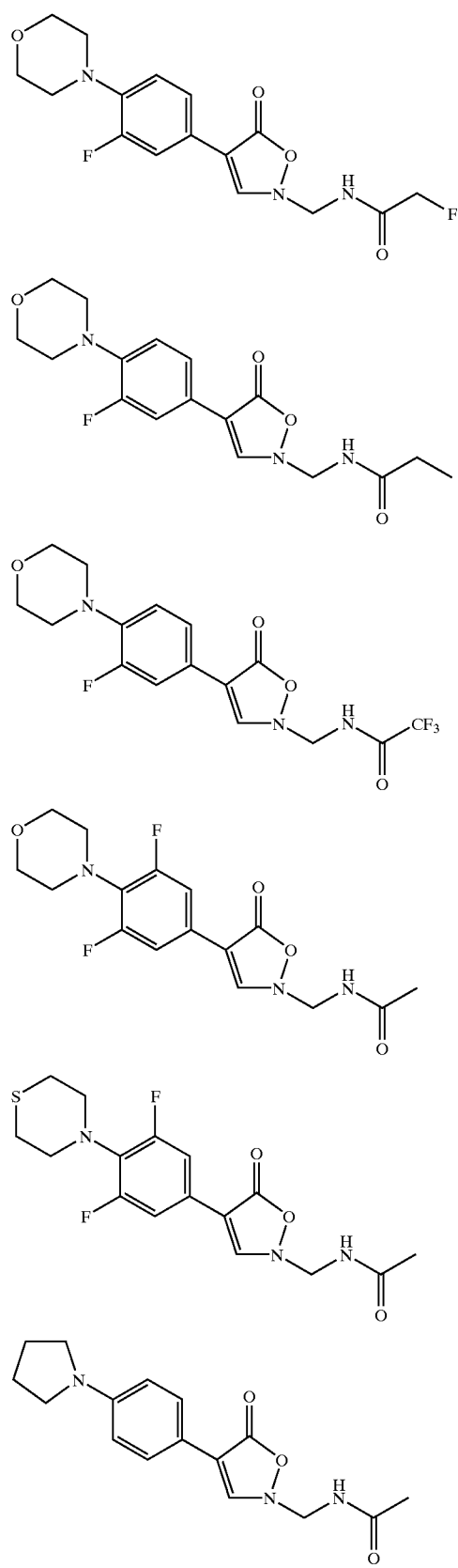

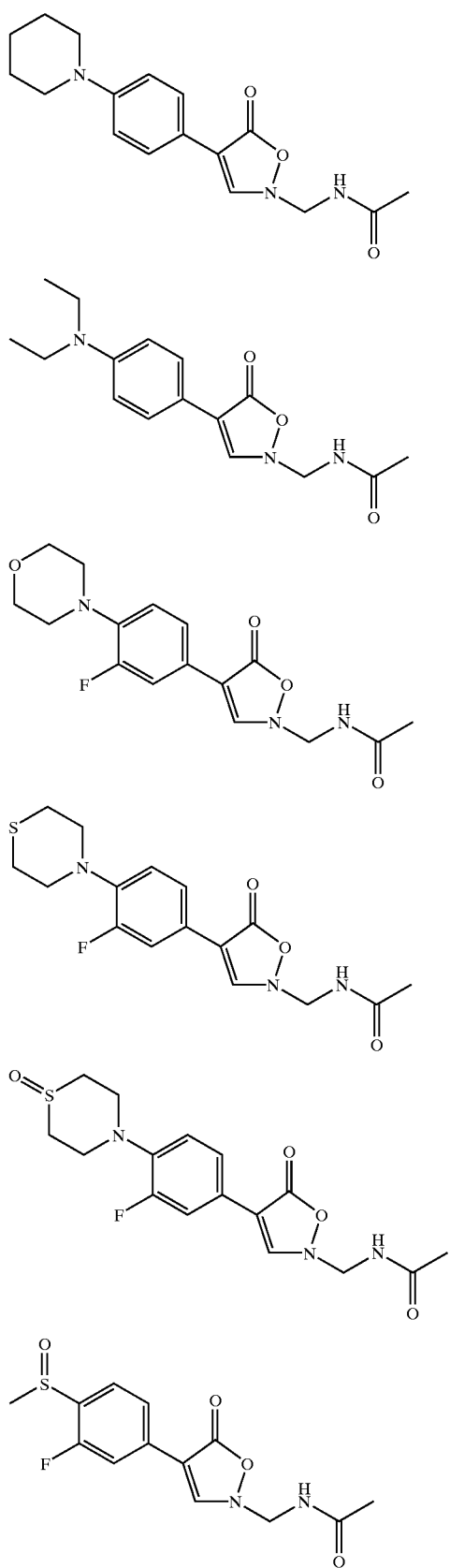
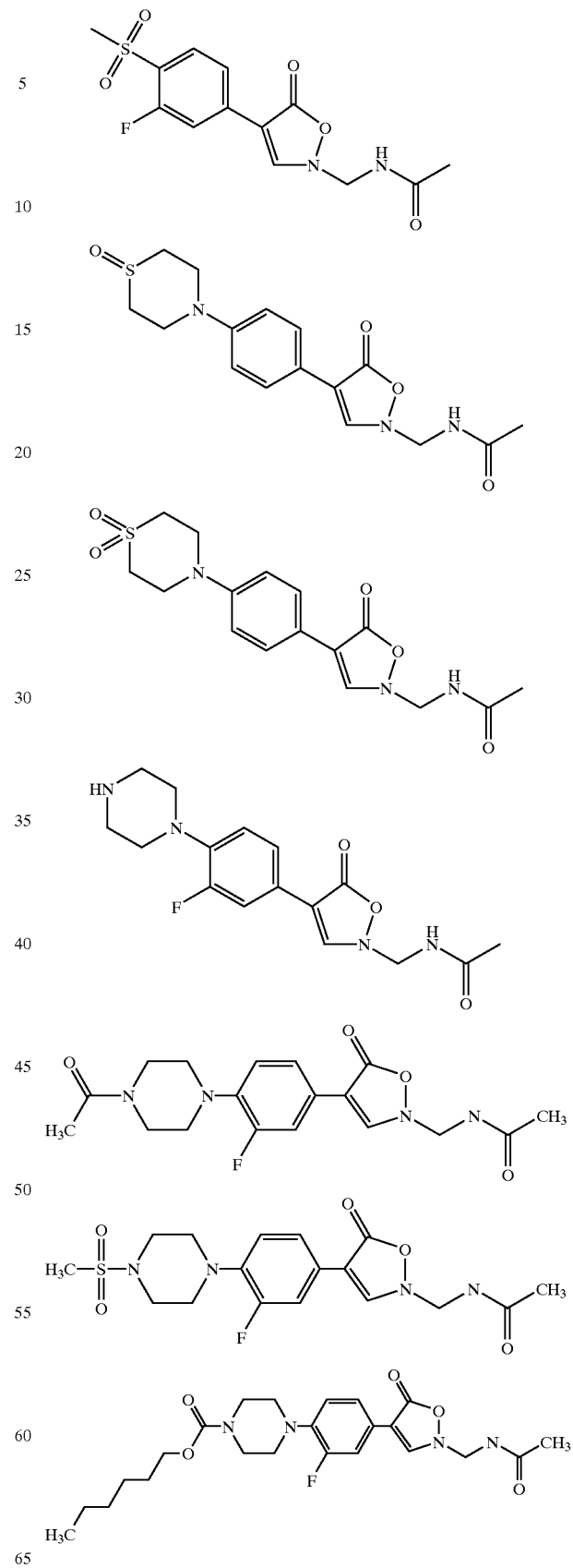

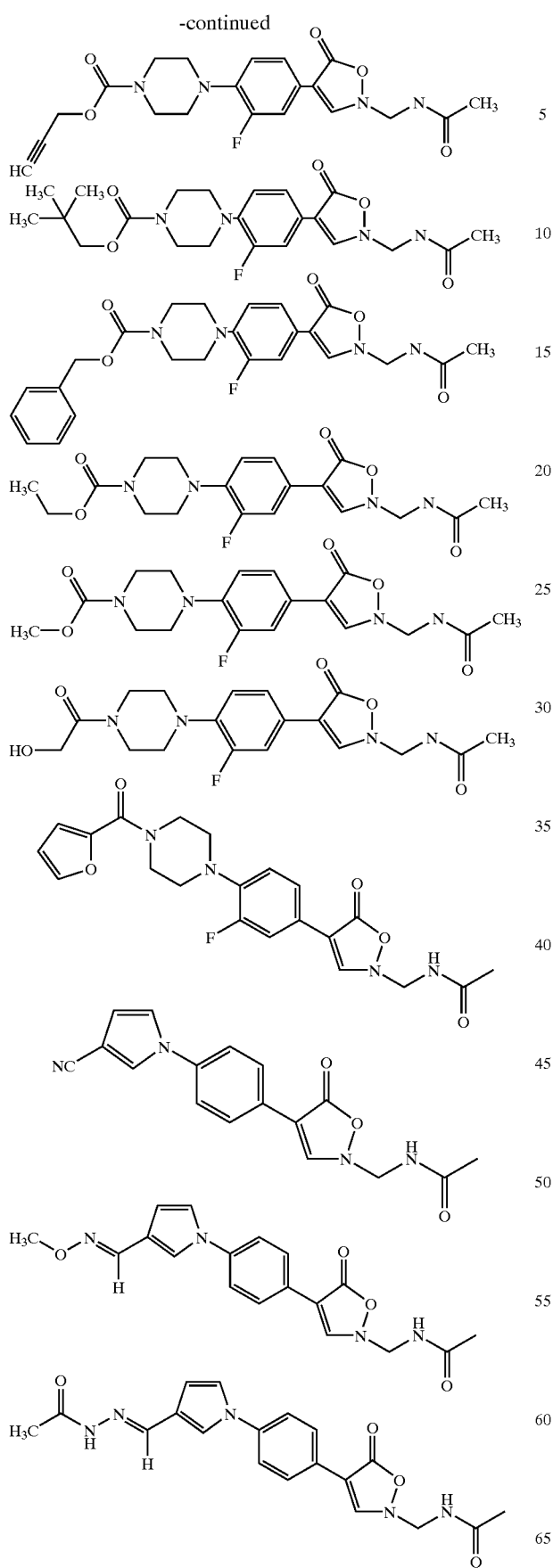

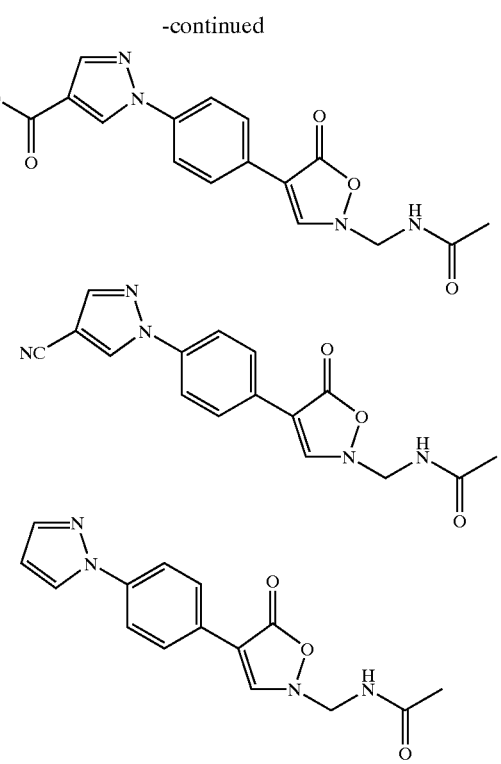

The compounds of the present invention can be made by the methods summarized below.

It will be apparent to those skilled in the art that the procedures described herein are representative in nature and that alternative procedures are feasible.

Isoxazolinones 5 of the present invention are preferably prepared via the sequence outlined in Scheme 1. Aryl acetic acids 1 are either commercially available or prepared by one of many well known methods in the chemical literature including but not limited to the sequence shown in Scheme 2 or 3. Isoxazolinone 3 is prepared by methods described by Marchesini [*J. Org. Chem.* 1984, 49, p. 4287–4290]. Reaction of 1 with sodium hydride and ethyl formate provides 2 which is in turn reacted with hydroxylamine yielding 3. Treatment of 3 with mild base, preferably potassium carbonate, in an appropriate solvent, preferably dichloromethane or N,N-dimethylformamide followed by addition of 4 (prepared by methods described by Barnes et al in U.S. Pat. No. 5,284,863) provides isoxazolinone 5.

Scheme 1

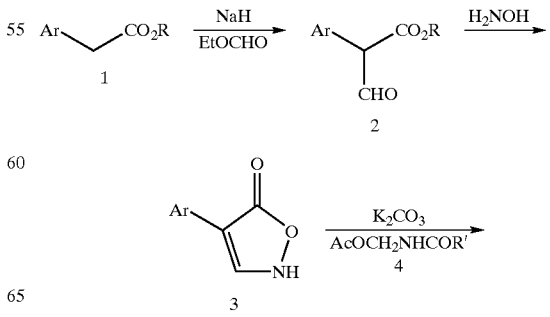

-continued

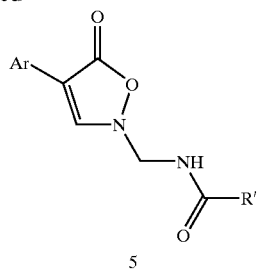

5

An alternative way to prepare aryl acetic esters 1 of the present invention is shown in Scheme 2. Treatment of triflate 6 (prepared from methyl 4-hydroxyphenyl acetate by methods known by those skilled in the art) with an N,N-dialkylamine in the manner described by Buchwald [*Tet. Lett.*, 1997, 38, p. 6363–6366] produces esters exemplified by 7. Aryl-bromides, -iodides, and -chlorides are also suitable as replacements for triflate 6 in Scheme 2. The N,N-dialkylamines used in Scheme 2 are either commercially available or are synthesized by literature procedures. Literature preparations of many cyclic N,N-dialkylamines have been detailed by Gadwood (WO 97/10223) and others are well known to those skilled in the art.

Scheme 2

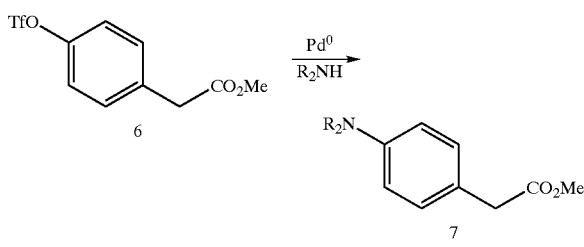

Another alternative to prepare aryl acetic esters 1 of the present invention is shown in Scheme 3. Treatment of 8 with a mild base, preferably potassium carbonate, and a primary or secondary amine or thiolate, in a suitable solvent, preferably acetonitrile or N,N-dimethylformamide, at a temperature between 25° C. and 100° C. provides 9. Compound 8 is commercially available. Compound 9 is converted to 11 or 12 by methods described by Gravestock (World Patent 97/14690). This sequence is also known to those skilled in the art as the Wiligerodt reaction. Conversion of 11 to 12 can also be accomplished by various methods known in the chemical literature including but not limited to treatment with acid in hot alcohol.

Scheme 3

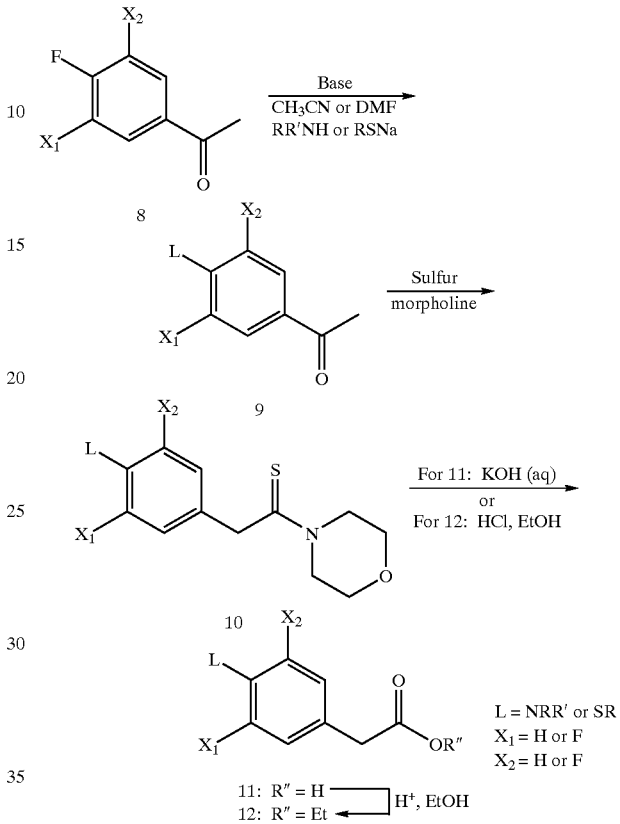

Sulfoxides and sulfones 14 and 16 are prepared by treating sulfides 13 and 15, respectively with an oxidizing agent such as m-chloroperoxybenzoic acid or osmium tetroxide by methods known by those skilled in the art and exemplified by Barbachyn [*J. Med. Chem.*, 1996, 39, 680–685].

Scheme 4

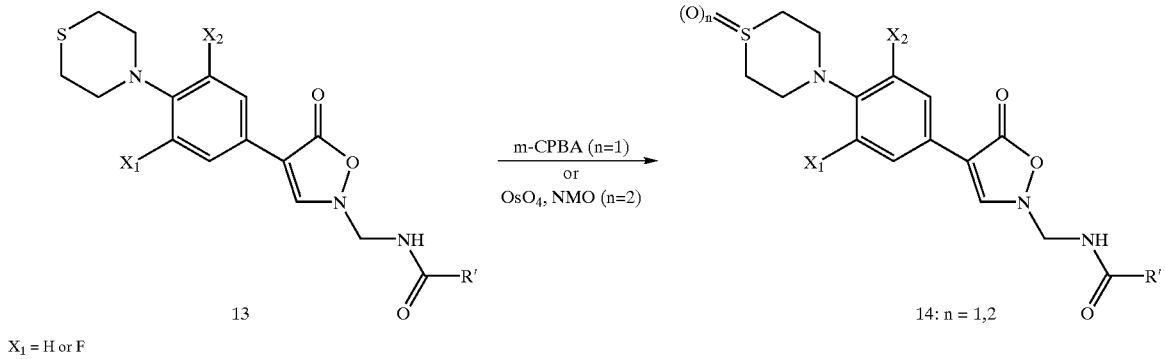

$X_1$ = H or F
$X_2$ = H or F

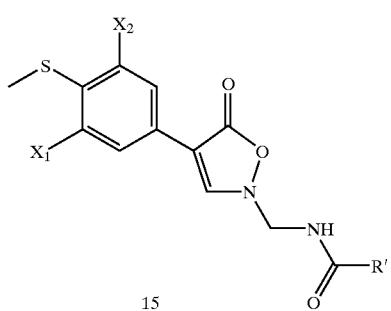

15

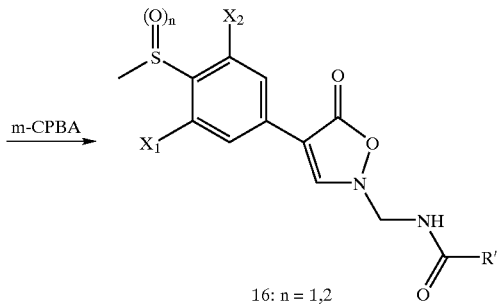

16: n = 1,2

An alternative method of preparing compound 18 of the present invention is shown in Scheme 5. Treatment of 17 with an appropriate organostannane provides 18. This method is known by those skilled in the art as the Stille cross-coupling reaction.

Scheme 5

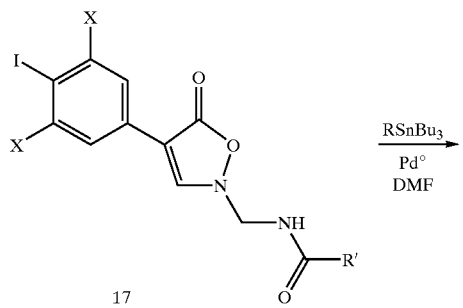

-continued

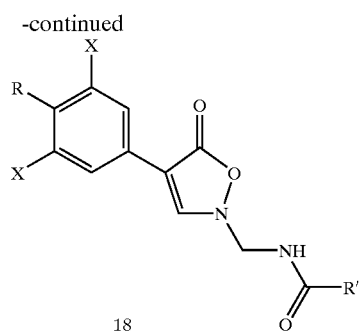

18

Preparation of 21, 22, 23, and 24 of the present invention is described in Scheme 6. Treatment of 19 with trifluoroacetic acid provides 20. Compound 20 is treated with an acid chloride, chloroformate, sulfonyl halide, or isocyanate in the presence of triethylamine by methods well known in the chemical literature to provide 21, 22, 23, and 24, respectively.

Scheme 6

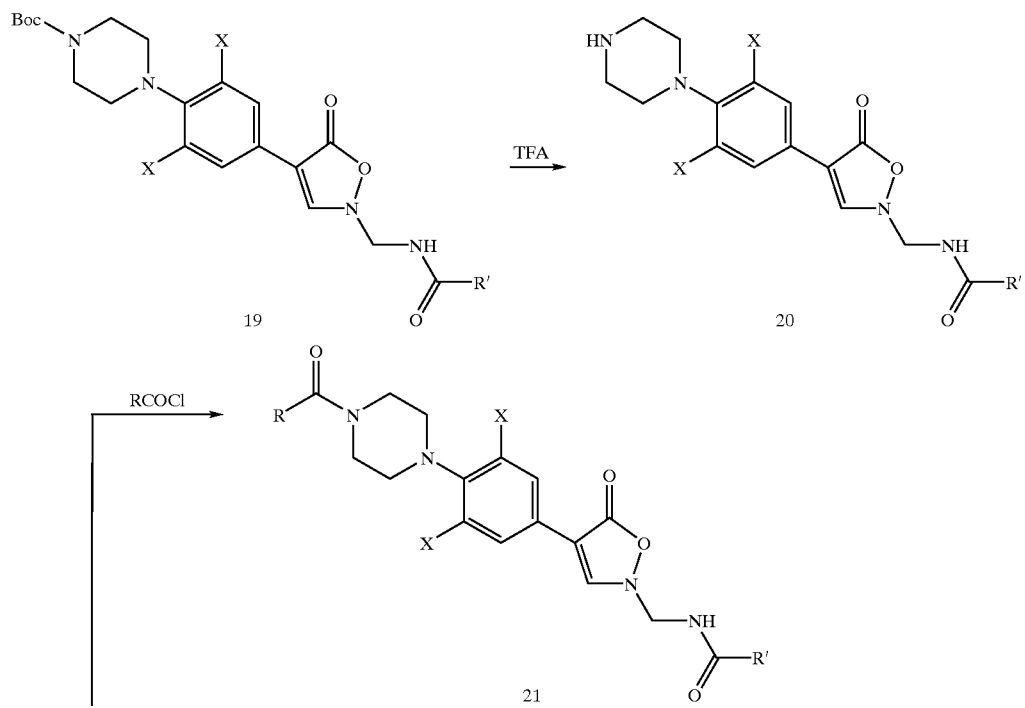

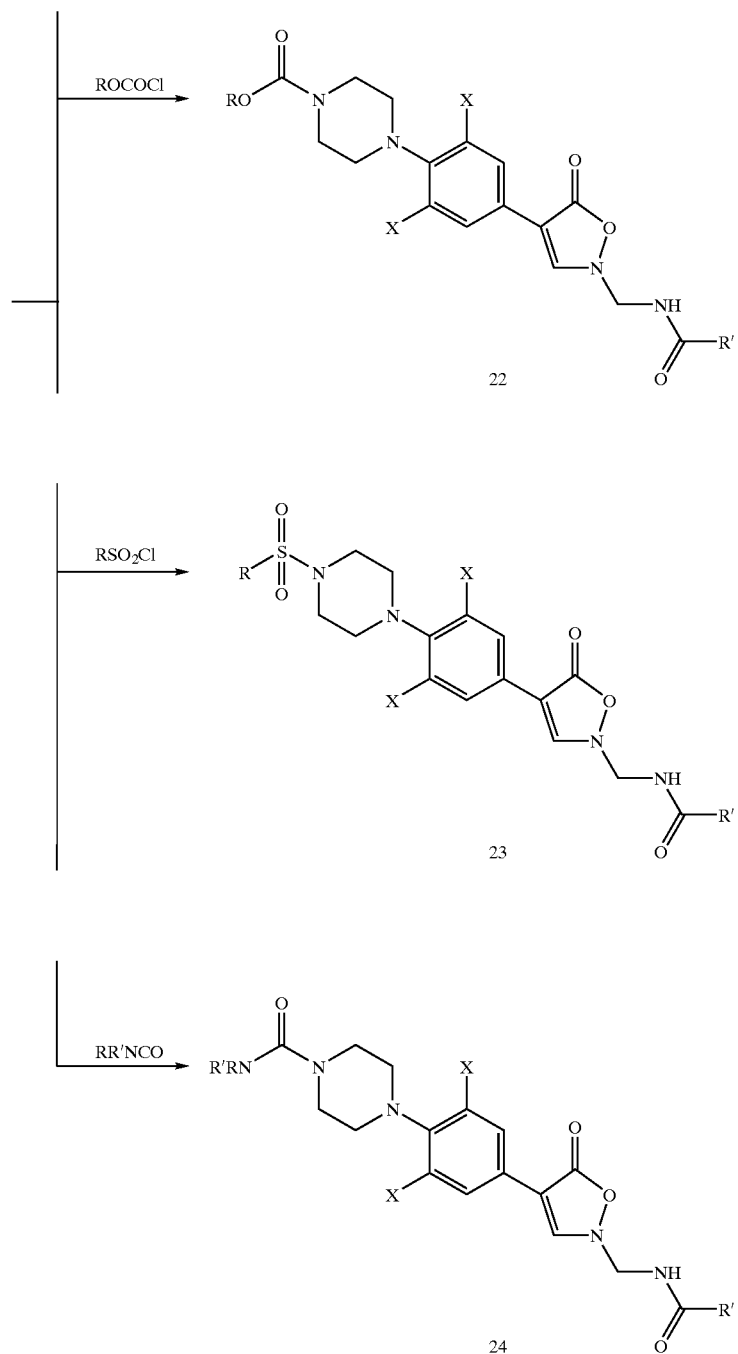

The triazole-substituted compounds 27 and 28 are prepared by cyclization of the azide 25 with acetylenes 26 (Scheme 7). This is a standard 3+2 cycloaddition which is well documented in the chemical literature. The acetylenes 26 are either commercially available or prepared by literature procedures. For example, cyanoacetylene is prepared according to Murahashi [*J. Chem. Soc. Jap.*, 1956, 77, 1689]. The cyclization reaction was usually carried out in a suitable solvent such as DMF, at a temperature between 25° C. and 80° C. Other suitable solvents include but are not limited to DMSO, NMP, and DMA. The two cyclization adducts 27 and 28 were separated using preparative HPLC or by triturating with a suitable solvent such as ethyl acetate. Other suitable solvents for trituration include but are not limited to methanol, ethanol, diethyl ether, and acetone.

Scheme 7: 1,2,3-Triazoles

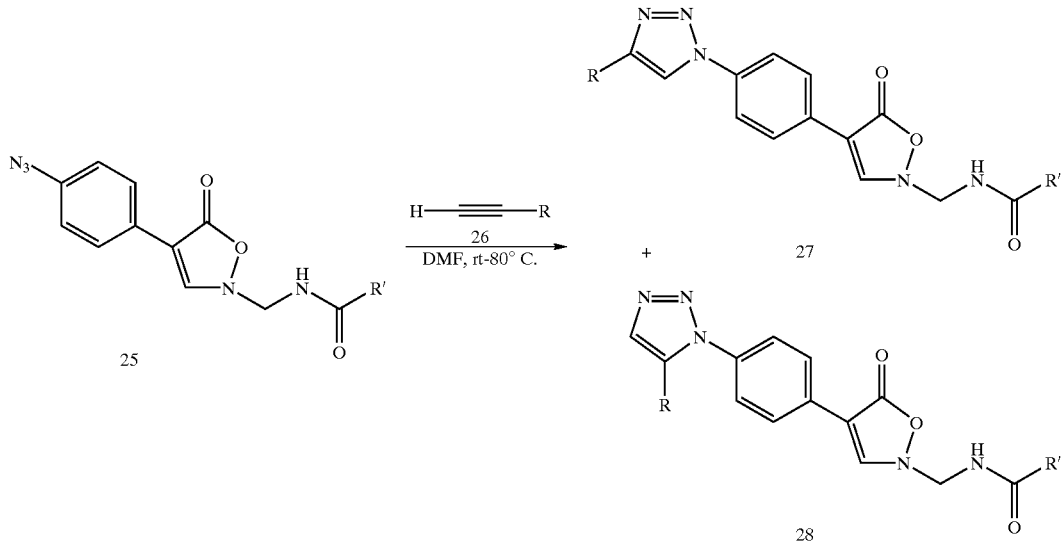

The azidophenylisoxazolinone 25 is reduced to aminophenylisoxazolinone 29 via one of the many well known methods in the chemical literature including but not limited to the treatment with stannous chloride in a suitable solvent such as a 2:1 combination of ethyl acetate and methanol. Treatment of aminophenylisoxazolinones 29 with 2,5-dimethoxytetrahydrofurans 30 in acetic acid provide pyrrole-substituted isoxazolinones 31 (Scheme 8). Subsequent conversions of the pyrrole (R=CHO) are also possible, for instance the corresponding oxime can be prepared by refluxing with 50% aqueous hydroxylamine in methanol.

Scheme 8: Pyrroles

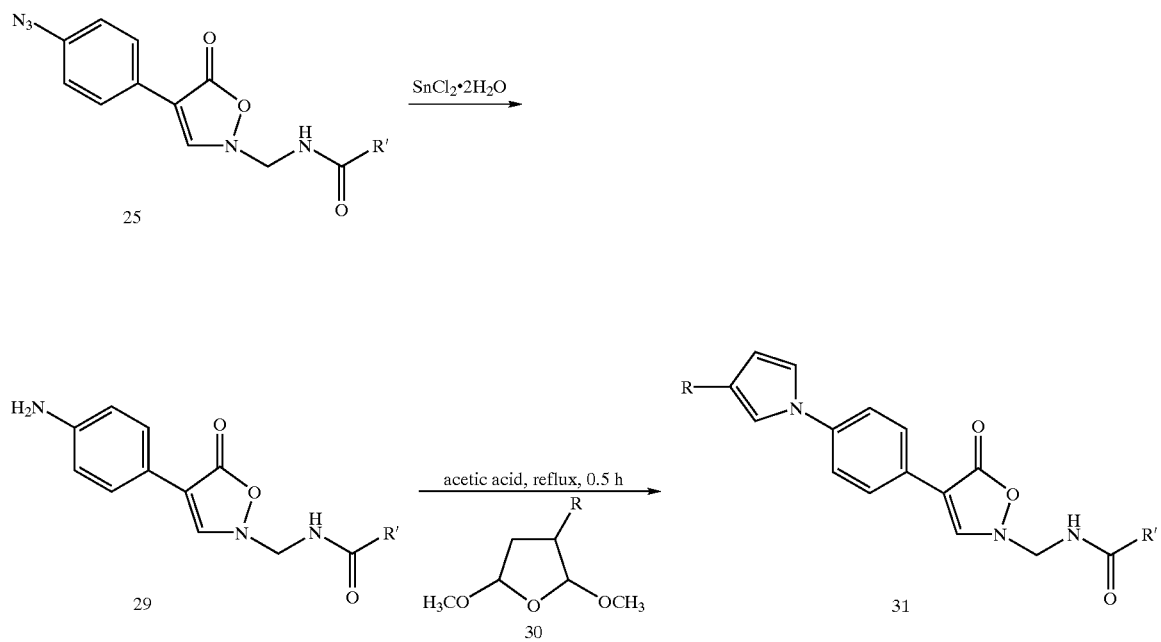

N-thioacetates 33 may be prepared from the corresponding N-acetates 32 using a variety of well known literature methods, for instance by refluxing in benzene with Lawesson's reagent. Other solvents such as toluene and xylene are also suitable.

Scheme 9: Thioacetates

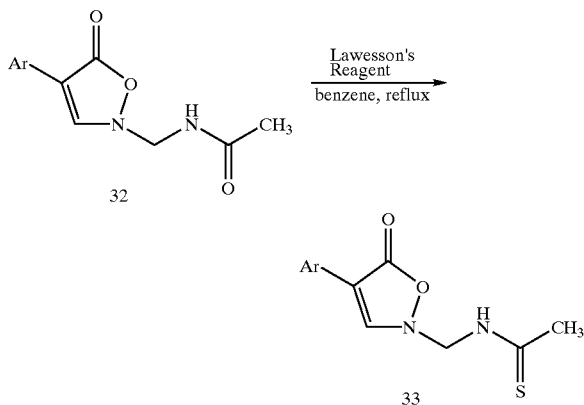

It will be understood that where the substituent groups used in the above reactions contain certain reaction-sensitive functional groups which might result in undesirable side-reactions, such groups may be protected by conventional protecting groups known to those skilled in the art. Suitable protecting groups and methods for their removal are illustrated, for example, in *Protective Groups in Organic Synthesis*, Theodora W. Greene (John Wiley & Sons, 1991). It is intended that such "protected" intermediates and end-products are included within the scope of the present disclosure and claims.

Some of the desired end-products of formula I contain an amine. In these cases, the final product may be recovered in the form of a pharmaceutically acceptable acid addition salt, e.g. by addition of the appropriate acid such as HCl, HI or methane-sulfonic acid to the amine.

It will be appreciated that certain products within the scope of formula I may have substituent groups which can result in formation of optical isomers. It is intended that the present invention include within its scope all such optical isomers as well as epimeric mixtures thereof, i.e. R- or S- or racemic forms.

The compounds of the invention are useful because they possess pharmacological activities in animals, including particularly mammals and most particularly, humans. The novel isoxazolinone derivatives of general formula I , or pharmaceutically acceptable salts or prodrugs thereof, are potent antibiotics active against gram-positive bacteria. While they may be used, for example, as animal feed additives for promotion of growth, as preservatives for food, as bactericides in industrial applications, for example in waterbased paint and in the white water of paper mills to inhibit the growth of harmful bacteria, and as disinfectants for destroying or inhibiting the growth of harmful bacteria on medical and dental equipment, they are especially useful in the treatment of bacterial infections in humans and other animals caused by the gram-positive bacteria sensitive to the new derivatives.

The pharmaceutically active compounds of this invention may be used alone or formulated as pharmaceutical compositions comprising, in addition to the active isoxazolinone ingredient, a pharmaceutically acceptable carrier or diluent. The compounds may be administered by a variety of means, for example, orally, topically or parenterally (intravenous or intramuscular injection). The pharmaceutical compositions may be in solid form such as capsules, tablets, powders, etc. or in liquid form such as solutions, suspensions or emulsions. Compositions for injection may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

Thus, according to another aspect of the invention, there is provided a method of treating a bacterial infection which comprises administering a therapeutically effective amount of the compound to a host, particularly a mammalian host and most particularly a human patient. The use of the compounds of the present invention as pharmaceuticals and the use of the compounds of the invention in the manufacture of a medicament for the treatment of bacterial infections are also provided.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 25 mg/day to about 2 g/day.

The preparations of pyrazoles substituted compounds are outlined in Scheme 10. Compound 29 was diazotized and then reduced to form hydrazine hydrochloride salt 34 via one of the many well known methods in the chemical literature including but not limited to the treatment with sodium nitrite and stannous chloride. Treatment of 34 with ethoxycarbonylmalondiadehyde, cyanomalondiadehyde [prepared according to Bertz, S. H., Dabbagh, G. and Cotte, P. in *J. Org. Chem*, 1982, 47, p. 2216,] or malondiadehyde [prepared according to Martinez, A. M., Cushmac, G. E., Rocek, J. in *J. Amer. Chem. Soc*, 1975, 97, p. 6502] in the presence of sodium bicarbonate at room temperature provides compound 35.

Scheme 10: Pyrazoles

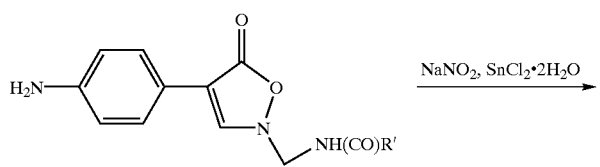

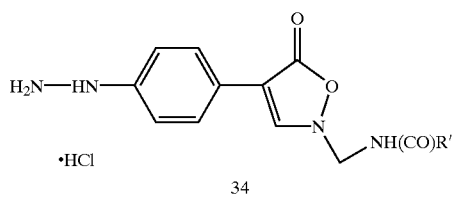
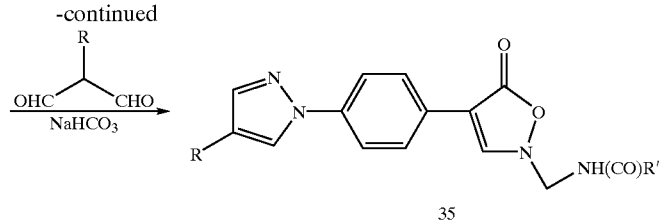

In Vitro Activity

Samples of the compounds prepared below in Examples 1–97 after solution in water and dilution with Nutrient Broth were found to exhibit the following ranges of Minimum Inhibitory Concentrations (MIC) versus the indicated microorganisms as determined by tube dilution. The MICs were determined using a broth micro dilution assay in accordance with that recommended by the National Committee for Clinical Laboratory Standards (NCCLS). Mueller-Hinton medium was used except for Streptococci which was tested in Todd Hewitt broth. The final bacterial inoculate contained approximately $5 \times 10^5$ cfu/ml and the plates were incubated at 35° C. for 18 hours in ambient air (Streptococci in 5% $CO_2$). The MIC was defined as the lowest drug concentration that prevented visible growth.

| Microorganism | MIC value in ug/ml |
| --- | --- |
| S. pneumoniae A9585 | ≦8 |
| E. faecalis A20688 | ≦16 |
| S. aureus A15090, penicillinase positive | ≦16 |

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

| | |
| --- | --- |
| h | hour(s) |
| mol | mole(s) |
| mmol | mmole(s) |
| g | gram(s) |
| min | minute(s) |
| rt | room temperature |
| THF | tetrahydrofuran |
| L | liter(s) |
| mL | milliliter(s) |
| Et₂O | diethyl ether |
| EtOAc | ethyl acetate |
| MeOH | methanol |
| DMF | dimethylformamide |

In the following examples, all temperatures are given in degrees Centigrade. Melting points were determined on an electrothermal apparatus and are not corrected. Proton and carbon-13 nuclear magnetic resonance ($^1$H and $^{13}$C NMR) spectra were recorded on a Bruker AM-300 or a Varian Gemini 300 spectrometer. All spectra were determined in CDCl$_3$, DMSO-d$_6$, CD$_3$OD, or D$_2$O unless otherwise indicated. Chemical shifts are reported in δ units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Infrared spectra were determined on a Perkin-Elmer 1800 FT-IR spectrometer from 4000 cm$^{-1}$ to 400 cm$^{-1}$, calibrated to 1601 cm$^{-1}$ absorption of a polystyrene film, and are reported in reciprocal centimeters (cm$^{-1}$). Mass spectra were recorded on a Kratos MS-50 or a Finnegan 4500 instrument utilizing direct chemical ionization (DCI, isobutene), fast atom bombardment (FAB), or electron ion spray (ESI). Ultraviolet spectra were determined on a Hewlett Packard 8452 diode array spectrophotometer in the solvent indicated.

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure with the indicated solvents. Reversed-phase analytical thin-layer chromatography was carried out on precoated reverse phase plates and visualized using UV light or iodine vapors.

Example 1

N-[[4-(4-methylthiophenyl)-5-oxo-2-isoxazolinyl]methyl]acetamide

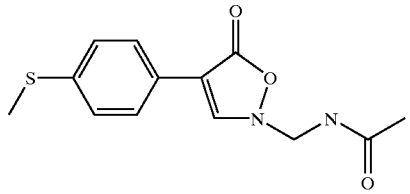

A. Ethyl 4-methylthiophenylacetate

To a solution of 4-methylthiophenylacetic acid (1.0 g, 5.48 mmol) in 55 mL of ethanol was slowly added a catalytic amount of concentrated sulfuric acid. The mixture was stirred at room temperature overnight and then concentrated at reduced pressure. The residue was partitioned between methylene chloride and sodium bicarbonate. The organic layer was washed with brine, dried with magnesium sulfate, filtered, and concentrated to yield 1.1 g of a colorless oil (96%). $^1$H NMR (300 MHz, CDCl$_3$) δ7.22 (s, 4H), 4.15 (q, J=6 Hz, 2H), 3.57 (s, 2H), 2.47 (s, 3H), 1.25 (t, J=6 Hz, 3H).

B. Ethyl 4-methylthio-α-formyl-phenylacetate

A suspension of NaH (0.84 g, 20.8 mmol) was added at room temperature to a solution of ethyl 4-methylthiophenylacetate (1.1 g, 5.2 mmol) in ethyl formate (20 mL). The mixture was stirred at room temperature for 1 hour and then cold 0.5 N HCl (20 mL) was added slowly. The crude reaction was then extracted with ether, and the organic layer was washed with sodium bicarbonate, brine, dried over magnesium sulfate, filtered, and concentrated to yield 1.2 g of ethyl 4-methylthio-α-formyl-phenylacetate as a colorless oil, which was used in the next step without purification.

C. 4-(4-methylthio)-phenylisoxazolin-5-one

To a solution of ethyl 4-methylthio-α-formyl-phenylacetate in 20 mL of methanol and 1 mL of water was added hydroxylamine hydrochloride (0.54 g, 7.8 mmol). The mixture was heated to reflux for 1 hour. The solvent was evaporated and the residue was triturated with water to afford a precipitate, which was then further triturated with ether to yield 0.48 g (two steps, 44%) of a pale yellow solid. $^1$H NMR (300 MHz, MeOH-d$_4$) δ8.74 (s, 1H), 7.66 (d, J=8 Hz, 2H), 7.25 (d, J=8 Hz, 2H), 2.46 (s, 3H).

D. N-[[4-(4-methylthiophenyl)-5-oxo-2-isoxazolinyl]methyl]acetamide

To a solution of 4-(4-methylthio)-phenylisoxazolin-5-one (0.2 g, 0.97 mmol) in 10 mL of methylene chloride was added potassium carbonate (0.67 g, 4.85 mmol) and N-(hydroxymethyl)acetamide acetate (0.64 g, 4.85 mmol). The mixture was stirred at room temperature for 18 hours. It was then poured into 10 mL of 1N HCl and extracted three times with chloroform. The organic layer was then washed with sodium bicarbonate, brine, dried over magnesium sulfate, filtered, concentrated to yield a tan solid, which was then recrystallized with hexane/chloroform. The resulting solid was further purified by triturating with ether to yield 0.186 g (69%) of a tan solid. $^1$H NMR (300 MHz, DMSO-d$_6$) δ8.93 (s, 1H), 7.72 (d, J=9 Hz, 2H), 7.28 (d, J=9 Hz, 2H), 5.02 (d, J=6 Hz, 2H), 2.48 (s, 3H), 1.84 (s, 3H).

Example 2

N-{[4-(3-fluoro-4-oxido-4-morpholin-4-ylphenyl)-5-oxo-2-hydroisoxazol-2-yl]methyl}acetamide

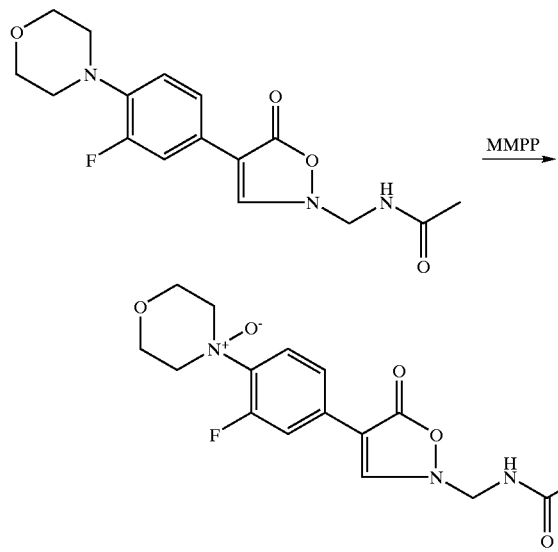

To N-{[4-(3-fluoro-4-morpholin-4-ylphenyl)-5-oxo-2-hydroisoxazol-2-yl]methyl}acetamide (200 mg, 0.60 mmol) in 50 mL methanol was added magnesium monoperoxyphthalate (300 mg, 0.60 mmol). After 2 hours at ambient temperature the white precipitate was filtered and the filtrate was concentrated. The remaining residue was pushed through a plug of basic alumina with dichloromethane. The eluant was concentrated and recrystallized from dichloromethane/hexanes to afford 162 mg (44%) of the title compound as a brown solid. $^1$H NMR (DMSO-d$_6$; 300 MHz) δ9.19 (s, 1H), 9.02 (t, J=6.1 Hz, 1H), 8.62–8.55 (m, 2H), 7.82–7.75 (m, 2H), 5.09 (d, J=6.0 Hz, 2H), 4.44 (app t, J=11.1 Hz, 2H), 4.08 (app t, J=9.6 Hz, 2H), 3.78 (app d, J=11.1 Hz, 2H), 2.89 (app d, J=10.5 Hz, 2H), 1.86 (s, 3H); ESI (M+H)$^+$=352.

Example 3

N-({4-[4-(methylsulfinyl)phenyl]-5-oxo-2-hydroisoxazol-2-yl}methyl)acetamide

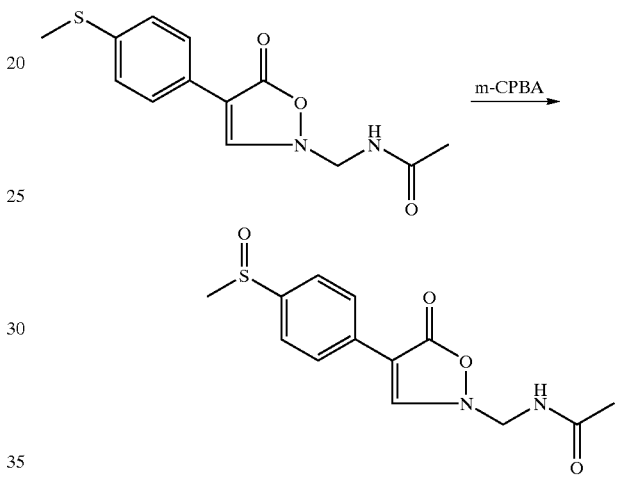

To N-{[4-(4-methylthiophenyl)-5-oxo-2-hydroisoxazol-2-yl]methyl}acetamide (1.0 g, 3.6 mmol) in 50 mL chloroform at 0° C. was added m-CPBA (1.12 g, 3.6 mmol) in 30 mL chloroform via syringe pump over 2 hours. Saturated sodium bicarbonate was added and the reaction mixture was stirred vigorously for 10 minutes at which time it was poured into saturated sodium bicarbonate and 4:1 chloroform-:methanol. The organic layer was washed with brine, dried over magnesium sulfate, filtered and concentrated. The residue was triturated with ether providing 800 mg (79%) of the title compound as a colorless solid. $^1$H NMR (DMSO-d$_6$; 300 MHz) δ9.11 (s, 1H), 8.96 (t, J=6.1 Hz, 1H), 7.96 (d, J=6.6 Hz, 2H), 7.67 (d, J=6.6 Hz, 2H), 5.03 (d, J=6.1 Hz, 2H), 2.73 (s, 3H), 1.84 (s, 3H); ESI (M+H)$^+$=295.

Example 4

N-({4-[4-(methylsulfonyl)phenyl]-5-oxo-2-hydroisoxazol-2-yl}methyl)acetamide

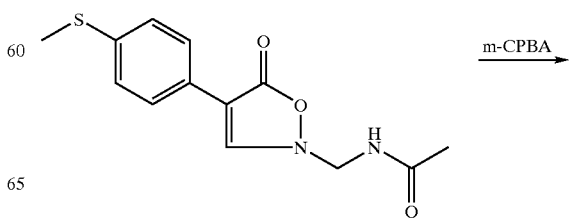

-continued

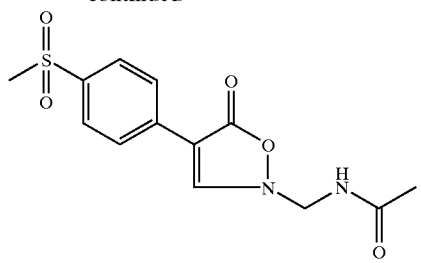

To N-{[4-(4-methylthiophenyl)-5-oxo-2-hydroisoxazol-2-yl]methyl}acetamide (200 mg, 0.72 mmol) in 20 mL chloroform at 0° C. was added m-CPBA (450 mg, 1.44 mmol) in 5 mL chloroform. After 30 minutes saturated sodium bicarbonate was added and the reaction mixture was extracted with chloroform. The organic layer was washed with brine, dried over magnesium sulfate, filtered, and concentrated. The residue was precipitated from acetone/1:1 hexanes:ether providing 112 mg (50%) of the title compound as a colorless solid. $^1$H NMR (DMSO-$d_6$; 300 MHz) δ9.24 (s, 1H), 9.01 (t, J=6.1 Hz, 1H), 8.02 (d, J=8.6 Hz, 2H), 7.91 (d, J=8.6 Hz, 2H), 5.11 (d, J=6.2 Hz, 2H), 3.20 (s, 3H), 1.86 (s, 3H); ESI (M+H)$^+$=311.

Example 5

N-({4-[4-(1,1-dioxo(1,4-thiazaperhydroin-4-yl))-3-fluorophenyl]-5-oxo-2-hydroisoxazol-2-yl}methyl)acetamide

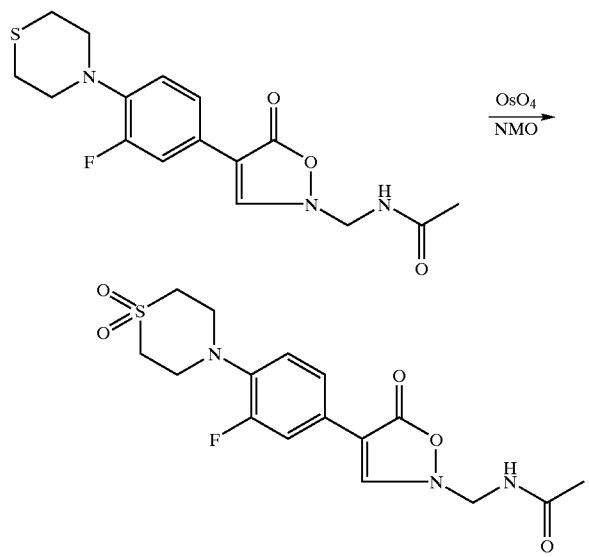

To N-{[4-(3-fluoro-4-(1,4-thiazaperhydroin-4-yl)phenyl)-5-oxo-2-hydroisoxazol-2-yl]methyl}acetamide (100 mg, 0.29 mmol) in 2 mL water and 8 mL acetone was added N-methylmorpholine N-oxide (98 mg, 0.85 mmol) followed by osmium tetroxide (2.5 wt % in isopropanol; 7 μl; 0.07 mmol). After 18 hours at ambient temperature saturated sodium bisulfite was added and the reaction mixture was extracted with 4:1 chloroform:methanol. The organic layer was concentrated providing 85 mg (77%) of the title compound as a colorless solid. $^1$H NMR (DMSO-$d_6$; 300 MHz) δ8.95 (s, 1H), 8.92 (t, J=6.2 Hz, 1H), 7.62–7.51 (m, 2H), 7.17 (app t, J=9.2 Hz, 1H), 4.99 (d, J=6.2 Hz, 2H), 3.52–3.48 (m, 4H), 3.27–3.23 (m, 4H), 1.82 (s, 3H); ESI (M+H)$^+$=384.

Example 6

4-(3-Fluoro-4-morpholin-4-ylphenyl)-2-{[(thioxoethyl)amino]methyl}-2-hydroisoxazol-5-one

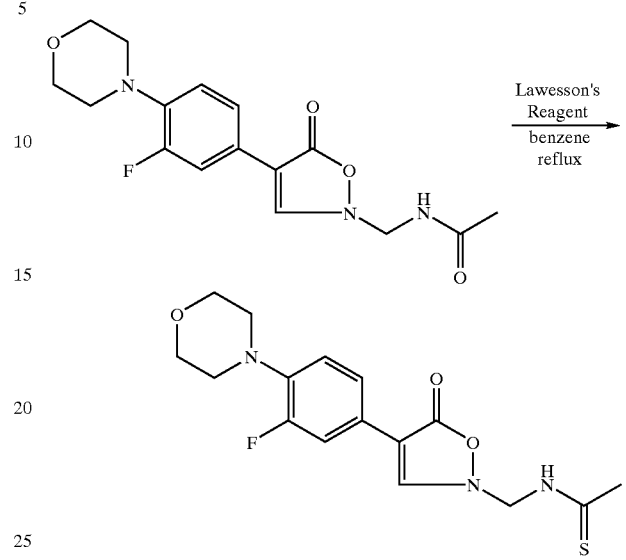

A mixture of N-{[4-3-fluoro-4-morpholinylphenyl-5-oxo-2-isoxazolinyl]methyl}acetamide (0.25 g, 0.75 mmol) and Lawesson's reagent (0.4 g, 1.0 mmol) in 10 mL of benzene was heated at reflux for 3 hours. The mixture was then concentrated under reduced pressure. The residue was purified using silica gel chromatography eluting with methylene chloride and ethyl acetate to give a colorless solid (80 mg, 30%): $^1$H NMR (300 MHz, CDCl$_3$) δ8.61 (br s, 1H), 8.49 (s, 1H), 7.50 (dd, J=1.5 and 13.8 Hz, 1H), 7.40 (dd, J=1.5 and 10.2 Hz, 1H), 7.12 (t, J=10.2 Hz, 1H), 5.56 (d, J=6.3 Hz, 2H), 3.94 (m, 4H), 3.17 (m, 4H), 2.57 (s, 3H).

Example 7

N-{[4-(4-acetylphenyl)-5-oxo-2-hydroisoxazol-2-yl]methyl}acetamide

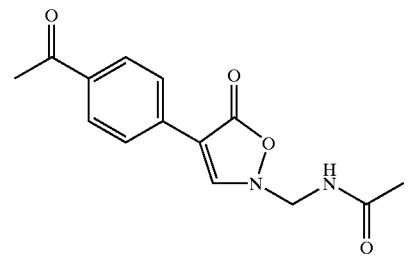

To N-{[4-phenyl-5-oxo-2-hydroisoxazol-2-yl]methyl}acetamide (3.0 g, 12.9 mmol) and aluminum (III) chloride (13.8 g, 103.4 mmol) in 150 mL 1,2-dichloroethane was added acetyl chloride (7.3 mL, 103.4 mmol) dropwise over 10 minutes. The resultant red mixture was heated to 80° C. for 3.5 hours, cooled to ambient temperature, and poured over 10 minutes into a rapidly stirring mixture of 20% methanol/chloroform and 1N hydrochloric acid which was immersed in an ice bath. The mixture was poured into a separatory funnel, and the layers were separated. The aqueous layer was extracted twice with 20% methanol/chloroform, and the combined organics were then washed successively with 1N sodium hydroxide, saturated sodium bicarbonate, and brine. The organic layer was then dried over magnesium sulfate, filtered, and concentrated to an amorphous yellow solid which was dissolved in 20% methanol/chloroform. Ether was added and the mixture was stored at 0° C. for 18 hours. The resultant precipitate was filtered to provide 2.48 g (70%) of the title compound as a pale pink solid. $^1$H NMR (DMSO-d$_6$; 300 MHz) δ9.18 (s, 1H), 9.00 (t, J=6.1 Hz, 1H), 7.96 (d, J=6.7 Hz, 2H), 7.91 (d, J=6.6 Hz, 2H), 5.10 (d, J=6.2 Hz, 2H), 2.56 (s, 3H), 1.86 (s, 3H); ESI (M+H)$^+$=275.

Example 8

N-({4-[4-((hydroxyimino)ethyl)phenyl]-5-oxo-2-hydroisoxazol-2-yl}methyl)acetamide

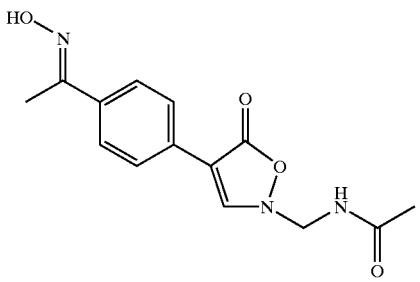

A mixture of N-{[4-(4-acetylphenyl)-5-oxo-2-hydroisoxazol-2-yl]methyl}acetamide (2.0 g, 7.3 mmol) and 50% aqueous hydroxylamine (1.0 mL, 14.6 mmol) was heated to reflux for 1.5 hours, concentrated to near dryness and redissolved in 20% methanol/chloroform. Hexanes were added until the solution became cloudy and the mixture was stored at 0° C. for 3 hours. The precipitate was filtered providing 1.42 g (67%) of the title compound as a pale yellow solid. $^1$H NMR (DMSO-d$_6$; 300 MHz) δ11.21 (s, 1H), 9.01 (s, 1H), 8.96 (t, J=6.2 Hz, 1H), 7.78 (d, J=8.6 Hz, 2H), 7.66 (d, J=8.6 Hz, 2H), 5.04 (d, J=6.2 Hz, 2H), 2.19 (s, 3H), 1.84 (s, 3H); ESI (M+H)$^+$=290.

Example 9

N-{[4-(4-(2-furyl)phenyl)-5-oxo-2-hydroisoxazol-2-yl]methyl}acetamide

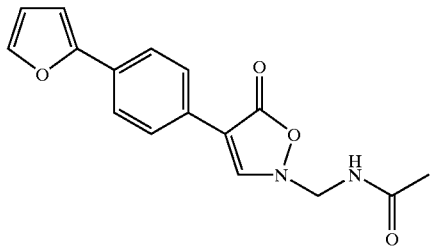

Nitrogen was bubbled through a mixture of N-{[4-(4-iodophenyl)-5-oxo-2-hydroisoxazol-2-yl]methyl}acetamide (300 mg, 0.84 mmol), 2-tributylstannylfuran (0.26 mL, 0.84 mmol), tris(dibenzylideneacetone)dipalladium(0) (77 mg, 0.08 mmol), triphenylarsine (51 mg, 0.17 mmol), and lithium chloride (106 mg, 2.51 mmol) in 5 mL DMF. The reaction mixture was capped and allowed to stir at ambient temperature for 8 hours, at which time it was diluted with 20% methanol/chloroform, filtered thru celite and concentrated. The residue was suspended in chloroform, loaded onto a Biotage flash 40i chromatography module (12M) thru a frit, and eluted with 50% hexane/ethyl acetate providing a solid which was triturated with chloroform/ether to provide 132 mg (53%) of the title compound as a colorless solid. $^1$H NMR (DMSO-d$_6$; 300 MHz) δ9.00 (s, 1H), 8.94 (t, J=6.0 Hz, 1H), 7.82 (d, J=8.4 Hz, 2H), 7.74–7.70 (m, 2H), 6.95 (d, J=3.2 Hz, 1H), 6.60–6.59 (m, 1H), 5.04 (d, J=6.1 Hz, 2H), 1.85 (s, 3H); ESI (M+H)$^+$=299.

Example 10

N-{[5-oxo-4-(4-(2-thienyl)phenyl)-2-hydroisoxazol-2-yl]methyl}acetamide

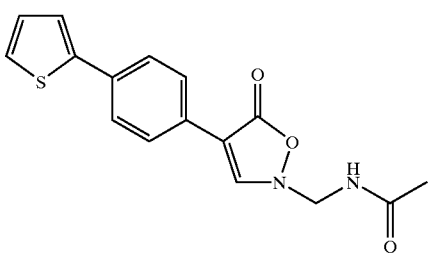

Nitrogen was bubbled through a mixture of N-{[4-(4-iodophenyl)-5-oxo-2-hydroisoxazol-2-yl]methyl}acetamide (300 mg, 0.84 mmol), 2-tributylstannylthiophene (0.27 mL, 0.84 mmol), tris(dibenzylideneacetone)dipalladium(0) (77 mg, 0.08 mmol), triphenylarsine (51 mg, 0.17 mmol), and lithium chloride (106 mg, 2.51 mmol) in 5 mL DMF. The reaction mixture was capped and allowed to stir at ambient temperature for 8 hours, at which time it was diluted with 20% methanol/chloroform, filtered thru celite and concentrated. The residue was suspended in chloroform, loaded onto a Biotage flash 40i chromatography module (12M) thru a frit, and eluted with 15% acetone/chloroform providing a solid which was triturated with chloroform/ether to provide 165 mg (63%) of the title compound as a colorless solid. $^1$H NMR (DMSO-d$_6$; 300 MHz) δ9.00 (s, 1H), 8.95 (t, J=6.0 Hz, 1H), 7.81 (d, J=7.3 Hz, 2H), 7.68 (d, J=7.4 Hz, 2H), 7.54–7.52 (m, 2H), 7.15–7.11 (m, 1H), 5.04 (d, J=6.1 Hz, 2H), 1.85 (s, 3H); ESI (M+H)$^+$=315.

Example 11

N-{[4-(4-(2H,3H-1,4-dioxin-5-yl)phenyl)-5-oxo-2-hydroisoxazol-2-yl]methyl}acetamide

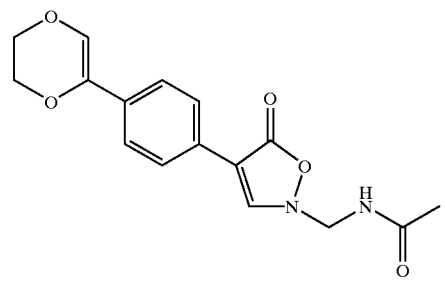

Nitrogen was bubbled through a mixture of N-{[4-(4-iodophenyl)-5-oxo-2-hydroisoxazol-2-yl]methyl}acetamide (300 mg, 0.84 mmol), 2-(trbutylstannyl)-5,6-dihydro-[1,4]-dioxin (346 mg, 0.92 mmol), tris(dibenzylideneacetone)dipalladium(0) (77 mg, 0.08 mmol), triphenylarsine (51 mg, 0.17 mmol), and lithium chloride (106 mg, 2.51 mmol) in 5 mL DMF. The reaction mixture was capped and allowed to stir at ambient temperature for 16 hours, at which time it was diluted with 20% methanol/chloroform, 10% aqueous potassium fluoride was added and the mixture was allowed to rapidly stir for 1 hours. The reaction mixture was filtered thru celite and concentrated. The resultant black oil was dissolved in 20% methanol/chloroform, adsorbed onto silica gel and loaded into a Biotage flash 40i chromatography module SIM. Chromatography was performed using a 12M silica gel cartridge eluting with 20% acetone/chloroform providing an amber oil which was triturated with ether, yielding 115 mg (44%) of the title compound as a tan solid. $^1$H NMR (DMSO-$d_6$; 300 MHz) δ8.93–8.88 (m, 2H), 7.70 (d, J=8.5 Hz, 2H), 7.41 (d, J=8.4 Hz, 2H), 6.96 (s, 1H), 5.01 (d, J=6.2 Hz, 2H), 4.22–4.19 (m, 2H), 4.10–4.07 (m, 2H), 1.85 (s, 3H); ESI (M+H)$^+$=317.

Example 12

N-{[5-oxo-4-(4-pyrazin-2-ylphenyl)-2-hydroisoxazol-2-yl]methyl}acetamide

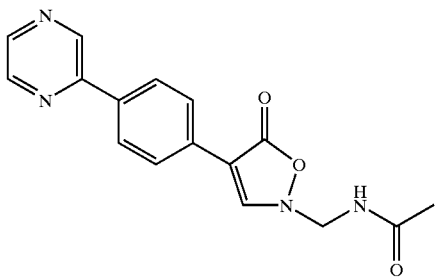

Nitrogen was bubbled through a mixture of N-{[4-(4-iodophenyl)-5-oxo-2-hydroisoxazol-2-yl]methyl}acetamide (300 mg, 0.84 mmol), 2-(tributylstannyl)pyrazine (340 mg, 0.92 mmol), tris(dibenzylideneacetone)dipalladium(0) (77 mg, 0.08 mmol), triphenylarsine (51 mg, 0.17 mmol), and lithium chloride (106 mg, 2.51 mmol) in 5 mL DMF. The reaction mixture was capped and allowed to stir at ambient temperature for 16 hours, at which time it was diluted with 20% methanol/chloroform, 10% aqueous potassium fluoride was added and the mixture was allowed to rapidly stir for 1 hour. The reaction mixture was filtered thru celite and concentrated. The resultant black oil was dissolved in 20% methanol/chloroform, adsorbed onto silica gel and loaded into a Biotage flash 40i chromatography module SIM. Chromatography was performed using a 12M silica gel cartridge eluting with 25% acetone/chloroform providing an amber oil which was triturated with ether, yielding 52 mg (44%) of the title compound as a colorless solid. $^1$H NMR (DMSO-$d_6$; 300 MHz) δ9.28 (d, J=1.4 Hz, 1H), 9.11 (s, 1H), 8.97 (t, J=6.1 Hz, 2H), 8.71 (app t, J=1.9 Hz, 1H), 8.59 (d, J=2.5 Hz, 1H), 8.17 (d, J=8.5 Hz, 2H), 7.94 (d, J=8.5 Hz, 2H), 5.07 (d, J=6.2 Hz, 2H), 1.86 (s, 3H); ESI (M+H)$^+$=311.

Example 13

N-{[5-oxo-4-(4-{4-[2-(1,1,2,2-tetramethyl-1-silapropoxy)acetyl]piperazinyl}phenyl)-2-hydroisoxazol-2-yl]methyl}acetamide

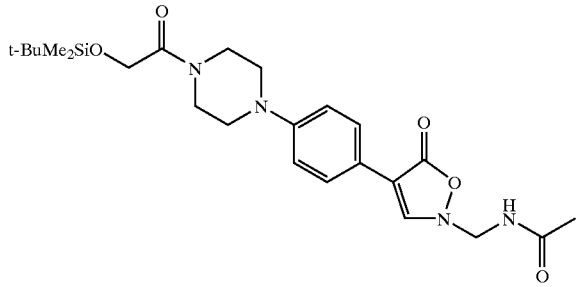

To N-{[5-oxo-4-(piperazinylphenyl)-2-hydroisoxazol-2-yl]methyl}acetamide trifluoroacetate salt (0.43 g, 1.0 mmol) in 2 mL of dimethylformamide and 10 mL dichloromethane was added triethylamine (0.7 mL, 0.5 mmol) followed by (t-butyldimethylsilyloxy)acetyl chloride (1.0 g, 4.8 mmol). The resultant mixture was allowed to stir at ambient temperature for 1.5 hours before being partitioned between dichloromethane and water. The organic layer was washed with saturated sodium bicarbonate, brine, dried over magnesium sulfate, filtered and concentrated. The residue was triturated with ether to provide 0.24 g (49%) of the title compound. $^1$H NMR (methanol-$d_4$; 300 MHz) δ8.49 (s, 1H), 7.66 (d, J=8.8 Hz, 2H), 7.00 (d, J=8.8 Hz, 2H), 5.07 (s, 2H), 4.42 (s, 2H), 3.73 (t, J=4.9 Hz, 4H), 3.24 (t, J=4.9 Hz, 4H), 1.94 (s, 3H), 0.95 (s, 9H); ESI (M+H)$^+$=489.

Example 14

N-[(4-{4-[4-(2-hydroxyacetyl)piperazinyl]phenyl}-5-oxo-2-hydroisoxazol-2-yl)methyl]acetamide

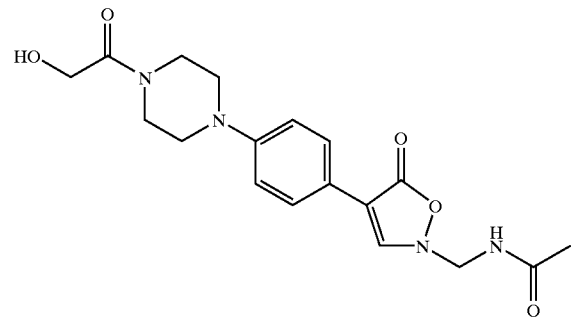

To N-{[5-oxo-4-(4-{4-[2-(1,1,2,2-tetramethyl-1-silapropoxy)acetyl]piperazinyl}phenyl)-2-hydroisoxazol-2-yl]methyl}acetamide (0.3 g, 0.6 mmol) in 4 mL dichloromethane was added 4 mL trifluoroacetic acid. After 1 hour, the reaction was concentrated, the residue was partitioned between dichloromethane and saturated sodium bicarbonate solution. The organic layer was washed with brine, dried over magnesium sulfate, filtered and concentrated. The residue was triturated with ether to provide 92 mg (40%) of the title compound. $^1$H NMR (DMSO-$d_6$; 300 MHz) δ8.87 (t, J=6.2 Hz, 1H), 8.74 (s, 1H), 7.63 (d, J=8.7 Hz, 2H), 6.97 (d, J=8.9 Hz, 2H), 4.95 (d, J=6.2 Hz, 2H), 4.64 (t, J=5.6 Hz, 1H), 4.13 (d, J=5.6 Hz, 2H), 3.60 (br s, 2H), 3.48 (br s, 2H), 3.17 (br s, 4H), 1.83 (s, 3H); ESI (M+H)$^+$=375.

Example 15

N-{[4-(4-azidophenyl)-5-oxo-2-hydroisoxazol-2-yl]methyl}acetamide)

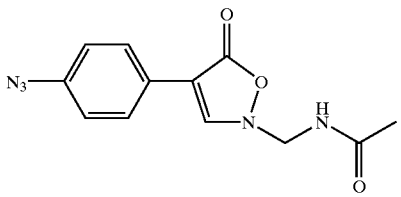

Prepared from ethyl 4-azidophenylacetate according to the general route outlined in Scheme 1. The starting material was prepared as follows:

Ethyl 4-Azidophenylacetate

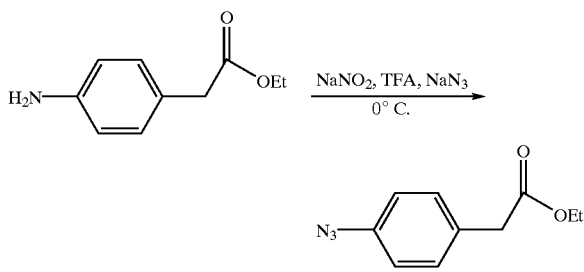

Following the general procedure of Marchesini (*J. Org. Chem.* 49, p. 4287–4290, 1984), sodium nitrite (38 g, 0.56 mol) was slowly added to a stirred and cooled (0° C.) mixture of ethyl 4-aminophenylacetate (25 g, 0.14 mol) in 700 mL of TFA. After the addition was complete, the reaction was stirred at 0° C. for another 0.5 hour and then sodium azide (27 g, 0.42 mol) was slowly added over a period of 0.5 hours. The mixture was stirred for another 2 hours at 0° C. and then quenched with ice water and the product was extracted with EtOAc. The organic phase was washed with water, dried over magnesium sulfate, filtered, concentrated to yield 26.5 g (90%) of the title compound as a white solid. $^1$H NMR (300 MHz, DMSO-$d_6$) δ7.31 (d, J=8 Hz, 2H), 7.07 (d, J=7 Hz, 2H), 4.07 (q, J=7 Hz, 2H), 3.66 (s, 2H), 1.17 (t, J=7 Hz, 3H).

Example 16

N-[(4-{4-[4-(hydroxymethyl)(1,2,3-triazolyl)]phenyl}-5-oxo-2-hydroisoxazol-2-yl)methyl]acetamide

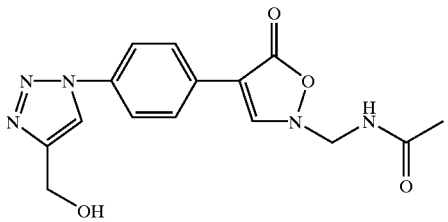

A mixture of N-{[4-(4-azidophenyl)-5-oxo-2-hydroisoxazol-2-yl]methyl}acetamide (80 mg, 0.29 mmol) and propargyl alcohol (0.1 mL, 1.71 mmol) in 3 mL of DMF was heated at 100° C. for 10 hours. The reaction mixture was then concentrated in vacuo and purified by flash chromatography (silica gel; eluting with EtOAc followed by 10% MeOH/EtOAc) to yield 62 mg of a yellow solid. The $^1$H NMR spectra indicated that the crude product was a mixture of two triazole isomers. These isomers were separated by preparative HPLC (H$_2$O/MeOH) to yield 10 mg (10%) of the title compound as a white solid. $^1$H NMR (300 MHz, DMSO-$d_6$) δ9.11 (s, 1H), 8.96, (t, J=6 Hz, 1H), 8.69, (s, 1H), 7.96 (m, 4H), 5.07 (d, J=6 Hz, 2H), 4.61 (s, 2H), 1.86 (s, 3H).

Example 17

Methyl 1-(4-{2-[(acetylamino)methyl]-5-oxo-2-hydroisoxazol-4-yl}phenyl)-1,2,3-triazole-4-carboxylate

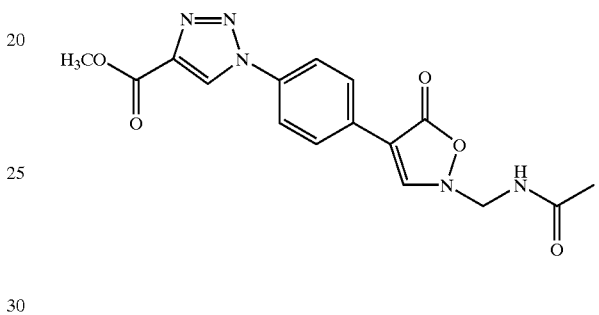

A mixture of N-{[4-(4-azidophenyl)-5-oxo-2-hydroisoxazol-2-yl]methyl}acetamide (80 mg, 0.29 mmol) and methyl propionate (0.05 mL, 0.58 mmol) in 3 mL DMF was heated at 50° C. for 24 hours. The reaction mixture was then concentrated in vacuo and triturated with EtOAc to yield 25 mg (24%) of the title compound as a yellow solid. (An alternate procedure which is more reliable involves conducting the reaction at room temperature for 10 days and then isolating as above.) $^1$H NMR (300 MHz, DMSO-$d_6$) δ9.52 (s, 1H), 9.15, (s, 1H), 8.96, (t, J=6 Hz, 1H), 8.02 (s, 4H), 5.08 (d, J=6 Hz, 2H), 3.90 (s, 3H), 1.87 (s, 3H).

Example 18

N-({4-[4-(4-acetyl(1,2,3-triazolyl))phenyl]-5-oxo-2-hydroisoxazol-2-yl}methyl)acetamide

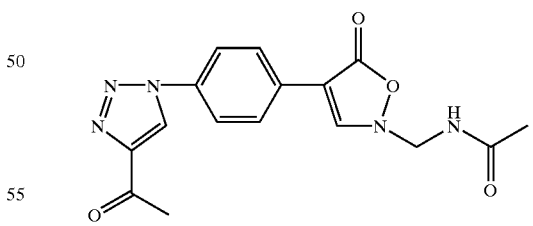

A mixture of N-{[4-(4-azidophenyl)-5-oxo-2-hydroisoxazol-2-yl]methyl}acetamide (100 mg, 0.36 mmol) and of 3-butyn-2-one (0.035 mL, 0.72 mmol) in 3 mL DMF was heated at 50° C. for 24 hours. The reaction mixture was concentrated in vacuo and then triturated with EtOAc to yield 60 mg (49%) of the title compound as a yellow solid. $^1$H NMR (300 MHz, DMSO-$d_6$) δ9.47 (s, 1H), 9.35, (s, 1H), 8.98, (t, J=6 Hz, 1H), 8.02 (s, 4H), 5.08 (d, J=6 Hz, 2H), 3.32 (s, 3H), 1.85 (s, 3H).

Example 19

N-({4-[4-(4-cyano(1,2,3-triazolyl))phenyl]-5-oxo-2-hydroisoxazol-2-yl}methyl)acetamide

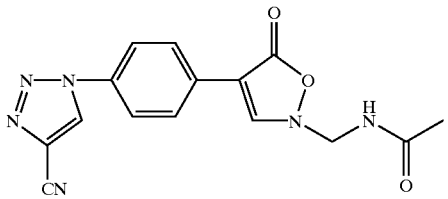

A mixture of N-{[4-(4-azidophenyl)-5-oxo-2-hydroisoxazol-2-yl]methyl}acetamide (500 mg, 1.83 mmol) and 0.8 mL of cyanoacetylene [prepared according to Murahashi, S.; Takizawa, T.; Kurioka, S.; Maekawa, S.; in *J. Chem. Soc. Jap.*, 77, p, 1689,1956] in 5 mL of DMF was heated at 50° C. for 48 hours. Upon cooling, the precipitated solid was collected by filtration and washed with DMF to yield 375 mg (63%) of the title compound as a white solid. $^1$H NMR (300 MHz, DMSO-$d_6$) δ9.75 (s, 1H), 9.17, (s, 1H), 9.00, (t, J=6 Hz, 1H), 8.05 (d, J=9 Hz, 2H), 7.95 (d, J=9 Hz, 2H), 5.10 (d, J=6 Hz, 2H), 1.85 (s, 3H).

Example 20

N-{[4-(4-aminophenyl)-5-oxo-2-hydroisoxazol-2-yl]methyl}acetamide

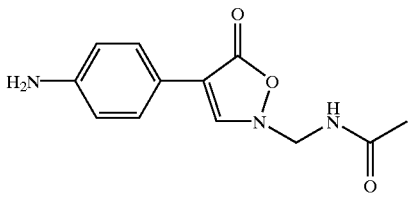

To a mixture of N-{[4-(4-azidophenyl)-5-oxo-2-hydroisoxazol-2-yl]methyl}acetamide (3 g, 10.98 mmol) in 40 mL EtOAc and 20 mL MeOH was added SnCl$_2$.2H$_2$O (12.5 g, 54.9 mmol). After all of the solid was dissolved, the reaction mixture was concentrated in vacuo and neutralized with saturated aqueous sodium bicarbonate. The mixture was concentrated in vacuo again and the residue was dissolved in a mixture of 4:1 CHCl$_3$/MeOH. The resulting solution was filtered throuth celite, and the insoluble material was discarded. The filtrate was then concentrated in vacuo to yield 3 g (100%) of the title compound as a yellow solid. $^1$H NMR (300 MHz, DMSO-$d_6$) δ8.83, (t, J=6 Hz, 1H), 8.55, (s, 1H), 7.43 (d, J=9 Hz, 2H), 6.56 (d, J=9 Hz, 2H), 5.21, (broad s, 2H), 4.91 (d, J=6 Hz, 2H), 1.82 (s, 3H).

Example 21

N-({4-[4-(3-formylpyrrolyl)phenyl]-5-oxo-2-hydroisoxazol-2-yl}methyl)acetamide

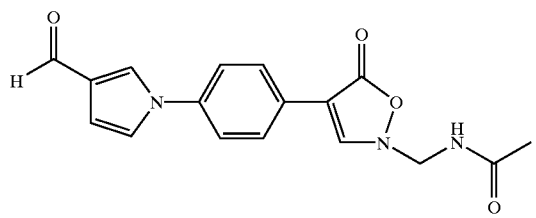

To a solution of N-{[4-(4-aminophenyl)-5-oxo-2-hydroisoxazol-2-yl]methyl}acetamide (200 mg, 0.81 mmol) in 3 mL of acetic acid was added 2,5-dimethoxy-3-tetrahydrofurancarboaldehyde (184 mg, 1.27 mmol). This mixture was refluxed for 0.5 hours, and then concentrated in vacuo to give the crude product. Purification by silica gel chromatography (eluting with EtOAc, then 8% MeOH in EtOAc) gave 240 mg (91%) of the title compound as a yellow solid. $^1$H NMR (300 MHz, DMSO-$d_6$) δ9.79 (s, 1H), 9.08, (s, 1H), 9.00, (t, J=6 Hz, 1H), 8.29, (m, 1H), 7.93 (d, J=9 Hz, 2H), 7.74 (d, J=9 Hz, 2H), 7.58, (m, 1H), 6.71 (m, 1H), 5.06 (d, J=6 Hz, 2H), 1.86 (s, 3H).

Example 22

N-{[5-oxo-4-(4-pyrrolylphenyl)-2-hydroisoxazol-2-yl]methyl}acetamide

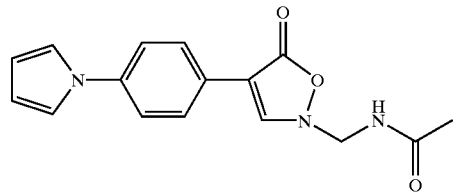

This compound was prepared from N-{[4-(4-aminophenyl)-5-oxo-2-hydroisoxazol-2-yl]methyl}acetamide as described above for N-({4-[4-(3-formylpyrrolyl)phenyl]-5-oxo-2-hydroisoxazol-2-yl}methyl)acetamide except that 2,5-dimethoxy-3-tetrahydrofuran was used in place of 2,5-dimethoxy-3-tetrahydrofurancarboaldehyde. $^1$H NMR (300 MHz, DMSO-$d_6$) δ8.92, (s, 1H), 8.94, (t, J=6 Hz, 1H), 7.85 (d, J=9 Hz, 2H), 7.62 (d, J=9 Hz, 2H), 7.40, (t, J=2 Hz, 2H), 6.27 (t, J=2 Hz, 2H), 5.04 (d, J=6 Hz, 2H), 1.86 (s, 3H).

Example 23

N-[(4-{4-[3-((hydroxyimino)methyl)pyrrolyl]phenyl}-5-oxo-2-hydroisoxazol-2-yl)methyl]acetamide

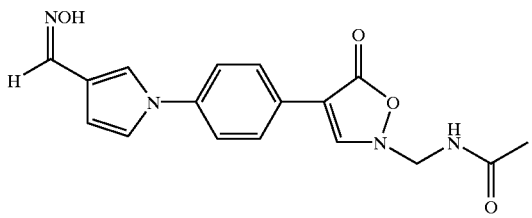

A mixture of N-({4-[4-(3-formylpyrrolyl)phenyl]-5-oxo-2-hydroisoxazol-2-yl}methyl)acetamide (100 mg, 0.30 mmol) and 50% aqueous NH₂OH (40 mg, 0.60 mmol) in 3 mL of MeOH was heated at reflux for 2 hours. The reaction mixture was then concentrated in vacuo and the residue was triturated with ether to yield 96 mg (94%) of the title compound as a yellow solid. $^1$H NMR (300 MHz, DMSO-d$_6$) δ10.6 (s, 1H), 9.02, (s, 1H), 8.95, (t, J=6 Hz, 1H), 8.00, (s, 1H), 7.87 (d, J=9 Hz, 2H), 7.66, (s, 1H), 7.63 (d, J=9 Hz, 2H), 7.45, (m, 1H), 6.50 (m, 1H), 5.04 (d, J=6 Hz, 2H), 1.85 (s, 3H).

Example 24 t-Butyl 4-(4-{2-[(acetylamino)methyl]-5-oxo-2-hydroisoxazol-4-yl}phenyl)piperazine carboxylate

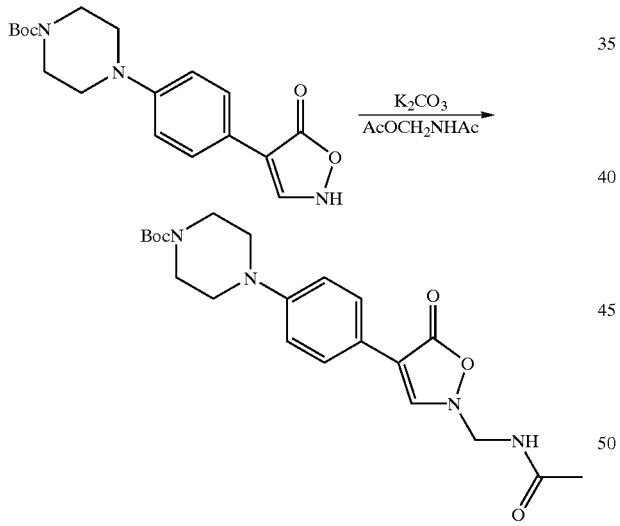

To t-butyl 4-[4-(5-oxo-2-hydroisoxazol-4-yl)phenyl]piperazinecarboxylate (1.5 g, 4.3 mmol) in 35 mL dimethylformamide was added N-(hydroxymethyl)acetamide acetate (2.9 g, 22.0 mmol) followed by potassium carbonate (3.0 g, 22.0 mmol). After 5 hours the reaction mixture was poured into ice water. After 18 hours the precipitate was filtered and dried in vacuo to provide 1.4 g (77%) of the title compound. $^1$H NMR (methanol-d₄; 300 MHz) δ8.48 (s, 1H), 7.66 (d, J=8.8 Hz, 2H), 7.01 (d, J=8.8 Hz, 2H), 5.07 (s, 2H), 3.58 (t, J=4.8 Hz, 4H), 3.17 (t, J=5.2 Hz, 4H), 1.94 (s, 3H), 1.50 (s, 9H); ESI (M+H)⁺=417.

The starting materials were prepared as follows:

Methyl 2-(4-{4-[(t-butyl)oxycarbonyl]piperazinyl}phenyl)acetate

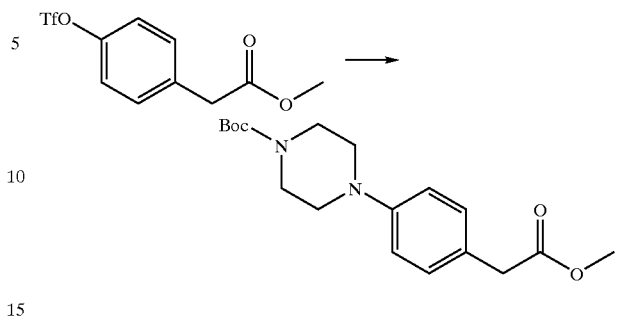

A flask charged with cesium carbonate (4.6 g, 14.0 mmol), palladium (II) acetate (0.07 g, 0.3 mmol), and (S)-BINAP (0.28 g, 4.5 mmol) was evacuated and flushed with dry nitrogen. Methyl 2-{4-[(trifluoromethyl)sulfonyloxy]phenyl}acetate (3.0 g, 10.0 mmol) and t-butyl-1-piperazinecarboxylate (2.3 g, 12.0 mmol) in 20 mL toluene was added via syringe and the resultant mixture was stirred at ambient temperature for 30 minutes and at 80° C. for 16 hours. The reaction mixture was removed from the heating bath, concentrated, and chromatographed on silica gel (0 to 30% ethyl acetate/hexane) providing 1.7 g (50%) of the title compound. $^1$H NMR (300 MHz, CDCl₃) δ7.20 (d, J=8.5 Hz, 2H), 6.89 (d, J=8.4 Hz, 2H), 3.70 (s, 3H), 3.59 (t, J=5.0 Hz, 4H), 3.57 (s, 2H), 3.12 (t, J=5.2 Hz, 4H), 1.50 (s, 9H); ESI (M+H)⁺=335.

Ethyl 2-(4-{4-[(t-butyl)oxycarbonyl]piperazinyl})phenyl)-3-oxopropanoate

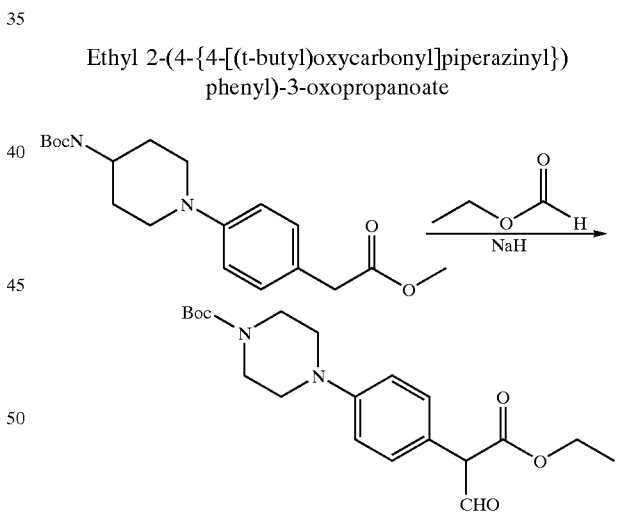

To methyl 2-(4-{4-[(t-butyl)oxycarbonyl]piperazinyl}phenyl)acetate (0.67 g, 2.0 mmol) in 8 mL ethyl formate was added sodium hydride (60% dispersion in mineral oil) (0.32 g, 8.0 mmol) portionwise. After 1.5 hours, the reaction mixture was poured into saturated sodium bicarbonate, and extracted three times with ether. The combined organic layers were washed with brine, dried over magnesium sulfate, filtered and concentrated. The crude product was used directly in the next step without further purification.

t-Butyl 4-[4-(5-oxo-2-hydroisoxazol-4-yl)phenyl]piperazinecarboxylate

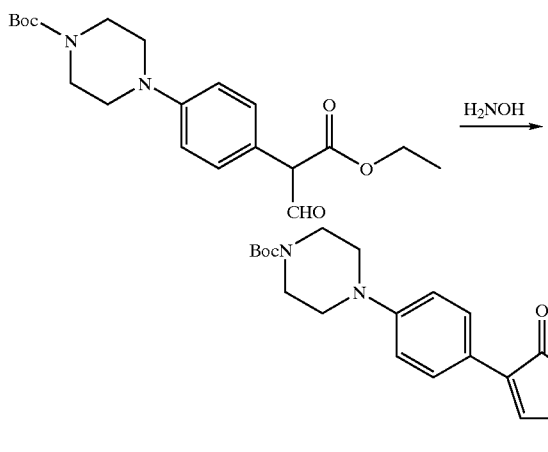

To ethyl 2-(4-{4-[(t-butyl)oxycarbonyl]piperazinyl})phenyl)-3-oxopropanoate (7.8 g, 20.7 mmol) in 140 mL methanol and 40 mL water was added hydroxylamine (50% in water, 3.0 mL, 49.0 mmol). The reaction mixture was heated to reflux for 3 hours, cooled and concentrated. The residue was triturated with water and the precipitate was filtered, dried and washed with ether to provide 4.3 g of the title compound. The aqueous solution was lyophilized providing an additional 1.5 g of the title compound. $^1$H NMR (methanol-$d_4$; 300 MHz) δ8.35 (s, 1H), 7.58 (br d, J=, 2H), 6.96 (d, J=8.2 Hz, 2H), 3.58 (t, J=4.6 Hz, 4H), 3.10 (br s, 4H), 1.50 (s, 9H); ESI (M+H)$^+$=345.

Example 25

N-{[5-oxo-4-(piperazinylphenyl)-2-hydroisoxazol-2-yl]methyl}acetamide trifluoroacetate salt

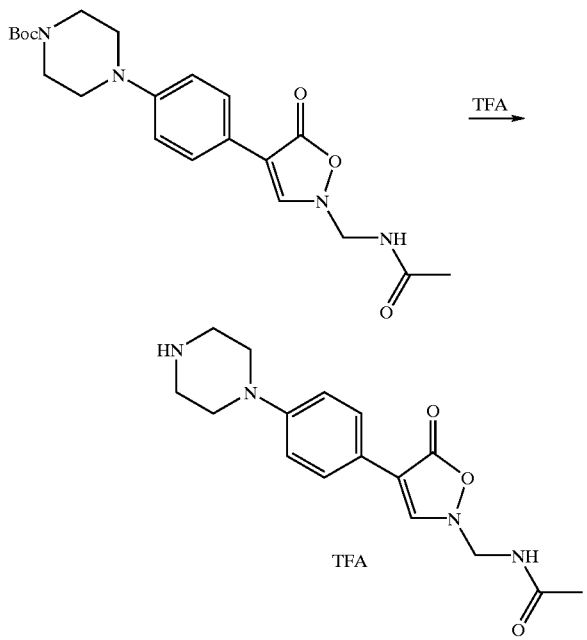

To t-butyl 4-(4-{2-[(acetylamino)methyl]-5-oxo-2-hydroisoxazol4-yl}phenyl)piperazine carboxylate (0.3 g, 0.7 mmol) in 5 mL dichloromethane was added 2 mL trifluoroacetic acid. After 30 minutes, the reaction mixture was concentrated and triturated with ether to provide 0.3 g (97%) of the title compound. $^1$H NMR (methanol-$d_4$; 300 MHz) δ9.00 (t, J=6.0 Hz, 1H), 8.23 (s, 1H), 7.70 (d, J=8.8 Hz, 2H), 7.05 (d, J=8.7 Hz, 2H), 5.08 (d, J=6.2 Hz, 2H), 3.45–3.38 (m, 8H), 1.95 (s, 3H); ESI (M+H)$^+$=317.

Example 26 tert-Butyl 4-(4-{2-[(acetylamino)methyl]-5-oxo(2-hydroisoxazol4-yl)}-2-fluorophenyl)piperazinecarboxylate

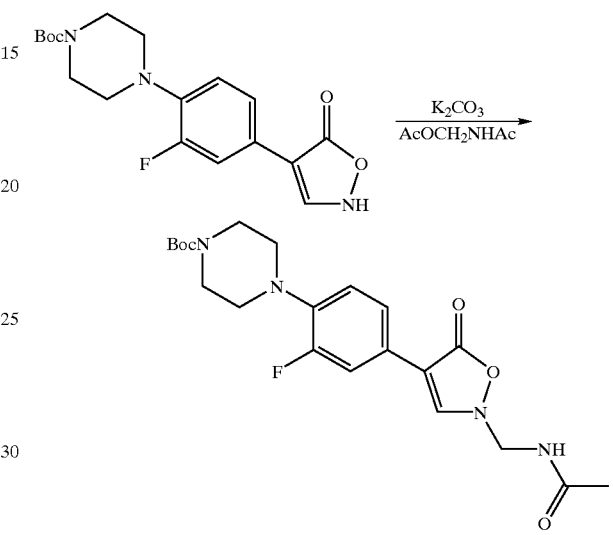

Prepared according to the general procedures outlined in Schemes 1, 3, and 6. The starting materials were prepared as follows:

2-(4-{4-[(t-butyl)oxycarbonyl]piperazinyl})-3-fluorophenyl)acetic acid

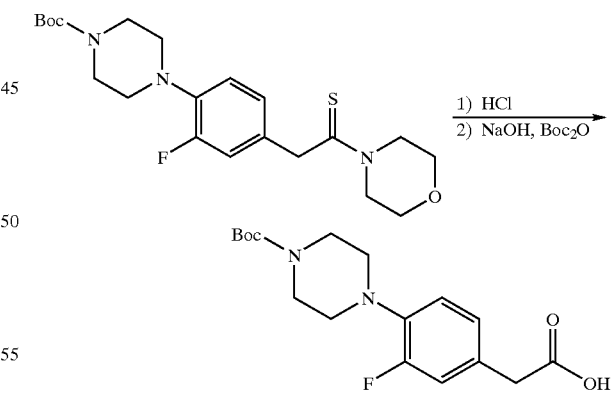

To t-butyl 4-[2-fluoro-4-(2-morpholin4-yl-2-thioxoethyl)phenyl]piperazinecarboxylate (4.2 g, 10 mmol) was added 22 mL of concentrated hydrochloric acid at 0° C. The resulting mixture was heated to reflux for 1.5 hours, cooled to 0° C., and 23 mL of 10N sodium hydroxide was added to bring the pH to 14. Then 50 mL water was added followed by di-t-butyl dicarbonate (5.6 g, 26.0 mmol) in 5 mL tetrahydrofuran. The resulting mixture was allowed to stir at 0° C. for 30 minutes and then for 1 hour at ambient temperature at which time it was diluted with 200 mL water. Then 5 mL sodium hydroxide was added to adjust the pH to 14, and the reaction mixture was extracted with ether. The aqueous layer was acidified to pH 3 by the careful addition of 6N hydrochloric acid and then extracted with three portions of ethyl acetate. The organic layer was washed with brine, dried over magnesium sulfate, and concentrated. The resultant residue was dissolved in dichloromethane and hexanes were added to produce a precipitate which was collected by filtration providing 3.0 g (89%) of the title product. $^1$H NMR (CDCl$_3$; 300 MHz) δ7.04–6.98 (m, 2H), 6.90 (t, J=8.3 Hz, 1H), 3.60 (m, 6H), 3.02 (t, J=5.0 Hz, 4H), 1.50 (s, 3H); ESI (M+H)$^+$=339.

Methyl 2-(4-{4-[(t-butyl)oxycarbonyl]piperazinyl}-3-fluorophenyl)acetate

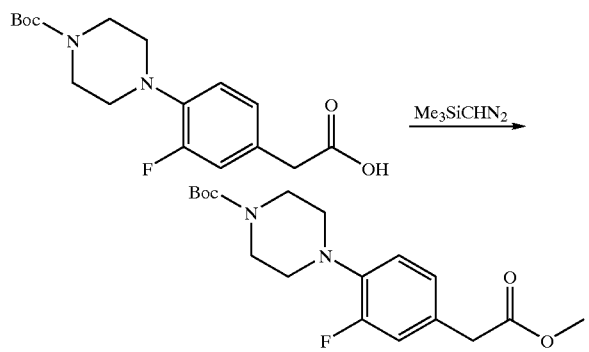

To 2-(4-{4-[(t-butyl)oxycarbonyl]piperazinyl}-3-fluorophenyl)acetic acid (0.3 g, 1.0 mmol) in 2 mL methanol and 7 mL benzene was added trimethylsilyidiazomethane (0.65 mL, 1.30 mmol). After stirring at ambient temperature for 1 hour, the reaction mixture was concentrated to provide 0.36 g (99%) of the title compound. $^1$H NMR (CDCl$_3$; 300 MHz) δ7.00 (m, 2H), 6.90 (t, J=8.3 Hz, 1H), 3.71 (s, 3H), 3.61 (t, J=4.9 Hz, 4H), 3.57 (s, 2H), 3.02 (t, J=5.0 Hz, 4H), 1.50 (s, 9H); ESI (M+H)$^+$=353.

Example 27

N-{[4-(4-morpholinylphenyl)-5-oxo-2-isoxazolinyl]methyl}acetamide

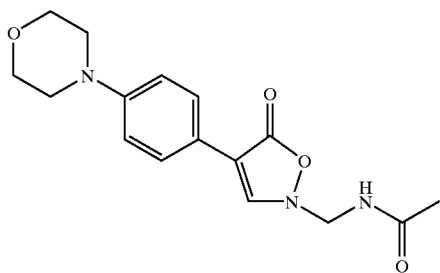

Prepared according to the general procedure outlined in Schemes 1 and 2. The starting materials were prepared as follows:

Methyl-4-(trifluoromethylsulfonyloxy)phenyl acetate

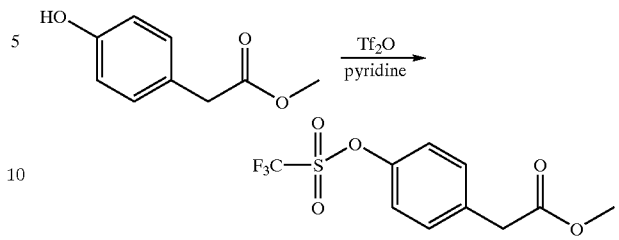

To methyl-4-hydroxyphenyl acetate (20 g, 120 mmol) and pyridine (20 mL, 240 mmol) in 100 mL dichloromethane at 0° C. was added trifluoromethanesulfonic anhydride (23 mL, 132 mmol) dropwise over 30 minutes. After an additional 30 minutes at 0° C. followed by 30 minutes at ambient temperature, 1N hydrochloric acid was added and the reaction mixture was extracted into dichloromethane. The organic layer was washed with 1N hydrochloric acid, saturated sodium bicarbonate, brine, dried over magnesium sulfate, filtered, and concentrated providing 32 g (90%) of the title compound as a yellow solid. $^1$H NMR (CDCl$_3$; 300 MHz) δ7.38 (d, J=8.4 Hz, 2H), 7.24 (d, J=8.5 Hz, 2H), 3.72 (s, 3H), 3.66 (s, 2H).

Methyl-4-morpholinophenyl acetate

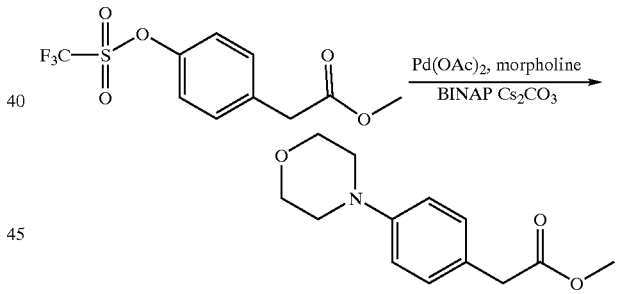

Nitrogen was bubbled through a mixture of methyl4-(trifluoromethylsulfonyloxy)phenyl acetate (1.0 g, 3.35 mmol), cesium carbonate (1.6 g, 4.69 mmol), palladium (II) acetate (22 mg, 0.10 mmol), (S)-BINAP (93 mg, 0.15 mmol), and morpholine (0.35 mL, 4.02 mmol) in 8 mL toluene and the reaction mixture was heated to 80° C. for 6 hours. The reaction was then cooled, celite was added, and the mixture was concentrated. Chromatography was performed on a Biotage flash 40i chromatography module by loading the dried celite into a SIM and eluting with 20% ethyl acetate/hexanes (40S cartridge) providing 250 mg (37%) of the title compound as a yellow oil. $^1$H NMR (CDCl$_3$; 300 MHz) δ7.19 (d, J=8.4 Hz, 2H), 6.87 (d, J=8.3 Hz, 2H), 3.89–3.85 (m, 4H), 3.69 (s, 3H), 3.56 (s, 2H), 3.17–3.13 (m, 4H).

Example 28

N-{[4-(4-(1,4-thiazaperhydroin-4-yl)phenyl)-5-oxo-2-hydroisoxazol-2-yl]methyl}acetamide

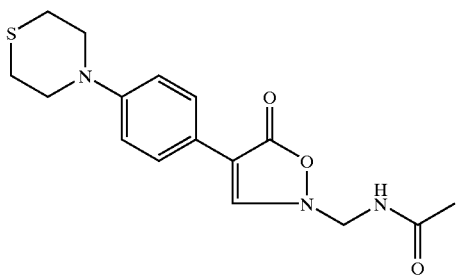

Prepared according to the general procedures outlined in Schemes 1 and 3. The starting materials were prepared as follows:

4-Thiomorpholinoacetophenone

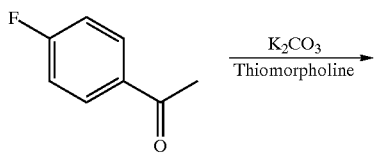

To 4-fluoroacetophenone (20 g, 145 mmol) in 100 mL dimethylformamide was added potassium carbonate (39 g, 580 mmol) followed by thiomorpholine (87 mL, 870 mmol). The reaction mixture was heated to reflux and after 24 hours, it was cooled to ambient temperature and partitioned between water and dichloromethane. The organic layer was dried over magnesium sulfate, filtered, and concentrated. The residue was dissolved in ether and precipitated with hexanes providing 31 g (96%) of the title compound as a yellow solid. $^1$H NMR (CDCl$_3$; 300 MHz) $\delta$7.87 (d, J=9.0 Hz, 2H), 6.82 (d, J=9.0 Hz, 2H), 3.81–3.78 (m, 4H), 2.73–2.69 (m, 4H), 2.53 (s, 3H).

4-Thiomorpholinophenylthioacetomorpholide

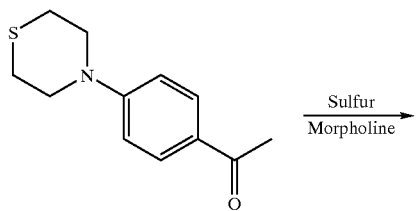

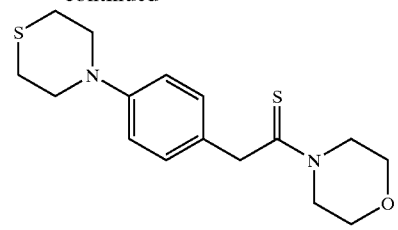

A mixture of 4-thiomorpholinoacetophenone (30 g, 136 mmol), morpholine (16 mL, 180 mmol) and sulfur (6 g, 180 mmol) was heated to reflux for 6 hours, cooled to 50° C., and 100 mL 1:1 hexanes:ethyl acetate was added. The reaction mixture was again brought to reflux for 30 minutes, cooled, and the resultant orange precipitate was collected via filtration. The precipitate was washed with additional 1:1 ether/hexanes providing 31 g (73%) of the title compound as a yellow-orange solid. $^1$H NMR (CDCl$_3$; 300 MHz) $\delta$7.21 (d, J=8.7 Hz, 2H), 6.86 (d, J=8.1 Hz, 2H), 4.35 (t, J=4.8 Hz, 2H), 4.27 (s, 2H), 3.74 (t, J=4.8 Hz, 2H), 3.65 (t, J=4.2 Hz, 2H), 3.52 (t, J=5.1 Hz, 4H), 3.41 (t, J=5.4 Hz, 2H), 2.77–2.71 (m, 2H).

Ethyl-4-thiomorpholinophenyl acetate

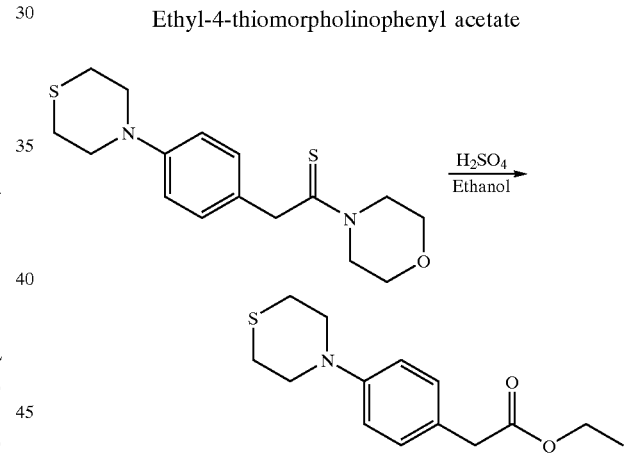

A solution of 4-thiomorpholinophenylthioacetomorpholide (30 g, 93.2 mmol) in 70 mL 1:1 ethanol:sulfuric acid was heated to reflux for 18 hours, cooled to room temperature and solid sodium bicarbonate was slowly added to the reaction until it reached pH 7. The reaction mixture was extracted with chloroform, and the organic layer was washed with brine, dried over magnesium sulfate, filtered, and concentrated to a yellow residue. The residue was then dissolved in chloroform, loaded onto a Biotage flash 40i chromatography module (40M cartridge) and chromatographed with 10% ethyl acetate/hexanes providing 12 g (51%) of the title compound as a yellow oil. $^1$H NMR (CDCl$_3$; 300 MHz) $\delta$7.18 (d, J=8.7 Hz, 2H), 6.86 (d, J=8.6 Hz, 2H), 4.14 (q, J=7.2 Hz, 2H), 3.54–3.50 (m, 6H), 2.76–2.73 (m, 4H), 1.25 (t, J=7.2 Hz, 3H).

Example 29

N-{[4-(3-fluoro-4-methylthiophenyl)-5-oxo-2-hydroisoxazol-2-yl]methyl}acetamide

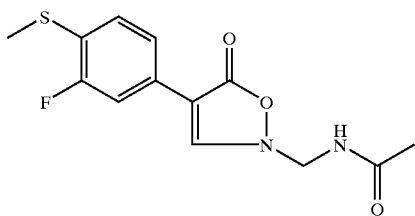

Prepared according to the general procedures outlined in Schemes 1 and 3. The starting materials were prepared as follows:

3-Fluoro-4-methylthioacetophenone

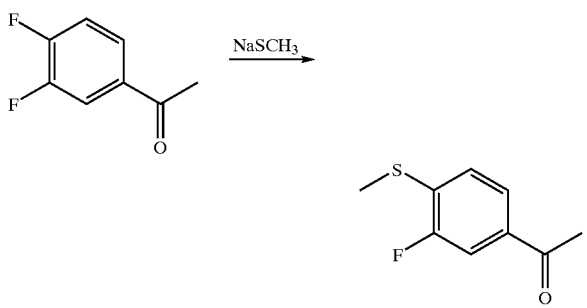

To 3,4-difluoroacetophenone (30 g, 192 mmol) in 200 mL dimethylsulfoxide was added sodium thiomethoxide (15 g, 211 mmol). The reaction mixture was heated to 150° C. for 2 hours and then partitioned between ethyl acetate and sodium bicarbonate. The organic layer was washed with brine, dried over magnesium sulfate, filtered, and concentrated. The residue was dissolved in ethyl acetate and precipitated with hexanes. The precipitate was collected by filtration providing 25 g (70%) of the title compound as a yellow solid.

3-Fluoro-4-methylthiophenylthioacetomorpholide

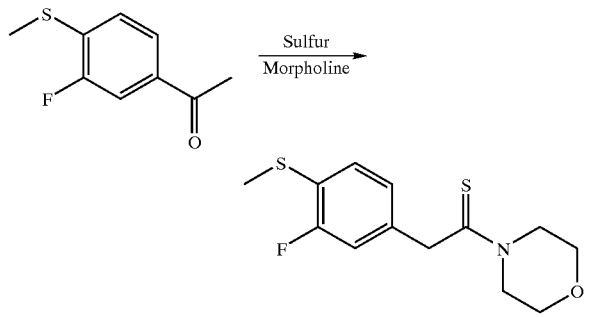

A mixture of 3-fluoro4-methylthioacetophenone (9.0 g, 48.9 mmol), morpholine (5.7 mL, 65.0 mmol), and sulfur (2.1 g, 65.0 mmol) were heated to reflux for 4 hours, cooled to 50° C., and 1:1 hexanes:ethyl acetate was added. The reaction mixture was again heated to reflux for 30 minutes, cooled to ambient temperature, and the resultant orange precipitate was collected by filtration. The precipitate was washed with 1:1 hexanes:ether providing 10.1 g (73%) of the title compound as a yellow-orange solid. $^1$H NMR (DMSO-d$_6$; 300 MHz) δ7.36–7.29 (m, 1H), 7.20–7.15 (m, 2H), 4.27 (s, 2H), 4.22 (t, J=4.8 Hz, 2H), 3.73 (t, J=4.5 Hz, 2H), 3.65 (t, J=4.8 Hz, 2H), 3.47 (t, J=5.1 Hz, 2H), 2.47 (s, 3H).

3-Fluoro-4-methylthiophenylacetic acid

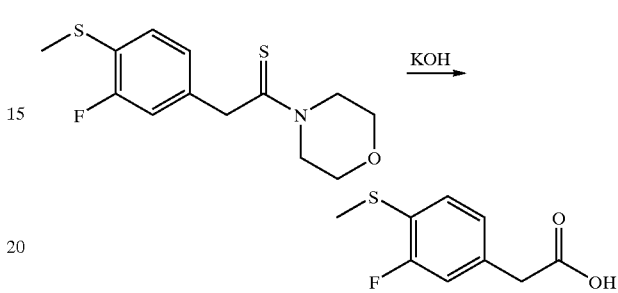

To 3-fluoro-4-methylthiophenylthioacetomorpholide (2.6 g, 90.9 mmol) was added 500 mL 10% potassium hydroxide. The reaction mixture was heated to reflux for 3 hours, cooled to ambient temperature, and adjusted to pH 4 by the careful addition of 2N hydrochloric acid. The aqueous solution was extracted with dichloromethane and the organic layer was then extracted with 200 mL 10% potassium hydroxide. The aqueous layer was then brought to pH 4 by the careful addition of 2N hydrochloric acid and extracted with dichloromethane. The organic layer was dried over magnesium sulfate, filtered, and concentrated providing 10.0 g (55%) of the title compound as a brown oil. $^1$H NMR (CDCl$_3$; 300 MHz) δ7.24–7.21 (m, 1H), 7.04–6.99 (m, 2H), 3.63 (s, 2H), 2.46 (s, 3H).

Example 30

N-{[4-(3-fluoro-4-methoxyphenyl)-5-oxo-2-hydroisoxazol-2-yl]methyl}acetamide

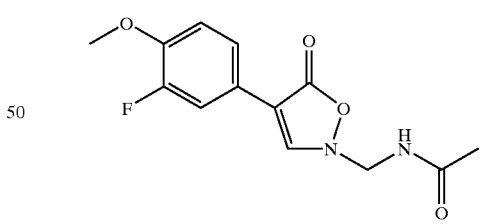

Prepared according to the general procedure outlined in Schemes 1. The starting material was prepared as follows:

Ethyl-(3-Fluoro-4-methoxy)phenyl acetate

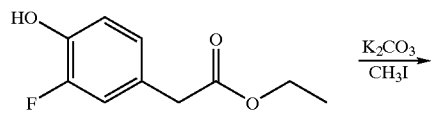

-continued

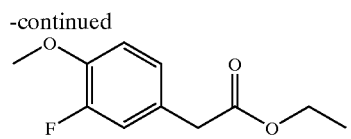

To ethyl-(3-fluoro4-hydroxy)phenyl acetate (2.5 g, 8.9 mmol) in 20 mL acetone was added potassium carbonate (3.4 g, 24.2 mmol) and iodomethane (1.5 mL, 24.2 mmol). The reaction mixture was heated to reflux for 2 hours, cooled, and partitioned between saturated sodium bicarbonate and ether. The organic layer was washed with brine, dried over magnesium sulfate, filtered and concentrated providing 2.3 g (88%) of the title compound as a yellow oil. $^1$H NMR (CDCl$_3$; 300 MHz) δ7.06–6.88 (m, 3H), 4.15 (q, J=7.2 Hz, 2H), 3.88 (s, 3H), 3.54 (s, 2H), 1.26 (t, J=7.2 Hz, 3H).

Example 31

N-({4-[4-(3-cyanopyrrolyl)phenyl]-5-oxo-2-hydroisoxazol-2-yl}methyl)acetamide

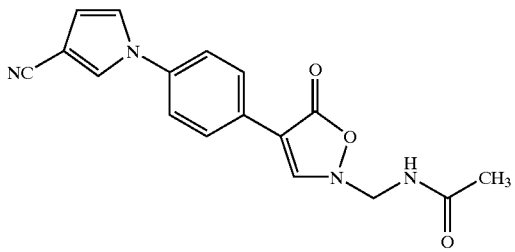

To a mixture of N-[(4-{4-[3-((hydroxyimino)methyl)pyrrolyl]phenyl}-5-oxo-2-hydroisoxazol-2-yl)methyl]acetamide (100 mg, 0.29 mmol) in 3 ml of CH$_3$CN and 1 ml of CCl$_4$ was added polymer-bound triphenylphosphine (400 mg, 1.2 mmol) and the mixture was heated at reflux for 8 hours. It was then dissolved in ethyl acetate, filtered, and concentrated to yield a yellow solid. This solid was then triturated with ether to obtain 30 mg (32%) of the title compound as a yellow solid. $^1$H NMR (300 MHz, DMSO-d$_6$) δ9.08 (s, 1H), 8.97 (t, J=6 Hz, 1H), 8.28, (s, 1H), 7.92 (d, J=9 Hz, 2H), 7.70 (d, J=9 Hz, 2H), 7.59 (m, 1H), 6.74 (m, 1H), 5.06 (d, J=6 Hz, 2H), 1.86 (s, 3H).

Example 32

N-[(4-{4-[3-((1E)-2-aza-2-methoxyvinyl)pyrrolyl]phenyl}-5-oxo-2-hydroisoxazol-2-yl)methyl]acetamide

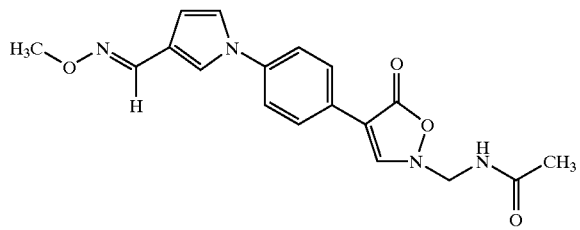

A mixture of N-({4-[4-(3-formylpyrrolyl)phenyl]-5-oxo-2-hydroisoxazol-2-yl}methyl)acetamide (100 mg, 0.3 mmol), HCl.NH$_2$OCH$_3$ (31 mg, 0.37 mmol) and sodium carbonate (20 mg, 0.19 mmol) was dissolved in 3 mL of MeOH and 2 mL of water. To this mixture was added acetic acid to adjust the pH to 5. The reaction was heated at reflux for 1 hour. The reaction was cooled to room temperature, and the yellow precipitate was collected by filtration to give 40 mg (36%) of the title compound as a yellow solid. (M+H$^+$)=355.

Example 33

N-{[4-(4-{3-[(1E)-2-(acetylamino)-2-azavinyl]pyrrolyl}phenyl)-5-oxo-2-hydroisoxazol-2-yl]methyl}acetamide

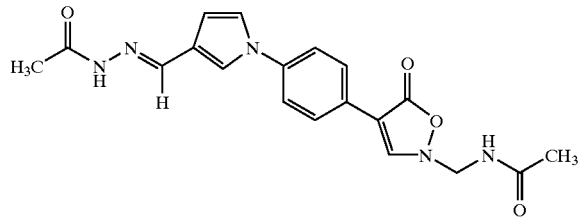

A mixture of N-({4-[4-(3formylpyrrolyl)phenyl]-5-oxo-2-hydroisoxazol-2-yl]methyl)acetamide (100 mg, 0.30 mmol) and acetic hydrazide (28 mg, 0.38 mmol) in 3 mL of EtOH was heated at reflux for 1 hour. The reaction was cooled to room temperature, and the yellow precipitate was collected by filtration to give 80 mg (36%) of the title compound. (M+H$^+$)=382.

Example 34

Ethyl 1-(4-{2-[(acetylamino)methyl]-5oxo-2-hydroisoxazol4-yl}phenyl)pyrazole-4-carboxylate

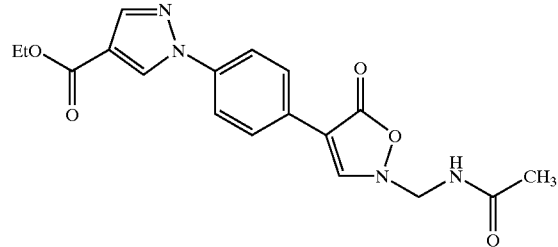

To a mixture of N-{[4-(4-hydrazinylphenyl)-5-oxo-2-hydroisoxazol-2-yl]methyl}acetamide hydrochloride (150 mg, 0.5 mmol) in 3 mL of methanol was added sodium bicarbonate (50 mg, 0.6 mmol) and ethoxycarbonylmalondialdehyde (75 mg, 0.52 mmol). The mixture was stirred at room temperature overnight. The solid was collected by filtration and then washed with water, and dried to yield 140 mg of a purple solid. The crude product was subjected to silica gel chromatography (eluting with ethyl acetate followed by 5% methanol/ethyl acetate) to yield 123 mg (66%) of the title compound as a yellow solid. $^1$H NMR (300 MHz, DMSO-d$_6$) δ9.11 (s, 1H), 9.08 (s, 1H), 8.96 (t, J=6 Hz, 1H), 8.15 (s, 1H), 7.95 (m, 4H), 5.06 (d, J=6 Hz, 2H), 4.28, (q, J=7 Hz, 2H), 1.86 (s, 3H), 1.31 (t, J=7 Hz, 3H).

The starting material, N-{[4-(4-hydrazinylphenyl)-5-oxo-2-hydroisoxazol-2-yl]methyl}acetamide hydrochloride, was prepared as follows. Sodium nitrite (112 mg, 1.6 mmol) in 2 mL of water was added to a solution of N-{[4-(4-aminophenyl)-5-oxo-2-hydroisoxazol-2-yl]

methyl}acetamide (400 mg, 1.6 mmol) in concentrated hydrochloric acid at 0° C. over 5 minutes. The reaction was stirred for an additional 10 minutes at 0° C., and then SnCl$_2$.2H$_2$O (720 mg, 3.2 mmol) in 2 mL of concentrated hydrochloric acid was added. This mixture was stirred at room temperature for 3 hours. The reaction mixture was then filtered to collect a yellow solid which was washed with 3 mL of water and dried to yield 260 mg (55%) of the title compound. $^1$H NMR (300 MHz, DMSO-d$_6$) δ10.2 (s, 2H), 8.94 (t, J=6 Hz, 1H), 8.82, (s, 1H), 8.35 (s, 1H), 7.70 (d, J=9, 2H), 6.99 (d, J=9, 2H), 4.99 (d, J=6 Hz, 2H), 1.84(s, 3H).

Example 35

N-({4-[4-(4-cyanopyrazolyl)phenyl]-5oxo-2-hydroisoxazol-2-yl)}methyl)acetamide

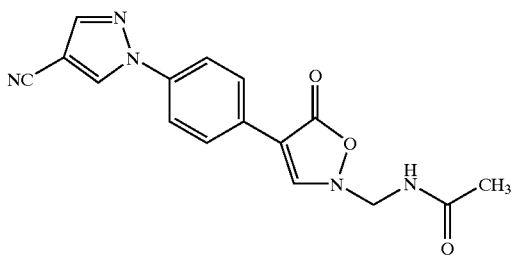

To a mixture of N-{[4-(4-hydrazinylphenyl)-5-oxo-2-hydroisoxazol-2-yl]methyl}acetamide hydrochloride (50 mg, 0.17 mmol) in 2 mL of methanol was added 20 mg (0.24 mmol) of sodium bicarbonate and cyanomalondialdehyde (30 mg, 0.3 mmol). The mixture was stirred at room temperature overnight. It was then concentrated to give a solid which was washed with water then methanol to give 42 mg (76%) of the title compound as a yellow solid. $^1$H NMR (300 MHz, DMSO-d$_6$) δ9.35 (s, 1H), 9.10 (s, 1H), 8.98 (t, J=6 Hz, 1H), 8.37 (s, 1H), 7.93 (m, 4H), 5.07 (d, J=6 Hz, 2H), 1.86 (s, 3H).

Preparation of cyanomalondialdehyde. To a dried flask was added sodium hydride (0.82 g, 50% suspended in mineral oil, 17 mmol). The sodium hydride was washed three times with 15 mL of ether, and then 15 mL of ether was added to the flask. After cooling the slurry to 0° C., ethyl formate (10.4 g, 140 mmol) was added. To this mixture was added 3,3-diethoxypropionitrile (2 g, 14 mmol) in 10 ml of ether over 2 hours (syringe pump). The mixture was stirred at room temperature for 20 hours, and then poured into 100 mL of ice water. This solution was extracted three times with ether, and then the ether extracts were discarded. The aqueous phase was acidified to pH 3 with concentrated HCl and extracted with dichloromethane. The organic phase was dried over MgSO$_4$, filtered, and concentrated to yield 0.3 g of cyanomalondialdehyde as a yellow solid. Additional product was recovered from the pH 3 aqueous phase: the aqueous phase was concentrated to dryness, and then dissolved in 5 mL of methanol. The inorganic salt was removed by filtration, and the filtrate was concentrated to yield 1 g of cyanomalondialdehyde as a yellow solid. $^1$H NMR (300 MHz, DMSO-d$_6$) δ8.94 (s, 2H), 4.95 (br s, 1H).

Example 36

N-{[5-oxo-4(4-pyrazolylphenyl)-2-hydroisoxazol-2-yl]methyl}acetamide

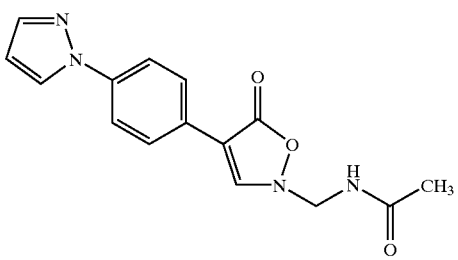

To a mixture of N-{[4-(4-hydrazinylphenyl)-5-oxo-2-hydroisoxazol-2-yl]methyl}acetamide hydrochloride (100 mg, 0.33 mmol) in 3 mL of methanol was added sodium bicarbonate (28 mg, 0.33 mmol) and malondialdehyde (50 mg, 0.35 mmol). The mixture was stirred at room temperature overnight. It was then concentrated to yield 120 mg of a yellow oil, which was then purified by silica gel chromatography (eluting with ethyl acetate) to obtain 30 mg (30%) of the title compound as a yellow solid. $^1$H NMR (300 MHz, DMSO-d$_6$) δ9.03 (s, 1H), 8.95 (t, J=6 Hz, 1H), 8.52 (s, 1H), 7.88 (m, 4H), 7.75 (s, 1H), 6.56 (s, 1H), 5.05 (d, J=6 Hz, 2H), 1.86 (s,3H).

The table below shows the chemical structures, characterizing properties (MS data) and preparative method for several representative compounds of the present invention, including those of Examples 1–36 described above.

| | Structure | MS data | Prepared via Scheme(s) |
|---|---|---|---|
| 1 | H$_3$CS-[structure] | (M + H)+ = 279 ESI | 1 |

-continued

| Structure | MS data | Prepared via Scheme(s) |
|---|---|---|
| 2 | (M + H)+ = 352<br>DCI | 3, 1 |
| 3 | (M + H)+ = 295<br>ESI | 1, 4 |
| 4 | (M + H)+ = 311<br>ESI | 1, 4 |
| 5 | (M + H)+ = 384<br>ESI | 3, 1, 4 |
| 6 | (M + H)+ = 352<br>ESI | 3, 1, 9 |
| 7 | (M + H)+ = 275<br>ESI | 1 |

-continued
| Structure | MS data | Prepared via Scheme(s) |
|---|---|---|
| 8 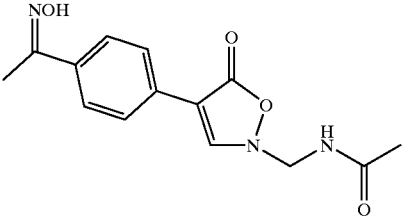 | (M + H)+ = 290 ESI | 1 |
| 9 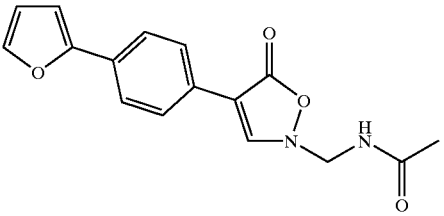 | (M + H)+ = 299 ESI | 1, 5 |
| 10 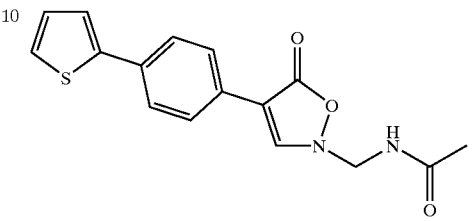 | (M + H)+ = 315 ESI | 1, 5 |
| 11 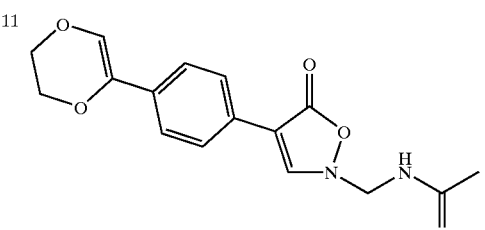 | (M + H)+ = 317 ESI | 1, 5 |
| 12 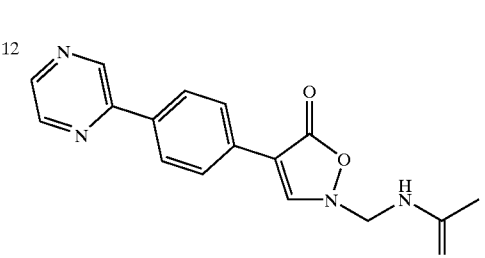 | (M + H)+ = 311 ESI | 1, 5 |
| 13 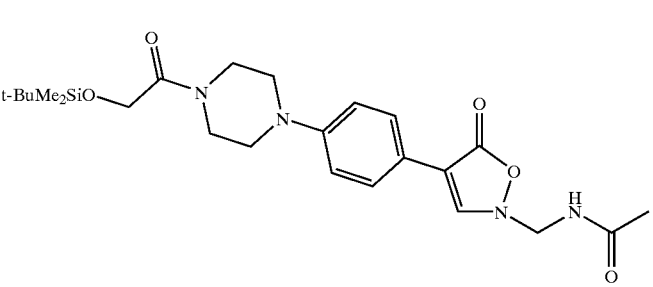 | (M + H)+ = 489 ESI | 2, 1, 6 |

-continued
| Structure | MS data | Prepared via Scheme(s) |
|---|---|---|
| 14 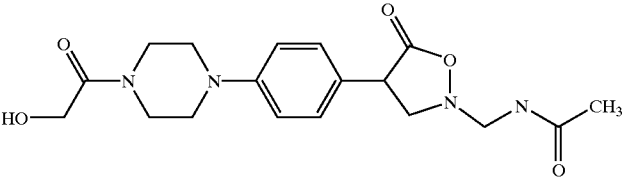 | (M + H)+ = 375 ESI | 2, 1, 6 |
| 15 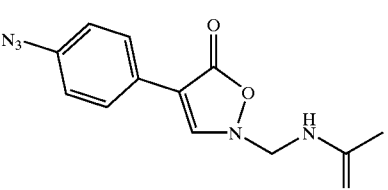 | (M + H)+ = 274 DCI | 1 |
| 16 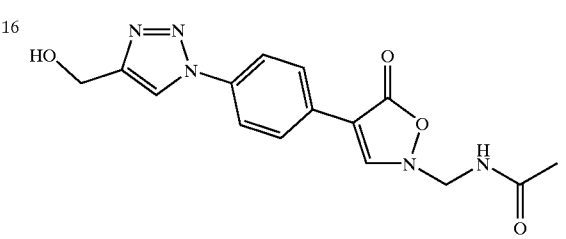 | (M + H)+ = 330 ESI | 1, 7 |
| 17 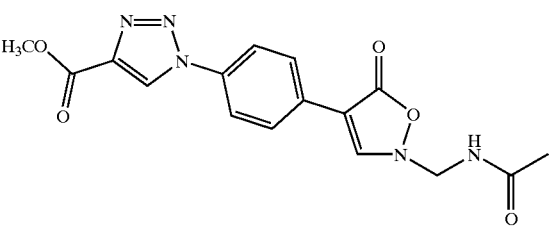 | (M + H)+ = 358 ESI | 1, 7 |
| 18 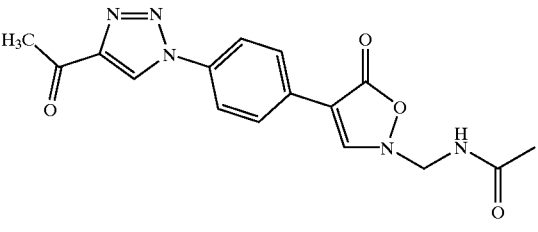 | (M + H)+ = 342 DCI | 1, 7 |
| 19 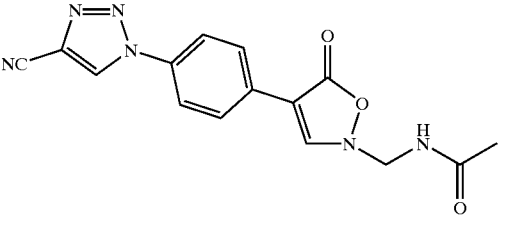 | (M + H)+ = 325 DCI | 1, 7 |
| 20 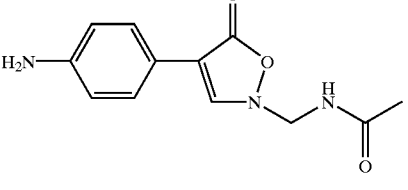 | (M + H)+ = 248 DCI | 1, 8 |

-continued
| | Structure | MS data | Prepared via Scheme(s) |
|---|---|---|---|
| 21 | 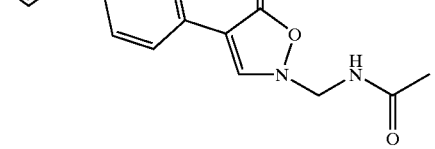 | (M + H)+ = 326 DCI | 1, 8 |
| 22 | 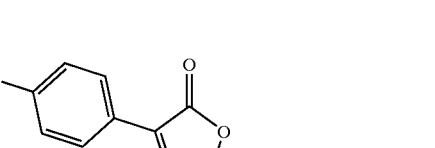 | (M + H)+ = 298 ESI | 1, 8 |
| 23 | 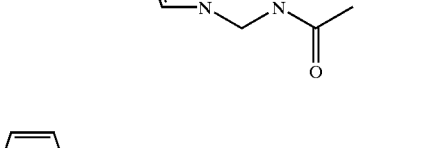 | (M + H)+ = 341 ESI | 1, 8 |
| 24 | 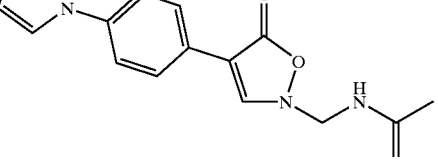 | (M + H)+ = 417 ESI | 2, 1, 6 |
| 25 |  | (M + H)+ = 317 ESI | 2, 1, 6 |
| 26 | 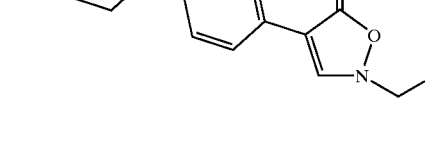 | (M + H)+ = 435 ESI | 3, 1, 6 |

-continued

| | Structure | MS data | Prepared via Scheme(s) |
|---|---|---|---|
| 27 | | (M + H)+ = 318<br>ESI | 2, 1 |
| 28 | | (M + H)+ = 334<br>ESI | 3, 1 |
| 29 | | (M + H)+ = 297<br>DCI | 3, 1 |
| 30 | | (M + H)+ = 281<br>ESI | 3, 1 |
| 31 | | (M + H)+ = 295<br>ESI | 3, 1 |
| 32 | | (M + H)+ = 323<br>ESI | 1, 8 |
| 33 | | (M + H)+ = 324<br>DCI | 1, 8 |

-continued

| Structure | MS data | Prepared via Scheme(s) |
|---|---|---|
| 34 [4-(methylthio)phenyl isoxazolone N-CH2-NH-CHO] | (M + H)+ = 265<br>DCI | 1 |
| 35 [4-(methylthio)phenyl isoxazolone N-CH2-NH-C(O)CH2Cl] | (M + H)+ = 313<br>DCI | 1 |
| 36 [4-(methylthio)phenyl isoxazolone N-CH2-NH-C(O)CH2F] | (M + H)+ = 297<br>DCI | 1 |
| 37 [4-chlorophenyl isoxazolone N-CH2-NH-C(O)CH2CH3] | (M + H)+ = 281<br>ESI | 1 |
| 38 [4-(methylthio)phenyl isoxazolone N-CH2-NH-C(O)CH2CH3] | (M + H)+ = 293<br>ESI | 1 |
| 39 [4-ethoxy-3-fluorophenyl isoxazolone N-CH2-NH-C(O)CH2CH3] | (M + H)+ = 309<br>ESI | 1 |
| 40 [4-methoxy-3-fluorophenyl isoxazolone N-CH2-NH-C(O)CH2CH3] | (M + H)+ = 295<br>ESI | 1 |

-continued
| Structure | MS data | Prepared via Scheme(s) |
|---|---|---|
| 41 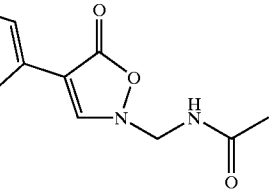 | (M + H)+ = 369 DCI | 1 |
| 42 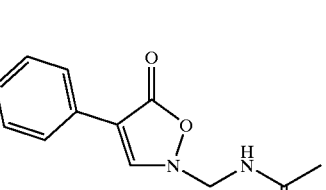 | (M + H)+ = 276 ESI | 1 |
| 43 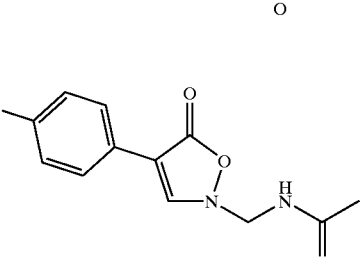 | (M + H)+ = 299 ESI | 1 |
| 44 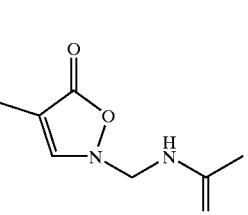 | (M + H)+ = 233 ESI | 1 |
| 45 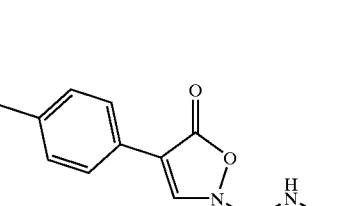 | (M + H)+ = 309 ESI | 1 |
| 46 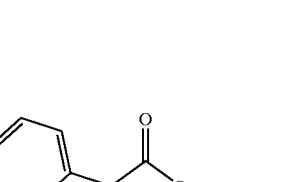 | (M + H)+ = 275 ESI | 1 |

-continued
| Structure | MS data | Prepared via Scheme(s) |
|---|---|---|
| 47 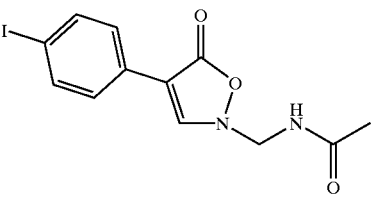 | (M + H)+ = 359 ESI | 1 |
| 48 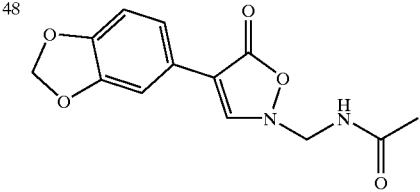 | (M + H)+ = 277 ESI | 1 |
| 49 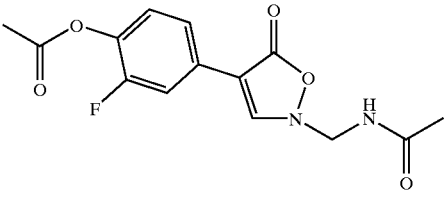 | (M + H)+ = 309 ESI | 1 |
| 50 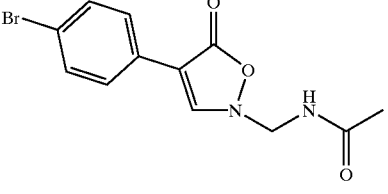 | (M + H)+ = 312 ESI | 1 |
| 51 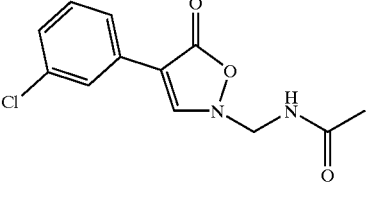 | (M + H)+ = 268 ESI | 1 |
| 52 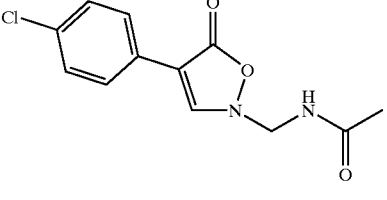 | (M + H)+ = 268 ESI | 1 |
| 53 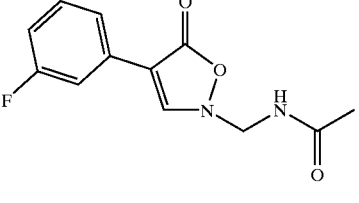 | (M + H)+ = 251 ESI | 1 |

-continued

| | Structure | MS data | Prepared via Scheme(s) |
|---|---|---|---|
| 54 | | (M + H)+ = 247 ESI | 1 |
| 55 | | (M + H)+ = 277 ESI | 1 |
| 56 | | (M + H)+ = 371 DCI | 1, 8 |
| 57 | | (M + H)+ = 395 ESI | 2, 1, 6 |
| 58 | | (M + H)+ = 359 ESI | 2, 1, 6 |
| 59 | | (M + H)+ = 399 ESI | 2, 1, 6 |
| 60 | | (M + H)+ = 455 ESI | 2, 1, 6 |

-continued
| | Structure | MS data | Prepared via Scheme(s) |
|---|---|---|---|
| 61 | 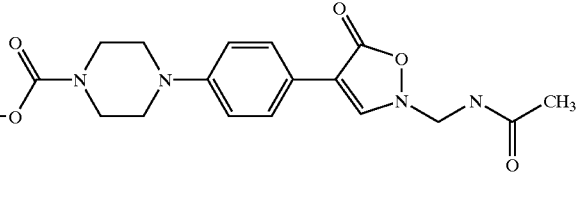 | (M + H)+ = 445<br>ESI | 2, 1, 6 |
| 62 | 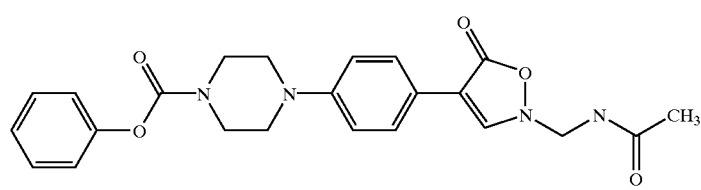 | (M + H)+ = 437<br>ESI | 2, 1, 6 |
| 63 | 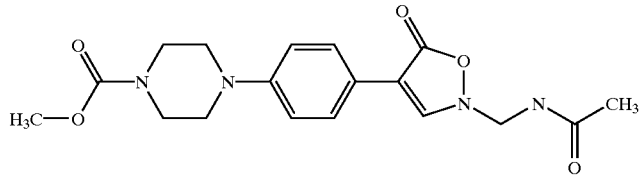 | (M + H)+ = 375<br>ESI | 2, 1, 6 |
| 64 | 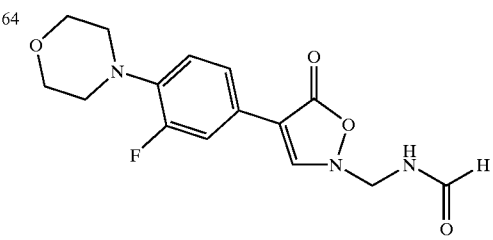 | (M + H)+ = 322<br>ESI | 3, 1 |
| 65 | 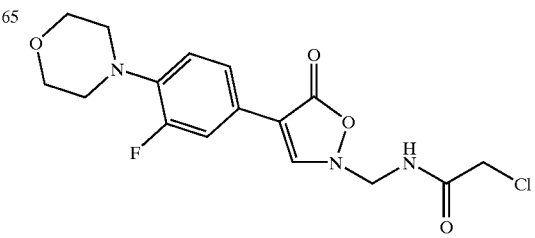 | (M + H)+ = 370<br>ESI | 3, 1 |
| 66 | 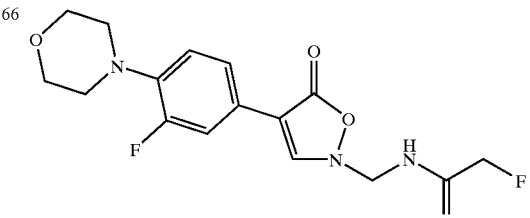 | (M + H)+ = 354<br>ESI | 3, 1 |

-continued

| | Structure | MS data | Prepared via Scheme(s) |
|---|---|---|---|
| 67 | | (M + H)+ = 350 ESI | 3, 1 |
| 68 | | (M + H)+ = 390 ESI | 3, 1 |
| 69 | | (M + H)+ = 354 ESI | 3, 1 |
| 70 | | (M + H)+ = 370 ESI | 3, 1 |
| 71 | | (M + H)+ = 302 ESI | 3, 1 |
| 72 | | (M + H)+ = 316 ESI | 3, 1 |

-continued
| | Structure | MS data | Prepared via Scheme(s) |
|---|---|---|---|
| 73 | 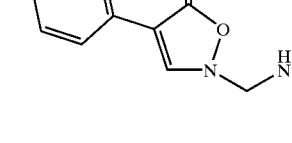 | (M + H)+ = 304<br>ESI | 3, 1 |
| 74 | 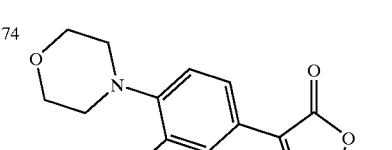 | (M + H)+ = 336<br>ESI | 3, 1 |
| 75 | 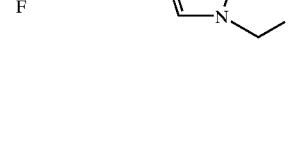 | (M + H)+ = 352<br>ESI | 3, 1 |
| 76 | 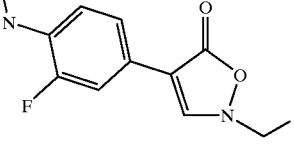 | (M + H)+ = 368<br>ESI | 3, 1, 4 |
| 77 | 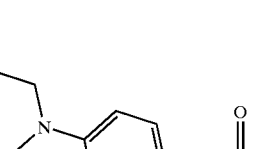 | (M + H)+ = 313<br>ESI | 3, 1, 4 |
| 78 | 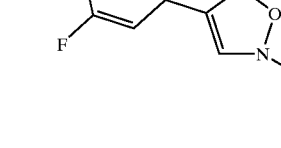 | (M + H)+ = 329<br>ESI | 3, 1, 4 |

-continued

| | Structure | MS data | Prepared via Scheme(s) |
|---|---|---|---|
| 79 | | (M + H)+ = 350 ESI | 3, 1, 4 |
| 80 | | (M + H)+ = 366 ESI | 3, 1, 4 |
| 81 | | (M + H)+ = 334 ESI | 3, 1, 6 |
| 82 | | (M + H)+ = 377 ESI | 3, 1, 6 |
| 83 | | (M + H)+ = 413 ESI | 3, 1, 6 |
| 84 | | (M + H)+ = 463 ESI | 3, 1, 6 |
| 85 | | (M + H)+ = 417 ESI | 3, 1, 6 |

-continued

| Structure | MS data | Prepared via Scheme(s) |
|---|---|---|
| 86 | (M + H)+ = 449 ESI | 3, 1, 6 |
| 87 | (M + H)+ = 469 ESI | 3, 1, 6 |
| 88 | (M + H)+ = 407 ESI | 3, 1, 6 |
| 89 | (M + H)+ = 393 ESI | 3, 1, 6 |
| 90 | (M + H)+ = 393 ESI | 3, 1, 6 |
| 91 | (M + H)+ = 429 ESI | 3, 1, 6 |
| 92 | (M + H)+ = 323 ESI | 1, 8 |

-continued

| Structure | MS data | Prepared via Scheme(s) |
|---|---|---|
| 93 (structure) | (M + H)+ = 355 ESI | 1, 8 |
| 94 (structure) | (M + H)+ = 382 ESI | 1, 8 |
| 95 (structure) | (M + H)+ = 371 DCI | 1, 9 |
| 96 (structure) | (M + H)+ = 324 DCI | 1, 9 |
| 97 (structure) | (M + H)+ = 299 ESI | 1, 9 |

We claim:
1. A compound of the formula

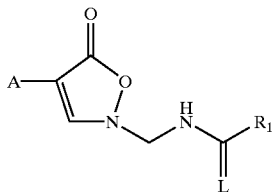

I or a pharmaceutically acceptable salt thereof wherein:
$R_1$ is
  a) H,
  b) $C_{1-8}$ alkyl or $C_{1-8}$ alkyl substituted with one or more F, Cl, OH, $C_{1-8}$ alkoxy, or $C_{1-8}$ acyloxy,
  c) $C_{3-6}$ cycloalkyl, or
  d) $C_{1-8}$ alkoxy;
L is oxygen or sulfur;
A is a)

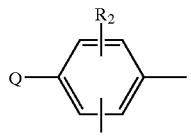

b)

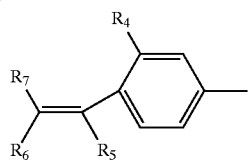

c) a 5-membered heteroaromatic moiety having one to three hetero atoms selected from the group consisting of S, N, and O, wherein the 5-membered heteroaromatic moiety is bonded via a carbon atom and is unsubstituted or substituted with one to three $R_8$,
  d) a 6-membered heteroaromatic moiety having at least one nitrogen atom, wherein the heteroaromatic moiety is bonded via a carbon atom and is unsubstituted or substituted with one to three $R_9$,
  e) a β-carbolin-3-yl, or indolizinyl bonded via the 6-membered ring, said β-carbolin-3-yl or indoliziny moiety being unsubstituted or substituted with one to three $R_9$, f)

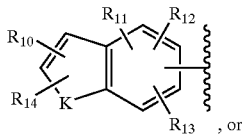, or g)

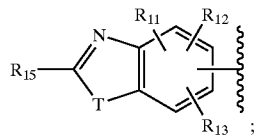;

wherein $R_2$ and $R_3$ are each independently
  a) H,
  b) F,
  c) Cl,
  d) Br,
  e) $C_{1-6}$ alkyl,
  f) $NO_2$,
  g) I,
  h) $C_{1-6}$ alkoxy,
  i) OH
  j) amino,
  k) cyano, or
  l) $R_2$ and $R_3$ taken together are $-O(CH_2)_h-O$;
wherein $R_4$ is
  a) H,
  b) $C_{1-2}$ alkyl,
  c) F, or
  d) OH;
$R_5$ is
  a) H,
  b) $CF_3$,
  c) $C_{1-3}$ alkyl or $C_{1-3}$ alkyl substituted with one or more halo,
  d) phenyl or phenyl substituted with one or more halo,
  e) $R_5$ and $R_6$ taken together are a 5-, 6-, or 7-membered ring of the formula,

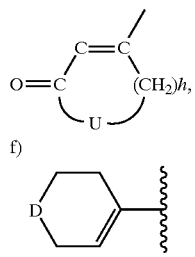

f)

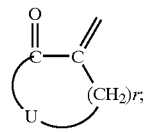

in which D is S, O or $NR_{86}$ in which $R_{86}$ is H or $C_{1-6}$ alkyl;
$R_6$ and $R_7$ at each occurrence are the same or different and are
  a) H,
  b) $CF_3$,
  c) $C_{1-3}$ alkyl or $C_{1-3}$ alkyl substituted with one halo, or
  d) $R_6$ and $R_7$ taken together are a 5-, 6-, or 7-membered ring of the formula, U is
  a) $CH_2$,
  b) O,
  c) S or,
  d) $NR_{16}$;
$R_{16}$ is
  a) H or
  b) $-C_{1-5}$ alkyl;
wherein $R_8$ is
  a) carboxyl,
  b) halo,
  c) $-CN$, d) mercapto,
e) formyl,
f) $CF_3$,
g) $NO_2$,
h) $C_{1-6}$ alkoxy,
i) $C_{1-6}$ alkoxycarbonyl,
j) $C_{1-6}$ alkythio,
k) $C_{1-6}$ acyl,
l) —$NR_{17}R_{18}$, m) 

in which $R_{87}$ is H or $C_{1-6}$ alkyl,
n) $C_{1-6}$ alkyl or $C_{1-6}$ alkyl substituted with OH, sulfamoyl, $C_{1-5}$ alkoxy, $C_{1-5}$ acyl, or —$NR_{17}R_{18}$,
o) $C_{2-8}$ alkyl or $C_{2-8}$ alkyl substituted with one or two $R_{19}$,
p) phenyl or phenyl substituted with one or two $R_{19}$,
q) a 5- or 6-membered saturated or unsaturated heterocyclic moiety having one to three atoms selected from the group consisting of S, N, and O, said heterocyclic moiety being unsubstituted or substituted with one or two $R_{19}$, or

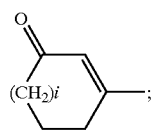

$R_{17}$ and $R_{18}$ at each occurrence are the same or different and are
a) H,
b) $C_{1-4}$ alkyl,
c) $C_{5-6}$ cycloalkyl, or
d) $R_{17}$ and $R_{18}$ taken together with the nitrogen atom is a 5- or 6-membered saturated or unsaturated heterocyclic moiety said heterocyclic moiety being unsubstituted or substituted with $C_{1-3}$ alkyl, formyl, a 5- or 6-membered heteroaromatic moiety containing 1–3 O, N or S,

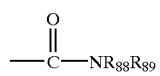

in which $R_{88}$ and $R_{89}$ are each independently hydrogen or $C_{1-6}$ alkyl, $SO_2R_{90}$ in which $R_{90}$ is H or $C_{1-6}$ alkyl, or unsubstituted $C_{1-3}$ acyl or $C_{1-3}$ acyl substituted with 1 or more F, Cl or OH;
$R_{19}$ is
a) carboxyl,
b) halo,
c) —CN,
d) mercapto,
e) formyl,
f) $CF_3$,
g) $NO_2$,
h) $C_{1-6}$ alkoxy,
i) $C_{1-6}$ alkoxycarbonyl,
j) $C_{1-6}$ alkythio,
k) $C_{1-6}$ acyl,
l) $C_{1-6}$ alkyl or $C_{1-6}$ alkyl substituted with OH, $C_{1-5}$ alkoxy, $C_{1-5}$ acyl, or —$NR_{17}R_{1-8}$,
m) phenyl,
n) —C(=O)$NR_{20}R_{21}$,
o) —N $R_{17}R_{18}$,
p) —N($R_{20}$)(—$SO_2R_{22}$),
q) —$SO_2$—$NR_{20}R_{21}$, or
r) —S(=O)$_tR_{22}$;
$R_{20}$ and $R_{21}$ at each occurrence are the same or different and are
a) H,
b) $C_{1-6}$ alkyl, or
c) phenyl;
$R_{22}$ is
a) $C_{1-4}$ alkyl, or
b) phenyl or phenyl substituted with $C_{1-4}$ alkyl;
wherein $R_9$ is
a) carboxyl,
b) halo,
c) —CN,
d) mercapto,
e) formyl,
f) $CF_3$,
g) $NO_2$,
h) $C_{1-6}$ alkoxy,
i) $C_{1-6}$ alkoxycarbonyl,
j) $C_{1-6}$ alkythio,
k) $C_{1-6}$ acyl,
l) —$NR_{23}R_{24}$,
m) $C_{1-6}$ alkyl or $C_{1-6}$ alkyl substituted with OH, $C_{1-5}$ alkoxy, $C_{1-5}$ acyl, or —$NR_{23}R_{24}$,
n) $C_{2-8}$ alkenylphenyl unsubstituted or substituted with one or two $R_{25}$,
o) phenyl or phenyl substituted with one or two $R_{25}$,
p) a 5- or 6-membered saturated or unsaturated heterocyclic moiety having one to three atoms selected from the group consisting of S, N, and O, said moiety being unsubstituted or substituted with one or two $R_{25}$, or q) 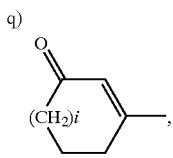

$R_{23}$ and $R_{24}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl, or
g) $R_{23}$ and $R_{24}$ taken together with the nitrogen atom is a 5- or 6-membered saturated heterocyclic moiety said heterocyclic moiety being unsubstituted or substituted with phenyl, pyrimidyl, $C_{1-3}$ alkyl, or $C_{1-3}$ acyl;
$R_{25}$ is
a) carboxyl,
b) halo,
c) —CN,
d) mercapto,
e) formyl,
f) $CF_3$,
g) $NO_2$,
h) $C_{1-6}$ alkoxy, i) $C_{1-6}$ alkoxycarbonyl,
j) $C_{1-6}$ alkythio,
k) $C_{1-6}$ acyl,
l) phenyl,
m) $C_{1-6}$ alkyl or $C_{1-6}$ alkyl substituted with OH, azido, $C_{1-5}$ alkoxy, $C_{1-5}$ acyl, —$NR_{32}R_{33}$, —$SR_{34}$, —O—$SO_2R_{35}$, or $R_{36}$—⟨phenyl⟩—NH—CO—O—, n) —C(=O)$NR_{26}R_{27}$,
o) —$NR_{23}R_{24}$,
p) —$N(R_{26})(—SO_2R_{22})$,
q) —$SO_2$—$NR_{26}R_{27}$, or
r) —$S(=O)_iR_{22}$,
s) —CH=N—$R_{28}$, or
t) —CH(OH)—$SO_3R_{31}$;

$R_{22}$ is the same as defined above;

$R_{26}$ and $R_{27}$ at each occurrence are the same or different and are
a) H,
b) $C_{1-6}$ alkyl,
c) phenyl, or
d) tolyl;

$R_{28}$ is
a) OH,
b) benzyloxy,
c) —NH—C(=O)—$NH_2$,
d) —NH—C(=S)—$NH_2$, or
e) —NH—C(=NH)—$NR_{29}R_{30}$;

$R_{29}$ and $R_{30}$ at each occurrence are the same or different and are
a) H, or
b) $C_{1-4}$ alkyl or $C_{1-4}$ alkyl substituted with phenyl or pyridyl;

$R_{31}$ is
a) H, or
b) a sodium ion;

$R_{32}$ and $R_{33}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl,
g) $R_{32}$ and $R_{33}$ taken together are a 5- or 6-membered saturated heterocyclic moiety having one to three atoms selected from the group consisting of S, N, O, said heterocyclic moiety being unsubstituted or substituted on a carbon or nitrogen atom with phenyl, pyrimidyl, $C_{1-3}$ alkyl, or $C_{1-3}$ acyl,
h) —P(O)($OR_{37}$)($OR_{38}$), or
i) —$SO_2$—$R_{39}$;

$R_{34}$ is

[tetrazole with N—CH3], [(CH3)3C—thiadiazole—], or

[benzimidazole with N-CH3], or [imidazole with N-CH3];

$R_{35}$ is $C_{1-3}$ alkyl;

$R_{36}$ is
a) $C_{1-6}$ alkoxycarbonyl, or
b) carboxyl;

$R_{37}$ and $R_{38}$ at each occurrence are the same or different and are
a) H, or
b) $C_{1-3}$ alkyl;

$R_{39}$ is
a) methyl,
b) phenyl, or
c) tolyl;

wherein K is
a) O,
b) S, or
c) $NR_{40}$ in which $R_{40}$ is hydrogen, formyl, $C_{1-4}$ alkyl, $C_{1-4}$ acyl, phenyl, $C_{3-6}$ cycloalkyl, —P(O)($OR_{37}$)($OR_{38}$) or —$SO_2$—$R_{39}$ in which $R_{37}$, $R_{38}$ and $R_{39}$ are as defined above;

$R_{10}$, $R_{11}$, $R_{12}$, $R_{13}$, $R_{14}$ and $R_{15}$ at each occurrence are the same or different and are
a) H,
b) formyl,
c) carboxyl,
d) $C_{1-6}$ alkoxycarbonyl,
e) $C_{1-8}$ alkyl,
f) $C_{2-8}$ alkenyl,
wherein the substituents (e) and (f) are unsubstituted or substituted with OH, halo, $C_{1-6}$ alkoxyl, $C_{1-6}$ acyl, $C_{1-6}$ alkylthio or $C_{1-6}$ alkoxycarbonyl, or phenyl or phenyl substituted with halo,
g) phenyl or naphthyl being unsubstituted or substituted with carboxyl, halo, —CN, formyl, $CF_3$, $NO_2$, $C_{1-6}$ alkyl, $C_{1-6}$ alkoxy, $C_{1-6}$ acyl, $C_{1-6}$ alkylthio, or $C_{1-6}$ alkoxycarbonyl;
h) —$NR_{42}R_{43}$,
i) $OR_{44}$,
j) —$S(=O)_i$—$R_{45}$,
k) —$SO_2$—$N(R_{46})(R_{47})$, or
l) a radical having the formula:

[morpholine-N—], [piperidine-N— with CONH2],

[dioxolane-spiro-piperidine N—], $R_{48}R_{49}N$—[pyridinium N+—],

[cyclohexyl with $R_{50}$, $R_{51}$]—, HN[piperazine]N—;

-continued

R52—(CH2)t—N☐N—, or  R53—N☐N—;
         (R53)              (R53)
         |j                 |u $R_{19}$ is the same as defined above;

T is
 a) O,
 b) S, or
 c) $SO_2$;

$R_{42}$ and $R_{43}$ at each occurrence are the same or different and are
 a) H,
 b) $C_{3-6}$ cycloalkyl,
 c) phenyl,
 d) $C_{1-6}$ acyl,
 e) $C_{1-8}$ alkyl or $C_{1-8}$ alkyl substituted with OH, $C_{1-6}$ alkoxy which is unsubstituted or substituted with OH, a 5- or 6-membered aromatic heterocyclic moiety having one to three atoms selected from the group consisting of S, N, and O, phenyl or phenyl substituted with OH, $CF_3$, halo, —$NO_2$, $C_{1-4}$ alkoxy, —NR48R49, or

[benzodioxole structure]

f)
    O
    ‖
    C—$R_{54}$
    |
$R_{55}$—CH—  , or g)
    V☐N—(CH_2)t—;

V is
 a) O,
 b) $CH_2$, or
 c) $NR_{56}$;

$R_{48}$ and $R_{49}$ at each occurrence are the same or different and are
 a) H, or
 b) $C_{1-4}$ alkyl;

$R_{54}$ is
 a) OH,
 b) $C_{1-4}$ alkoxy, or
 c) —$NR_{57}R_{58}$;

$R_{55}$ is
 a) H, or
 b) $C_{1-7}$ alkyl or $C_{1-7}$ alkyl substituted with indolyl, OH, mercaptyl, imidazolyl, methylthio, amino, phenyl optionally substituted with OH, —C(=O)—$NH_2$, —$CO_2H$, or —C(=NH)—$NH_2$;

$R_{56}$ is
 a) H,
 b) phenyl, or
 c) $C_{1-6}$ alkyl or $C_{1-6}$ alkyl substituted by OH;

$R_{57}$ and $R_{58}$ at each occurrence are the same or different and are
 a) H,
 b) $C_{1-5}$ alkyl,
 c) $C_{1-3}$ cycloalkyl, or
 d) phenyl;

$R_{44}$ is
 a) $C_{1-8}$ alkyl or $C_{1-8}$ alkyl substituted with $C_{1-6}$ alkoxy or $C_{1-6}$ hydroxy, $C_{3-6}$ cycloalkyl, a 6-membered aromatic moiety or a 6-membered aromatic benzo-fused heterocyclic moiety having one to three nitrogen atoms, said aromatic moiety being unsubstituted or substituted with one or two —$NO_2$, $CF_3$, halo, —CN, OH, $C_{1-5}$ alkyl, $C_{1-5}$ alkoxy, or $C_{1-5}$ acyl, b)
    V☐N—(CH_2)t—, c) phenyl, or
 d) pyridyl;

$R_{45}$ is
 a) $C_{1-16}$ alkyl,
 b) $C_{2-16}$ alkenyl,
  wherein the substituents (a) and (b) are unsubstituted or substituted with $C_{1-6}$ alkoxycarbonyl, or a 5-, 6-, or 7-membered aromatic heterocyclic moiety having one to three atoms selected from the group consisting of S, N, and O,
 c) phenyl or naphthyl, or
 d) a 5-, 6-, or 7-membered aromatic heterocyclic moiety having one to three atoms selected from the group of S, N, and O, wherein the substituents (c) and (d) are unsubstituted or substituted with carboxyl, halo, —CN, formyl, $CF_3$, —$NO_2$, $C_{1-6}$ alkyl, $C_{1-6}$ alkoxy, $C_{1-6}$ acyl, $C_{1-6}$ alkylthio, or $C_{1-6}$ alkoxycarbonyl;

$R_{46}$ and $R_{47}$ at each occurrence are the same or different and are
 a) H,
 b) phenyl,
 c) $C_{1-6}$ alkyl, or
 d) benzyl;

$R_{50}$ and $R_{51}$ at each occurrence are the same or different and are
 a) H,
 b) OH,
 c) $C_{1-6}$ alkyl or $C_{1-6}$ alkyl substituted with —NR48R49 in which $R_{48}$ and $R_{49}$ are as defined above,
 d) $R_{50}$ and $R_{51}$ taken together are =O;

$R_{52}$ is
 a) phenyl or naphthyl,
 b) a 5- or 6-membered aromatic heterocyclic moiety or 5- or 6-membered benzo-fused heterocyclic moiety having one to three atoms selected from the group consisting of S, N, and O, wherein the substituents (a) and (b) are be unsubstituted or substituted with one or three —$NO_2$, $CF_3$, halo, —CN, OH, phenyl, $C_{1-5}$ alkyl, $C_{1-5}$ alkoxy, or $C_{1-5}$ acyl,
 c) morpholinyl,
 d) OH,
 e) $C_{1-6}$ alkoxy,
 f) —NR48R49 in which $R_{48}$ and $R_{49}$ are as defined above, g) —C(=O)—R$_{59}$, or h) 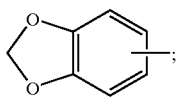;

R$_{53}$ is
  a) H,
  b) formyl,
  c) C$_{1-4}$ alkyl,
  d) C$_{1-4}$ acyl,
  e) phenyl,
  f) C$_{3-6}$ cycloalkyl,
  g) —P(O)(OR$_{37}$)(OR$_{38}$), or
  h) —SO$_2$R$_{39}$, in which R$_{37}$, R$_{38}$ and R$_{39}$ are as defined above;

R$_{59}$ is
  a) morpholinyl,
  b) OH, or
  c) C$_{1-6}$ alkoxy;

h is 1, 2, or 3;
i is 0, 1, or 2;
j is 0, or 1;
r is 1, 2, 3, 4, 5 or 6;
t is 0, 1, 2, 3, 4, 5, or 6;
u is 1 or 2; and Q is
  a) hydrogen,
  b) halo,
  c) NO$_2$,
  d) N$_3$,
  e) C$_1$–C$_6$ alkylthio, f) 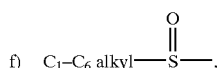, g) 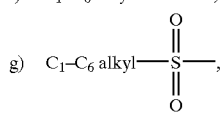, h) C$_1$–C$_6$ alkyl,
  i) C$_1$–C$_6$ alkoxy,
  j) formyl, k) 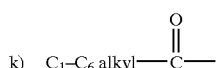, l) 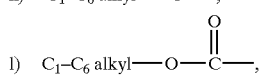, m) -sulfamoyl (H$_2$NSO$_2$—),
  n) —NHOH, o) 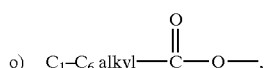, p) 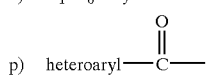

in which heteroaryl is a 5- or 6-membered aromatic heterocyclic group having 1–3 hetero atoms selected from O, N or S, q) 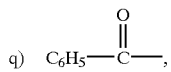, r) amino,
  s) C$_1$–C$_6$ alkylamino,
  t) di(C$_1$–C$_6$ alkyl)amino-, u) 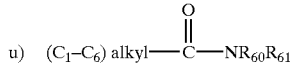

in which R$_{60}$ and R$_{61}$ are each independently hydrogen or C$_1$–C$_6$ alkyl,
  v) OH,
  w) cyano,
  x) hydroxy (C$_1$–C$_6$ alkyl), y) 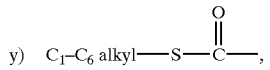, z) 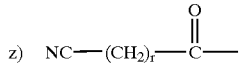

in which r is 1–6, aa) 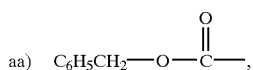, bb) 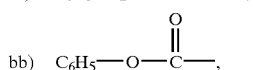, cc) 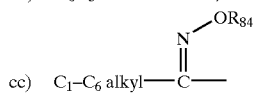

in which R$_{84}$ is hydrogen or C$_{1-6}$ alkyl, dd) 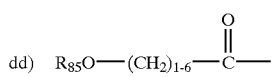

in which R$_{85}$ is hydrogen, C$_{1-8}$ alkyl or C$_{1-8}$ alkyl substituted with one or more F, Cl, OH, C$_{1-8}$ alkoxy or C$_{1-8}$ acyloxy, C$_{3-6}$ cycloalkyl or C$_{1-8}$ alkoxy;

ee) 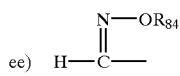

in which R$_{84}$ is hydrogen or C$_{1-6}$ alkyl,
  ff) a substituted or unsubstituted C$_6$–C$_{10}$ aryl moiety,
  gg) a substituted or unsubstituted monocyclic or bicyclic, saturated or unsaturated, heterocyclic moiety having 1–3 atoms selected from O, N or S, said ring being bonded via a ring carbon or nitrogen to the phenyl substituent,
  hh) a monocyclic or bicyclic substituted or unsubstituted heteroaromatic moiety having 1–3 hetero atoms selected from O, N or S, said ring being bonded via a ring carbon or nitrogen to the phenyl substituent;
  the substituents for such p, q, ff, gg and hh moieties being selected from 1 or 2 of the following:
    1) halo,
    2) C$_{1-6}$ alkyl,

3) $NO_2$,
4) $N_3$,

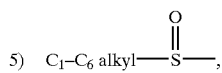
5) $C_1$–$C_6$ alkyl—S(=O)—,

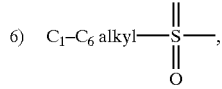
6) $C_1$–$C_6$ alkyl—S(=O)(=O)—, 7) formyl,

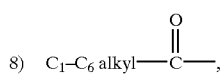
8) $C_1$–$C_6$ alkyl—C(=O)—,

9) $C_1$–$C_6$ alkyl—O—C(=O)—,

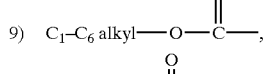
10) heteroaryl—C(=O)— in which heteroaryl is a 5- or 6-membered aromatic heterocyclic group having 1–3 hetero atoms selected from O, N or S,

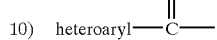
11) $C_6H_5$—C(=O)—,

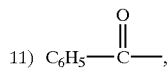
12) —($C_1$–$C_6$) alkyl—C(=O)—$NR_{60}R_{61}$ in which $R_{60}$ and $R_{61}$ are each independently hydrogen or $C_1$–$C_6$ alkyl,
13) OH,
14) hydroxy ($C_1$–$C_6$ alkyl),

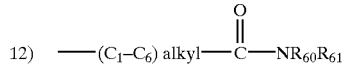
15) $C_1$–$C_6$ alkyl—S—C(=O)—,

16) NC—$(CH_2)_r$—O—C(=O)— in which r is 1–6,

17) $C_6H_5CH_2$—O—C(=O)—,

18) —$CH_2$—$R_{80}$ in which $R_{80}$ is
  a) —$OR_{32}$ in which $R_{32}$ is as defined above,
  b) —$SR_{32}$ in which $R_{32}$ is as defined above,
  c) —$NR_{32}R_{33}$ in which $R_{32}$ and $R_{33}$ are as defined above, or
  d) 5- or 6-membered heteroaromatic containing 1–4 O, S or N atoms,

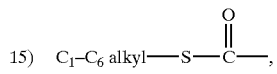
19) $C_1$–$C_6$ alkyl—C(=N—$OR_{84}$)— in which $R_{84}$ is as defined above,
20) cyano,
21) carboxyl,

22) $CF_3$,

23) $C_1$–$C_6$ alkyl—C(=O)—O—,

24) $C_6H_5$—O—C(=O)— in which the phenyl moiety may be unsubstituted or substituted by halo or ($C_1$–$C_6$)alkyl,

25) $NR_{60}R_{61}$—C(=O)— in which $R_{60}$ and $R_{61}$ are as defined above,

26) $R_{91}$—NH—C(=O)— or $R_{91}$—C(=O)—NH— in which $R_{91}$ is a 5- or 6-membered aromatic heterocyclic group having 1–3 O, N or S,

27) $C_6H_5(CH_2)_{1-6}$—O—C(=O)—,

28) $R_{85}$O—$(CH_2)_{1-6}$—O—C(=O)— in which $R_{85}$ is as defined above,

29) $SiR_{99}R_{100}R_{101}$—O—$CH_2$—C(=O)— in which $R_{99}$, $R_{100}$ and $R_{101}$ are each independently $C_{1-6}$ alkyl; or
Q and either $R_1$ and $R_2$ taken together form —O—$CH_2$—O.

2. A compound of claim 1 wherein A is

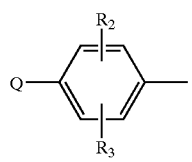

in which Q, $R_2$ and $R_3$ are as defined in claim 1.

3. A compound of the formula

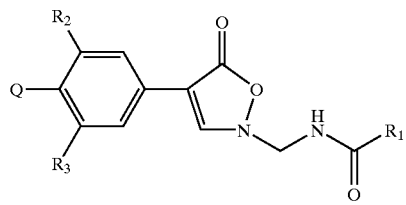

or a pharmaceutically acceptable salt thereof, in which
  $R_1$ is H, $C_{1-8}$ alkyl unsubstituted or substituted with one or more F, Cl, OH, $C_{1-8}$ alkoxy, or $C_{1-8}$ acyloxy, $C_{3-6}$ cycloalkyl or $C_{1-8}$ alkoxy;

$R_2$ and $R_3$ are each independently
a) H,
b) F,
c) Cl,
d) Br,
e) $C_{1-6}$ alkyl,
f) $NO_2$,
g) I,
h) $C_{1-6}$ alkoxy,
i) OH
j) amino, or
k) cyano; and Q is
a) hydrogen,
b) halo,
c) $NO_2$,
d) $N_3$,
e) $C_1$–$C_6$ alkylthio, f) 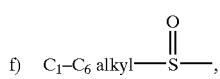

g) 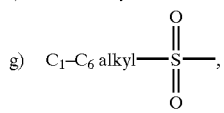

h) $C_1$–$C_6$ alkyl,
i) $C_1$–$C_6$ alkoxy,
j) formyl, k) 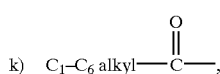

l) 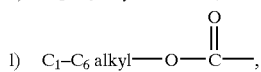

m) 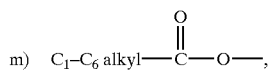

n) 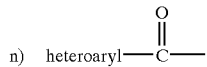

in which heteroaryl is a 5- or 6-membered aromatic heterocyclic group having 1–3 hetero atoms selected from O, N or S, s) 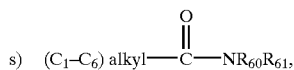

p) amino,
q) $C_1$–$C_6$ alkylamino-,
r) di($C_1$–$C_6$ alkyl)amino-,

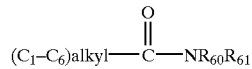

in which $R_{60}$ and $R_{61}$ are each independently hydrogen or $C_1$–$C_6$ alkyl,
t) OH,
u) cyano,
v) hydroxy ($C_1$–$C_6$ alkyl), w) 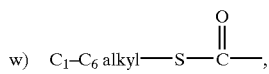

x) 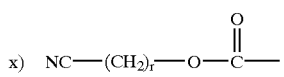

in which r is 1–6, y) 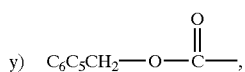

z) 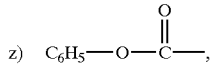

aa) 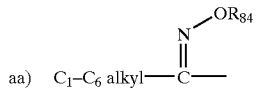

wherein $R_{84}$ is hydrogen or $C_{1-6}$ alkyl, bb) 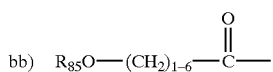

in which $R_{85}$ is hydrogen, $C_{1-8}$ alkyl or $C_{1-8}$ alkyl substituted with one or more F, Cl, OH, $C_{1-8}$ alkoxy or $C_{1-8}$ acyloxy, $C_{3-6}$ cycloalkyl or $C_{1-8}$ alkoxy, cc) 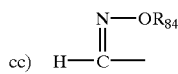

in which $R_{84}$ is as defined above, dd) ee) ff)
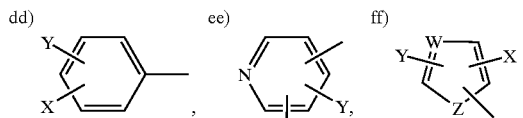

gg) hh) ii)
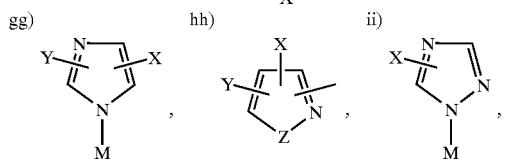

jj) kk)
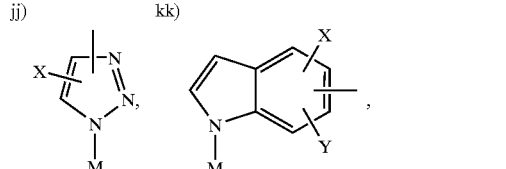

ll) mm)
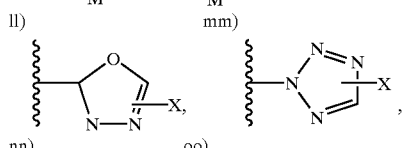

nn) oo)
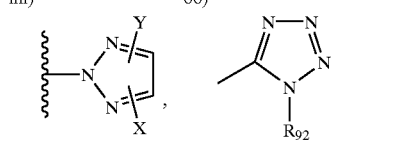

in which $R_{92}$ is H or $C_{1-6}$ alkyl,

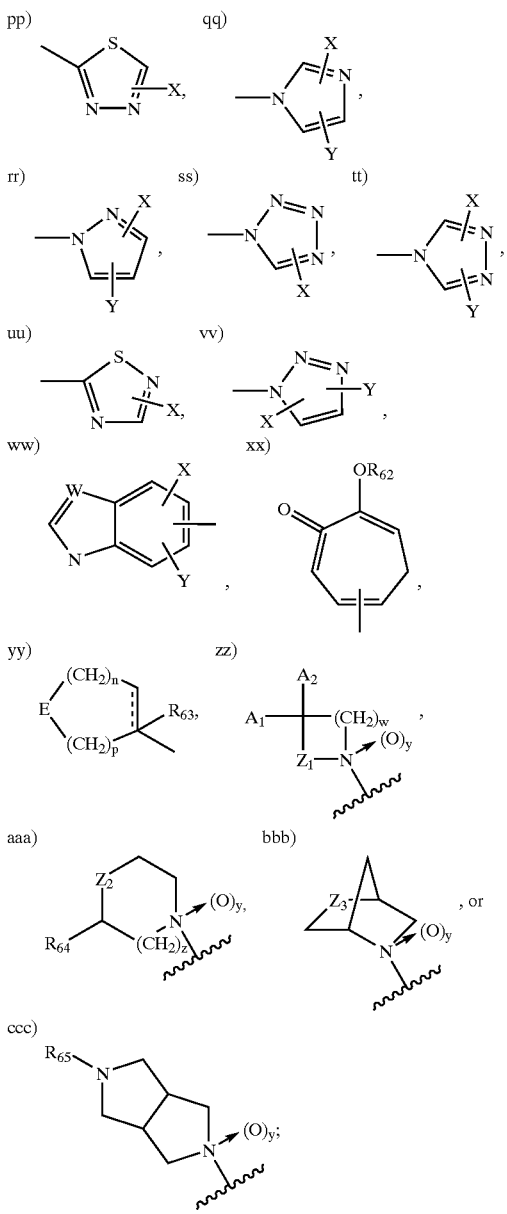

M is
 a) H,
 b) $C_{1-8}$ alkyl,
 c) $C_{3-8}$ cycloalkyl,
 d) —$(CH_2)_m OR_{66}$, or
 e) —$(CH_2)_n NR_{67}R_{68}$;
Z is
 a) O,
 b) S or
 c) NM;
W is
 a) CH,
 b) N or
 c) S or O when Z is NM;
X and Y are each independently
 a) hydrogen,
 b) halo,
 c) $NO_2$,
 d) $N_3$,
 e) $C_{1-6}$ alkythio, f) $C_1$–$C_6$ alkyl—S(=O)—, g) $C_1$–$C_6$ alkyl—S(=O)$_2$—, h) $C_1$–$C_6$ alkyl,
 i) $C_1$–$C_6$ alkoxy,
 j) formyl, k) $C_1$–$C_6$alkyl—C(=O)—, l) $C_1$–$C_6$alkyl—O—C(=O)—, m) heteroaryl—C(=O)— in which heteroaryl is a 5- or 6-membered aromatic heterocyclic group having 1–3 hetero atoms selected from O, N or S, n) $C_6H_5$—C(=O)—, o) amino,
 p) $C_1$–$C_6$ alkylamino-,
 q) di($C_1$–$C_6$ alkyl)amino-, r) —$(C_1$–$C_6)$alkyl—C(=O)—$NR_{60}R_{61}$ in which $R_{60}$ and $R_{61}$ are each independently hydrogen or $C_1$–$C_6$ alkyl,
 s) OH,
 t) hydroxy ($C_1$–$C_6$ alkyl), u) $C_1$–$C_6$alkyl—S—C(=O)—, v) NC—$(CH_2)_r$—O—C(=O)— in which r is 1–6, w) $C_6H_5CH_2$—O—C(=O)—, x) $C_6H_5$—O—C(=O)—, y) $C_1$–$C_6$alkyl—C(=NOR$_{84}$)— in which $R_{84}$ is as defined above,
 z) cyano,
 aa) carboxyl, bb) CF$_3$,
cc) mercapto,

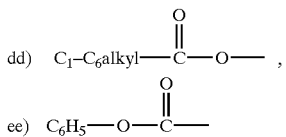

dd) C$_1$–C$_6$alkyl—C(=O)—O—, ee) C$_6$H$_5$—O—C(=O)— in which the phenyl moiety is unsubstituted or substituted by halo or C$_1$–C$_6$ alkyl,

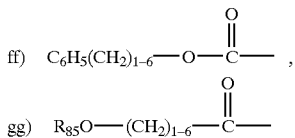

ff) C$_6$H$_5$(CH$_2$)$_{1-6}$—O—C(=O)—, gg) R$_{85}$O—(CH$_2$)$_{1-6}$—C(=O)— in which R$_{85}$ is as defined above, or

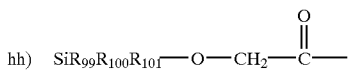

hh) SiR$_{99}$R$_{100}$R$_{101}$—O—CH$_2$—C(=O)— in which R$_{99}$, R$_{100}$ and R$_{101}$ are each independently C$_{1-6}$ alkyl; or Q and either R$_1$ and R$_3$ taken together form —O—CH$_2$—O;

R$_{62}$ is
 a) H,
 b) C$_{1-8}$ alkyl or C$_{1-8}$ alkyl substituted with one or more halos, or
 c) C$_{1-8}$ alkyl or C$_{1-8}$ alkyl substituted with one or more OH, or C$_{1-8}$ alkoxy;

E is
 a) NR$_{69}$,
 b) —S(=O)$_i$— in which i is 0, 1 or 2, or
 c) O;

R$_{63}$ is
 a) H,
 b) C$_{1-6}$ alkyl,
 c) —(CH$_2$)$_q$-aryl, or
 d) halo;

R$_{66}$ is H or C$_{1-4}$ alkyl;

R$_{67}$ and R$_{68}$ are each independently H or C$_{1-4}$ alkyl, or NR$_{67}$R$_{68}$ taken together are —(CH$_2$)$_m$—;

R$_{69}$ is
 a) H,
 b) C$_{1-6}$ alkyl,
 c) —(CH$_2$)$_q$-aryl,
 d) —CO$_2$R$_{81}$,
 e) COR$_{82}$,
 f) —C(=O)—(CH$_2$)$_q$—C(=O)R$_{81}$,
 g) —S(=O)$_z$—C$_{1-6}$ alkyl,
 h) —S(=O)$_z$—(CH$_2$)$_q$-aryl, or
 i) —(C=O)$_j$-Het in which j is 0 or 1 and Het represents a 5 to 10 membered saturated, unsaturated or aromatic heterocyclic ring containing at least one O, S or N;

Z$_1$ is
 a) —CH$_2$—, or
 b) —CH(R$_{70}$)—CH$_2$—;

Z$_2$ is
 a) —O$_2$S—,
 b) —O—,
 c) —S—,
 d) —SO—, or
 e) —N(R$_{71}$)—;

Z$_3$ is
 a) S,
 b) SO,
 c) SO$_2$, or
 d) O;

A$_1$ is H or CH$_3$;

A$_2$ is
 a) H,
 b) OH—,
 c) CH$_3$CO$_2$—,
 d) CH$_3$—,
 e) CH$_3$O—,
 f) R$_{72}$O—CH$_2$—C(O)—NH—,
 g) R$_{73}$O—C(O)—NH—,
 h) R$_{73}$—C(O)—NH—,
 i) (C$_1$–C$_2$)alkyl-O—C(O)—, or
 j) HO—CH$_2$; or A$_1$ and A$_2$ taken together are a)

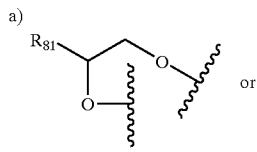

or b) O=;

R$_{64}$ is H or CH$_3$—;

m is 4 or 5;

n is 0, 1, 2, 3, 4 or 5;

y is 0 or 1;

p is 0, 1, 2, 3, 4 or 5;

w is 1, 2 or 3;

q is 1, 2, 3 or 4;

z is 0 or 1;

R$_{65}$ is
 a) R$_{74}$OC(R$_{75}$)(R$_{76}$)—C(O)—,
 b) R$_{77}$OC(O)—,
 c) R$_{78}$(O)—,
 d) R$_{79}$—SO$_2$—, or
 e) R$_{80}$—NH—C(O)—;

R$_{70}$ is H or (C$_1$–C$_3$)alkyl;

R$_{71}$ is
 a) R$_{74}$OC(R$_{75}$)(R$_{76}$)—C(O)—,
 b) R$_{77}$O—C(O)—,
 c) R$_{78}$—C(O)—, d) 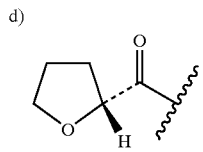 e) 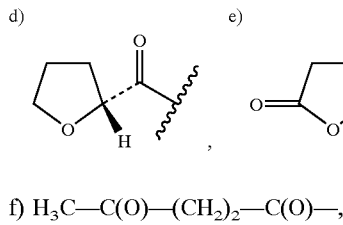

f) H$_3$C—C(O)—(CH$_2$)$_2$—C(O)—, g) $R_{79}$—$SO_2$—, h) 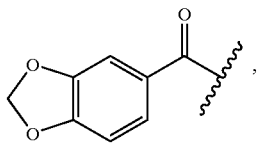

i) $R_{80}$—NH—C(O)—, $R_{72}$ is
  a) H,
  b) $CH_3$,
  c) phenyl —$CH_2$—, or
  d) $CH_3C(O)$—;

$R_{73}$ is ($C_1$–$C_3$)alkyl or phenyl;

$R_{74}$ is H, $CH_3$, phenyl-$CH_2$— or $CH_3$—C(O)—;

$R_{75}$ and $R_{76}$ are each independently H or $CH_3$, or $R_{75}$ and $R_{76}$ taken together are —$CH_2CH_2$—;

$R_{77}$ is ($C_1$–$C_3$)alkyl or phenyl;

$R_{78}$ is H, ($C_1$–$C_4$)alkyl, aryl-($CH_2$)$_{n^1}$, $ClH_2C$, $Cl_2HC$, $FH_2C$—, $F_2HC$— or ($C_3$–$C_6$)cycloalkyl;

$R_{79}$ is $CH_3$; —$CH_2Cl$, —$CH_2CH$=$CH_2$, aryl or —$CH_2CN$;

$R_{80}$ is —($CH_2$)$_{n^1}$-aryl where $n^1$ is 0 or 1;

$R_{81}$ is
  a) H,
  b) $C_{1-6}$ alkyl or $C_{1-6}$ alkyl substituted with one or more OH, halo or CN,
  c) —($CH_2$)$_q$-aryl in which q is as defined above, or
  d) —($CH_2$)$_q$—$OR_{83}$ in which q is as defined above;

$R_{82}$ is
  a) $C_{1-6}$ alkyl or $C_{1-6}$ alkyl substituted with one or more OH, halo or CN,
  b) —($CH_2$)$_q$-aryl in which q is as defined above, or
  c) —($CH_2$)$_q$—$OR_{83}$ in which q is as defined above;

$R_{83}$ is
  a) H,
  b) $C_{1-6}$ alkyl,
  c) —($CH_2$)$_q$-aryl in which q is as defined above; or
  d) —C(=O) $C_{1-6}$ alkyl; and aryl is phenyl, pyridyl or naphthyl, said phenyl, pyridyl or naphthyl moieties being unsubstituted or substituted by one or more halo, —CN, OH, SH, $C_{1-6}$ alkoxy or $C_{1-6}$ alkylthio.

4. A compound of the formula

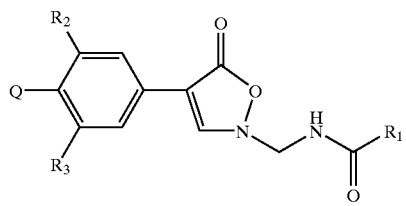

IA or a pharmaceutically acceptable salt thereof, in which $R_1$ is H, $C_{1-8}$ alkyl unsubstituted or substituted with one or more F, Cl, OH, $C_{1-8}$ alkoxy or $C_{1-8}$ acyloxy, $C_{3-6}$ cycloalkyl or $C_{1-8}$ alkoxy;

$R_2$ and $R_3$ are each independently H or F; or $R_2$ and $R_3$ taken together represent

Q is
  a) hydrogen,
  b) halo,
  c) $N_3$,
  d) $NO_2$,
  e) $C_1$–$C_6$ alkylthio, f) 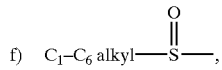

g) 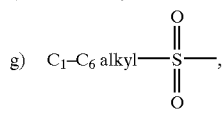

h) $C_1$–$C_6$ alkyl,
i) $C_1$–$C_6$ alkoxy,
j) formyl, k) 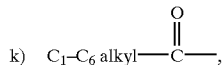

l) 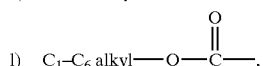

m) 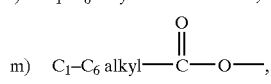

n) ($C_1$–$C_6$ alkoxy)$_2$N—, o) 5- or 6-membered saturated or unsaturated heterocyclic containing 1–3 O, N or S and linked to the phenyl substituent via a carbon or nitrogen, said heterocycle moiety being unsubstituted or substituted by $R_{96}$, p) 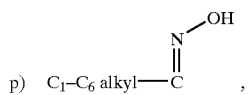

q) phenyl or phenyl substituted by $R_{96}$, and $R_{96}$ is
  a) $C_1$–$C_6$ alkyl-OH, b) 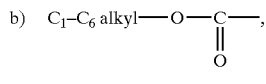

c) 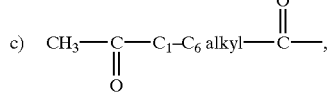

d) cyano,
e) formyl, f) 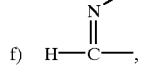

-continued g) 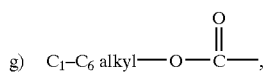

h) 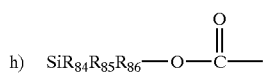

in which $R_{84}$, $R_{85}$ and $R_{86}$ are each independently $C_1$–$C_6$ alkyl, i) 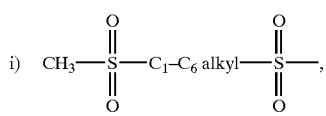

j) 

k) 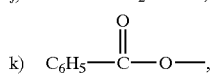

where the phenyl is unsubstituted or substituted by halo, l) 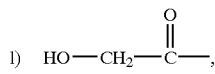

m) $(C_1$–$C_6$ alkyl$)_2$N—,
n) $C_1$–$C_6$ alkyl-NH—,
o) amino, p) 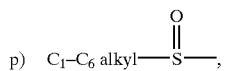

q) , or r) 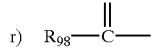

in which $R_{98}$ is phenyl, 5- or 6-membered heteroaryl containing 1–3 O, N or S and linked to the phenyl substituent via a ring carbon atom or 5- or 6-membered saturated or unsaturated heterocyclic containing 1–4 O, N or S and linked to the phenyl substituent via a ring carbon atom.

5. A compound selected from the group consisting of:

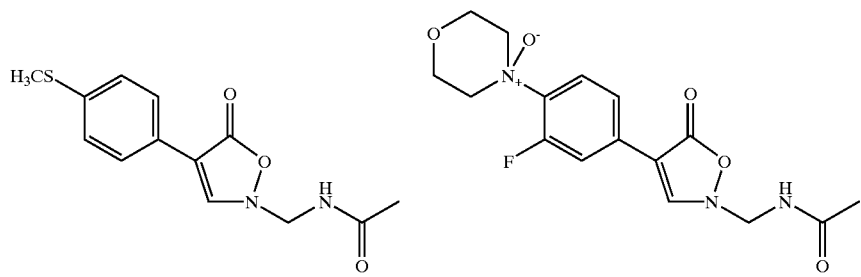

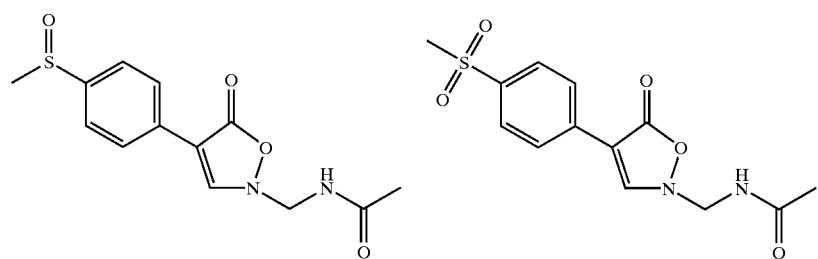

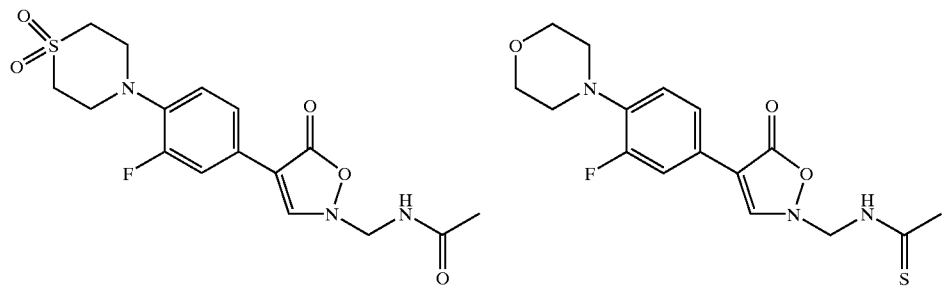

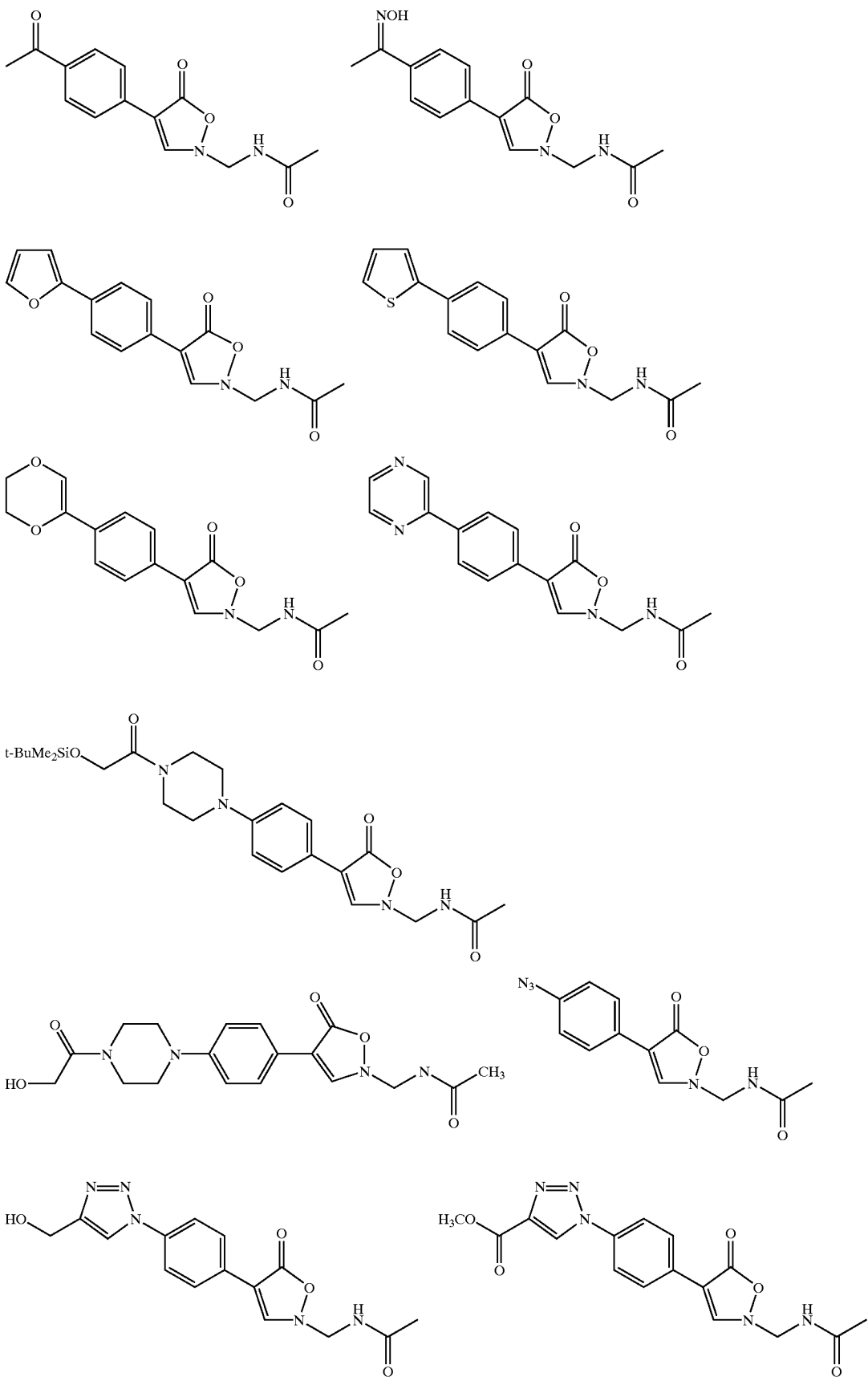

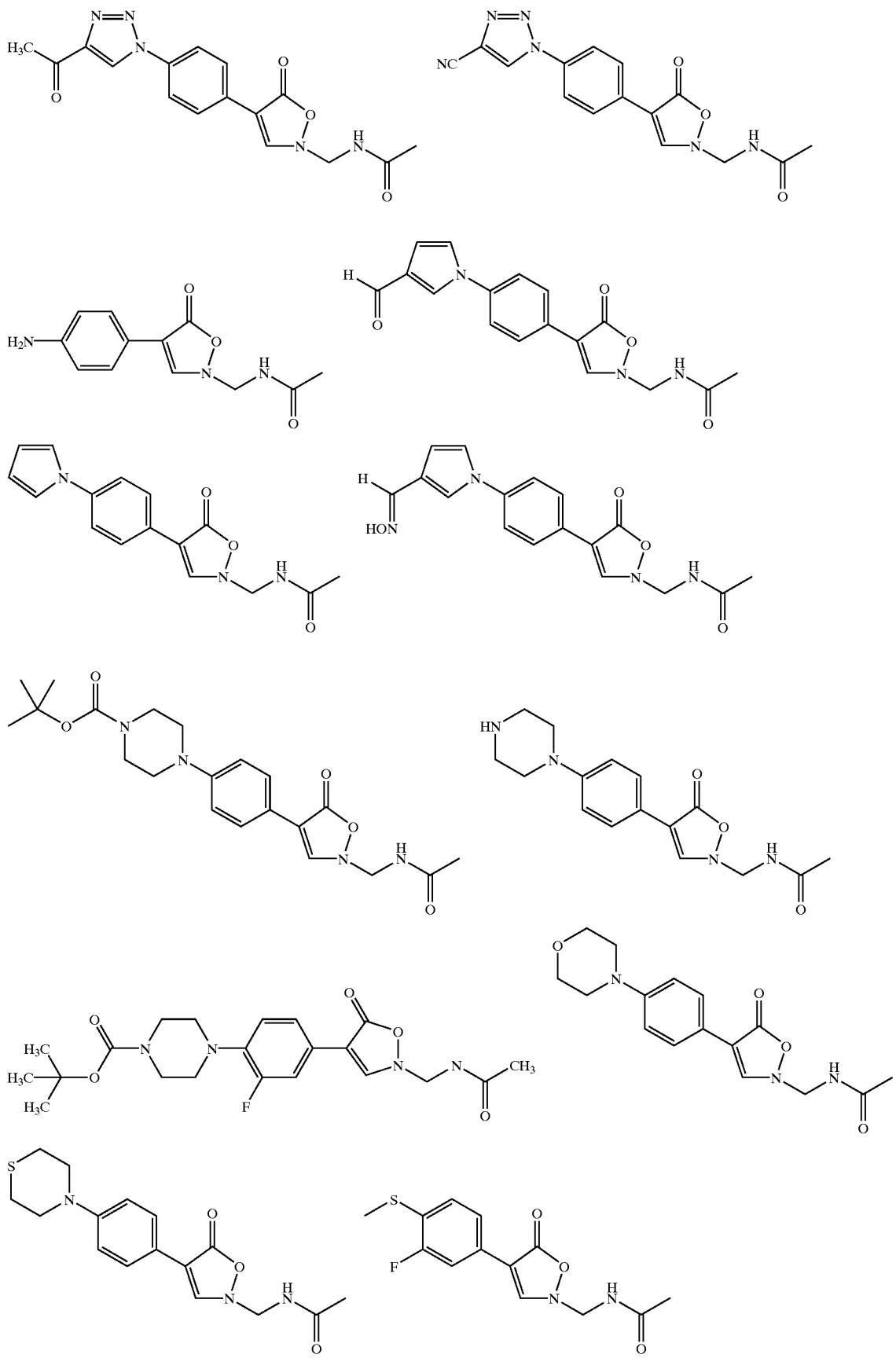

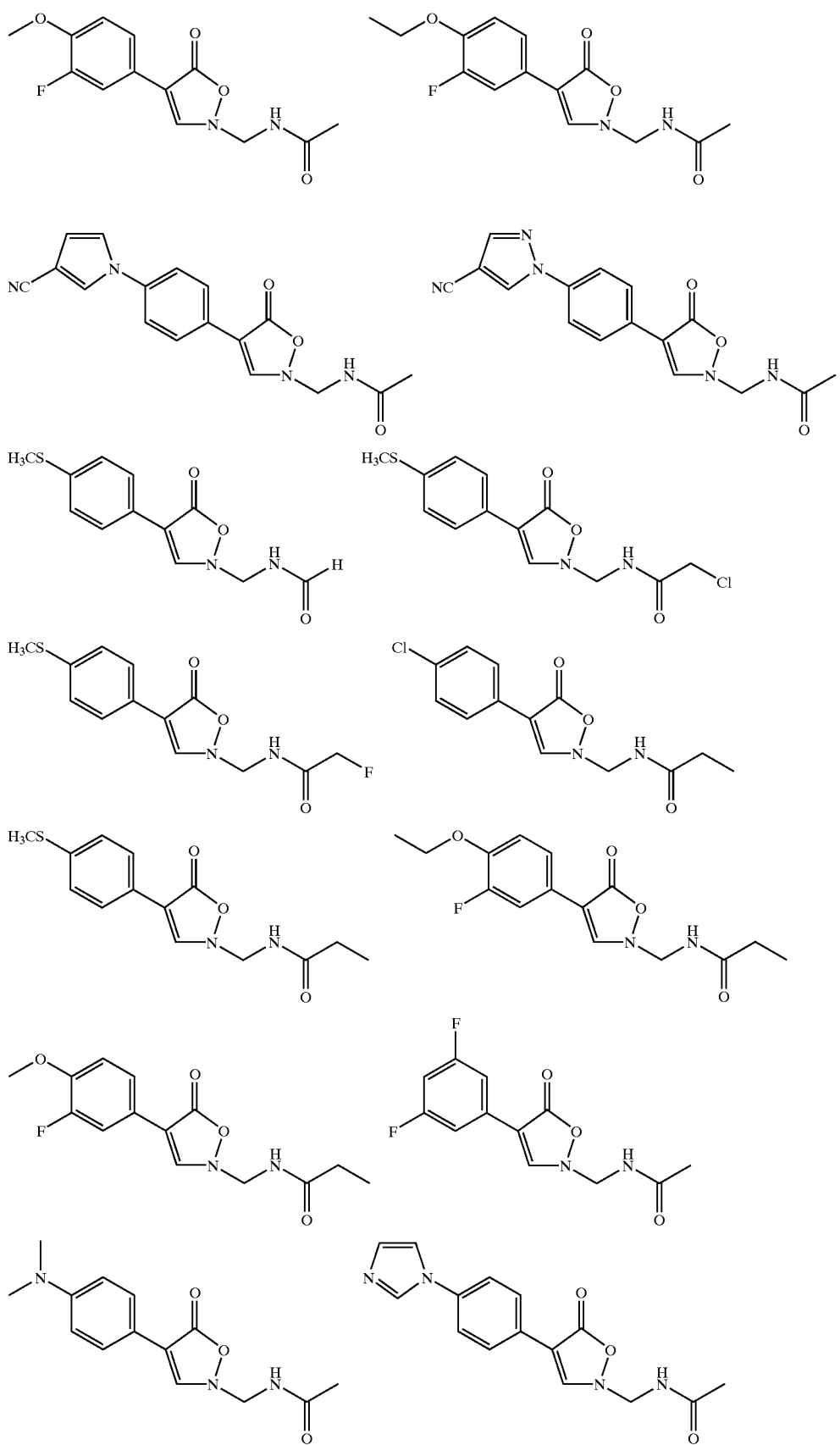

-continued
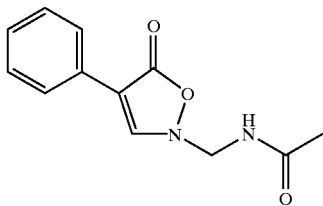
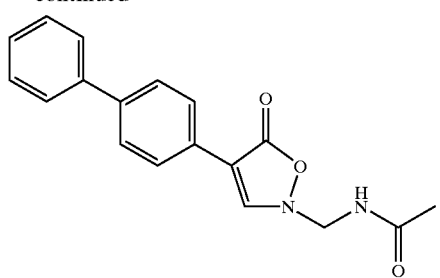
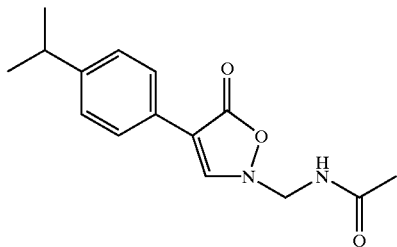
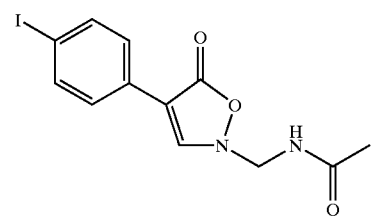
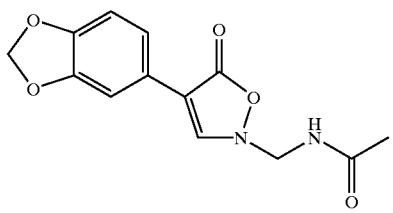
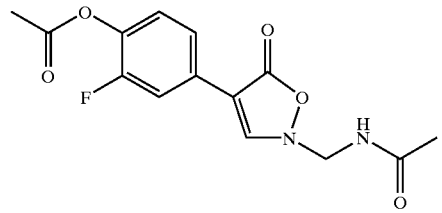
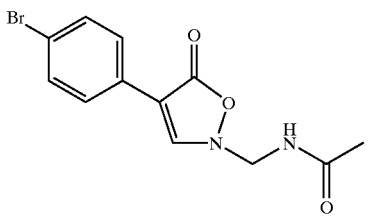
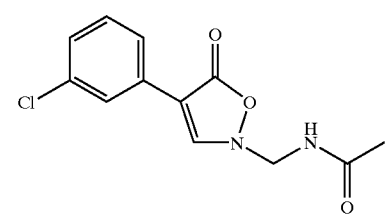
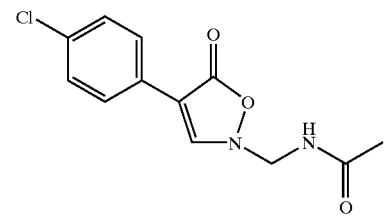
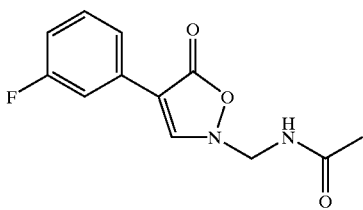
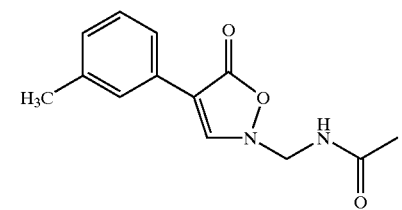
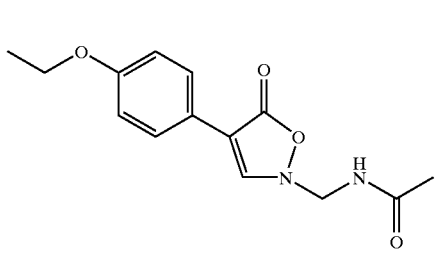
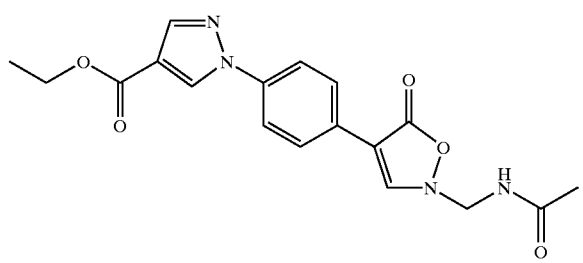
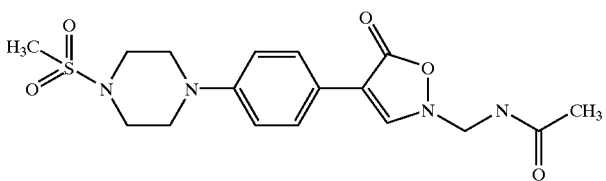

-continued
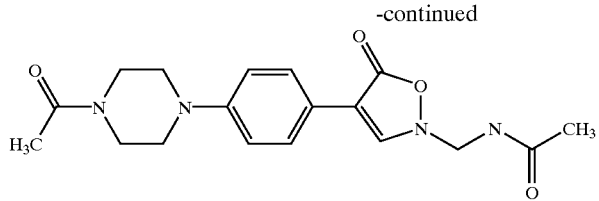
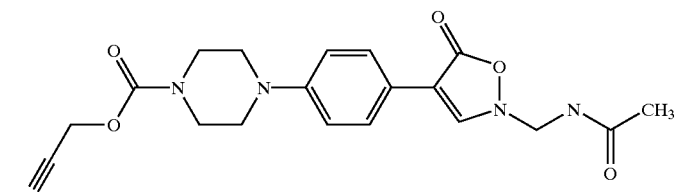
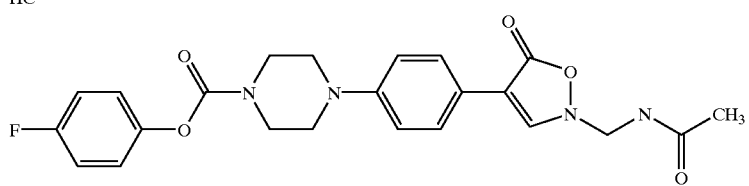
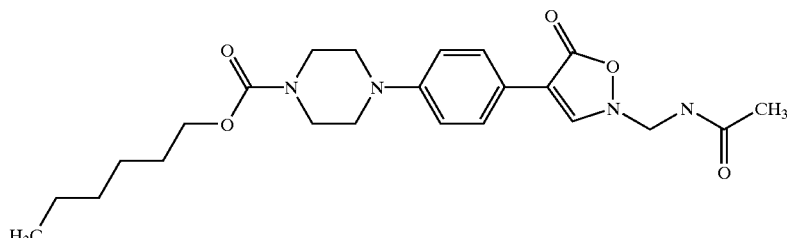
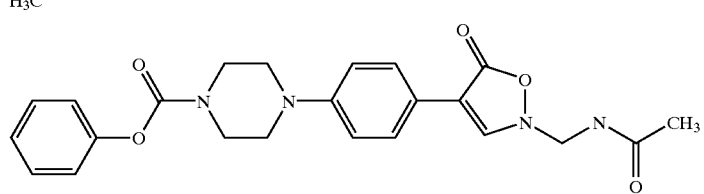
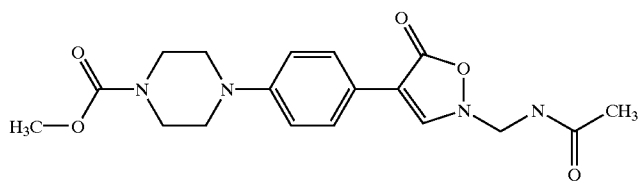
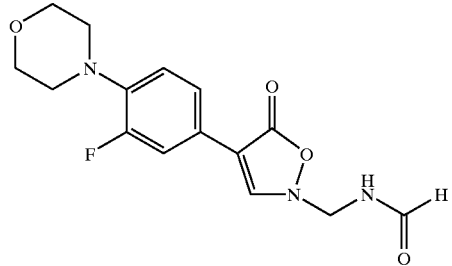
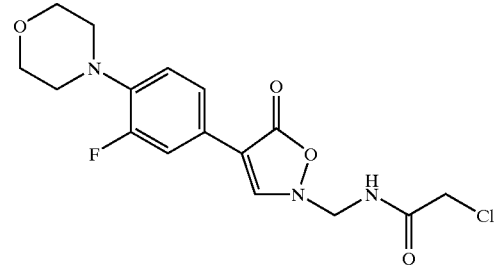
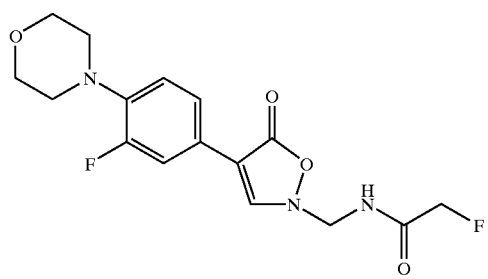
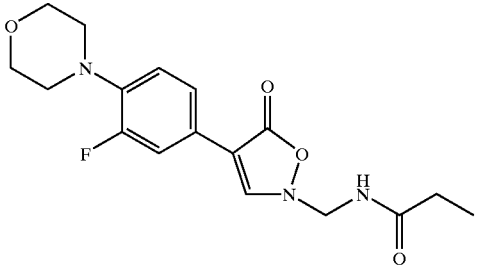

-continued
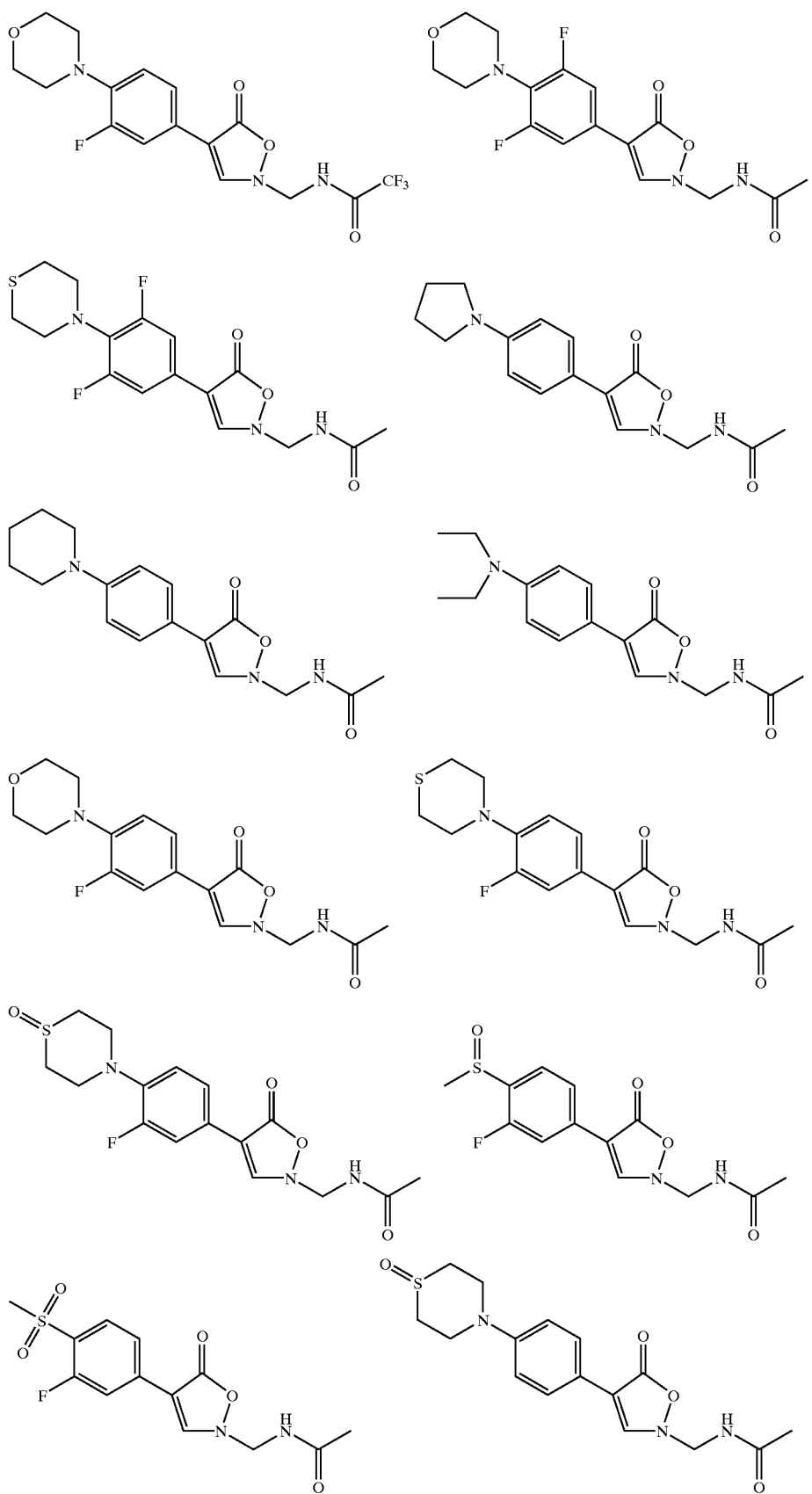

-continued
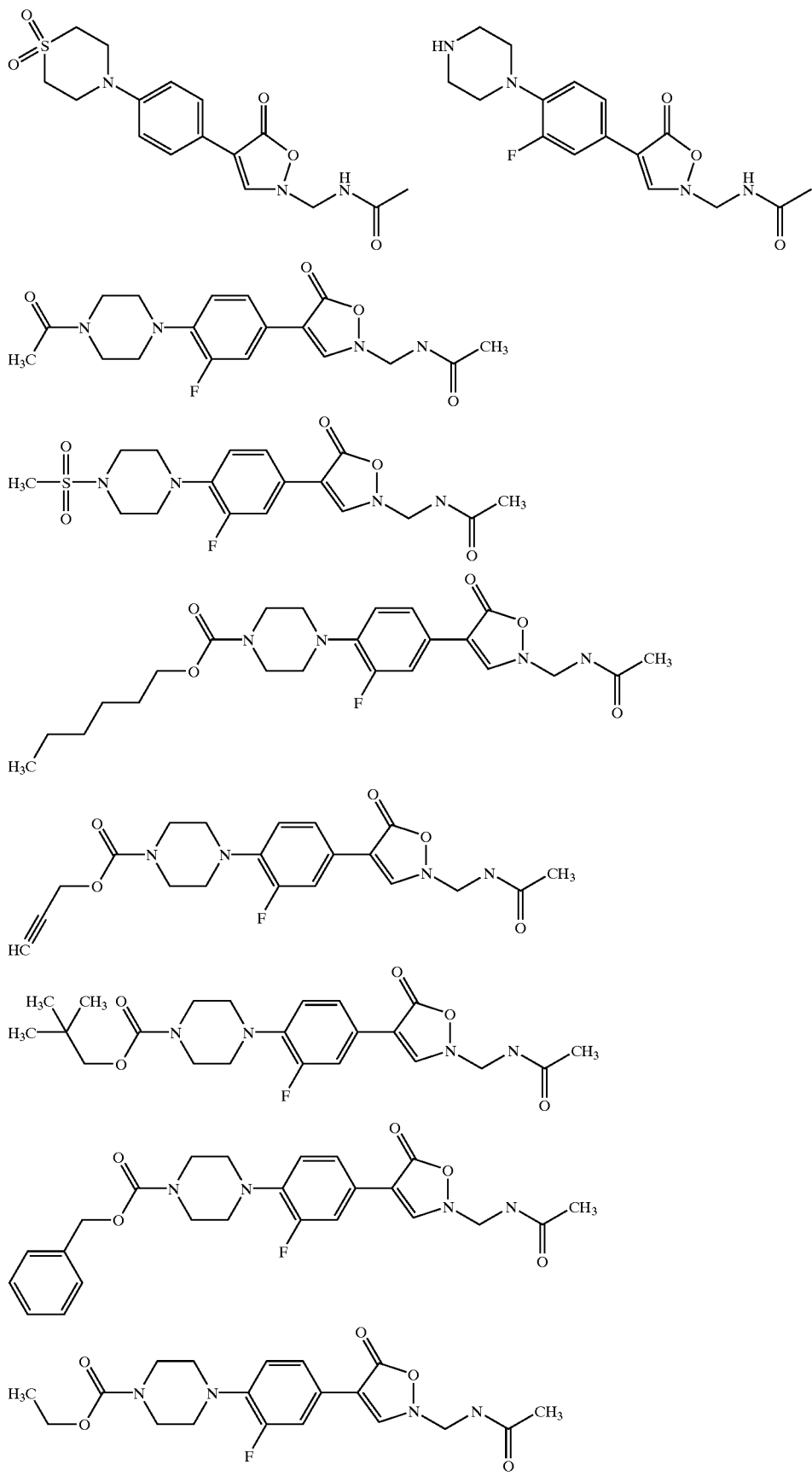

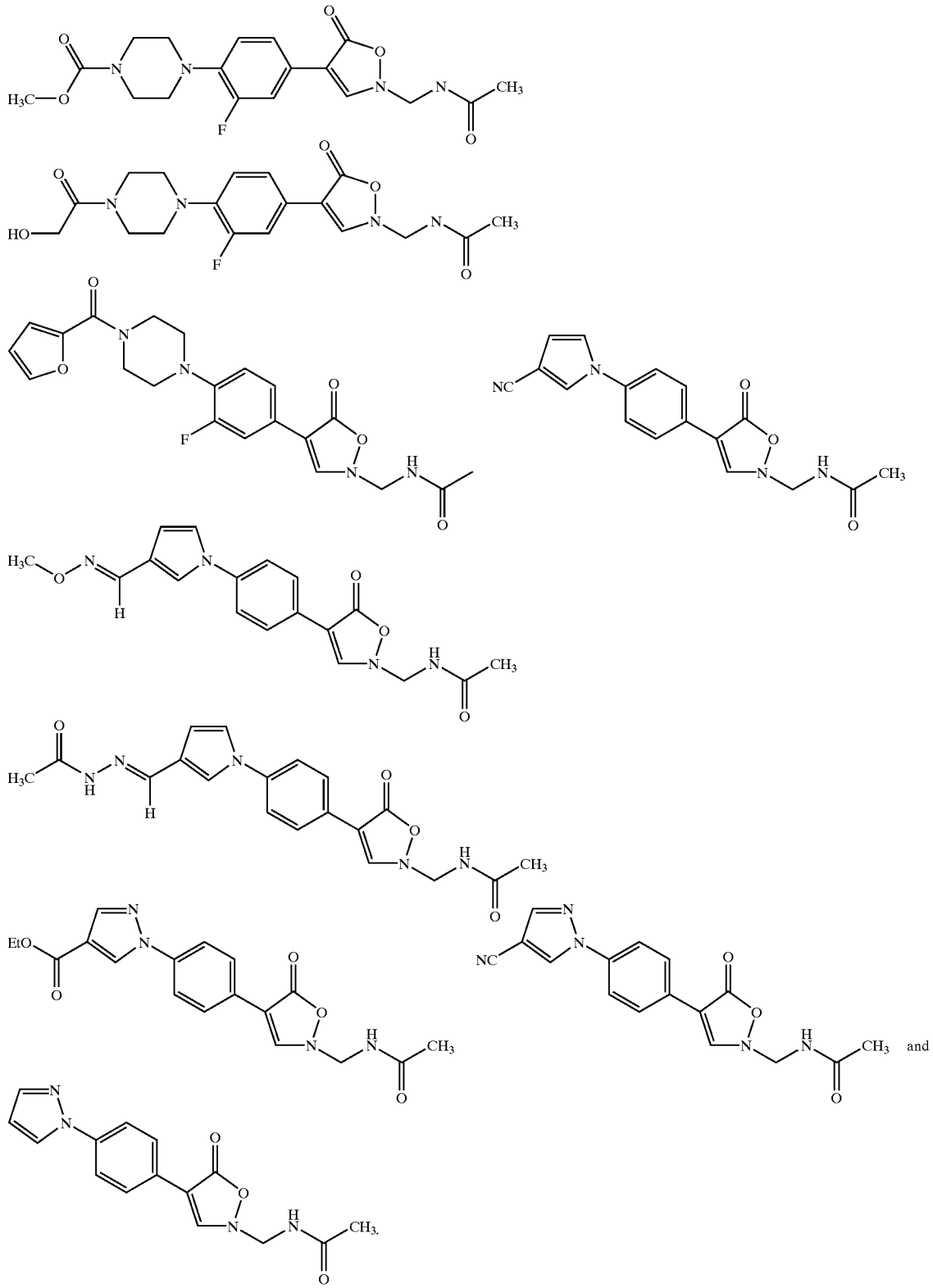
6. A pharmaceutical composition comprising a compound of claim 1 in admixture with a pharmaceutically acceptable carrier.
7. A method of treating a bacterial infection in a mammal which comprises administering a therapeutically effective amount of a compound of claim 1 to a mammal in need thereof.
* * * * *